(12) United States Patent
Paul et al.

(10) Patent No.: US 11,786,620 B2
(45) Date of Patent: Oct. 17, 2023

(54) HANDHELD CLEANER-DISINFECTOR FOR MEDICAL DEVICES

(71) Applicant: CathBuddy, Inc., Woodbury, NY (US)

(72) Inventors: Souvik Paul, Woodbury, NY (US);
Daniel Wollin, Newton, MA (US);
Marjorie Nelson, Woodbury, NY (US)

(73) Assignee: CathBuddy, Inc., Woodbury, NY (US)

( * ) Notice: Subject to any disclaimer, the term of this patent is extended or adjusted under 35 U.S.C. 154(b) by 0 days.

(21) Appl. No.: 17/749,110

(22) Filed: May 19, 2022

(65) Prior Publication Data

US 2022/0273837 A1    Sep. 1, 2022

Related U.S. Application Data

(63) Continuation-in-part of application No. 16/847,830, filed on Apr. 14, 2020, which is a continuation of (Continued)

(51) Int. Cl.
*A61L 2/00*    (2006.01)
*B08B 3/00*    (2006.01)
(Continued)

(52) U.S. Cl.
CPC .................. *A61L 2/10* (2013.01); *A61L 2/085* (2013.01); *A61L 2/12* (2013.01); *A61L 2202/11* (2013.01);
(Continued)

(58) Field of Classification Search
CPC .......... A61L 2/28; A61L 2/24; A61L 2202/14; A61L 2202/24
(Continued)

(56) References Cited

U.S. PATENT DOCUMENTS 3,683,928 A    8/1972  Kuntz
4,391,368 A *  7/1983  Washington, Jr. ..... B65D 83/00
                                                    206/820
(Continued)

FOREIGN PATENT DOCUMENTS

CN    2440517 Y    8/2001
CN  209715892 U   12/2019
(Continued)

OTHER PUBLICATIONS

Jul. 17, 2020—(WO) ISR & WO—App. No. PCT/US20/28733.
(Continued)

*Primary Examiner* — Monzer R Chorbaji
(74) *Attorney, Agent, or Firm* — Banner & Witcoff, Ltd.

(57) ABSTRACT

A cleaning-disinfecting system may be utilized for one or both of cleaning and/or disinfecting medical devices. The cleaning-disinfecting system may be a portable battery-powered medical device washer-disinfector. The systems, devices, or methods may be specifically designed for use at home or other contexts and can wash and disinfect single or multiple medical devices simultaneously. The cleaning-disinfecting system may automatically reprocess medical devices placed within the cleaning-disinfecting system. The cleaning-disinfecting system may store medical devices after reprocessing without exposing the medical devices to potential contamination from the environment.

30 Claims, 49 Drawing Sheets

Related U.S. Application Data application No. 16/399,658, filed on Apr. 30, 2019, now Pat. No. 10,639,389.

(60) Provisional application No. 62/664,744, filed on Apr. 30, 2018.

(51) Int. Cl.
    *A61B 1/00*     (2006.01)
    *A61L 2/10*     (2006.01)
    *A61L 2/12*     (2006.01)
    *A61L 2/08*     (2006.01)

(52) U.S. Cl.
    CPC ..... *A61L 2202/122* (2013.01); *A61L 2202/14* (2013.01); *A61L 2202/24* (2013.01)

(58) Field of Classification Search
    USPC ....... 422/28, 292; 134/95.3, 166 R; 206/820; 600/118
    See application file for complete search history.

(56) References Cited

U.S. PATENT DOCUMENTS

| | | | |
|---|---|---|---|
| 5,260,020 A | | 11/1993 | Wilk et al. |
| 5,275,668 A | * | 1/1994 | Dell ................... A61B 90/70 |
| | | | 134/186 |
| 5,310,524 A | | 5/1994 | Campbell et al. |
| 5,494,637 A | * | 2/1996 | Barlow ................. A61B 90/70 |
| | | | 422/106 |
| 5,711,921 A | * | 1/1998 | Langford ............... A61B 90/70 |
| | | | 422/294 |
| 5,785,678 A | | 7/1998 | Griep et al. |
| 6,461,569 B1 | | 10/2002 | Boudreaux |
| 7,537,589 B2 | | 5/2009 | Tsukada et al. |
| 7,717,902 B2 | | 5/2010 | Sauer |
| 7,905,831 B2 | * | 3/2011 | Noguchi ............ A61B 1/00128 |
| | | | 600/118 |
| 8,114,063 B2 | | 2/2012 | Sacco et al. |
| 8,496,610 B2 | | 7/2013 | Levenson et al. |
| 8,556,884 B2 | | 10/2013 | Hong et al. |
| 8,933,416 B2 | | 1/2015 | Arcand et al. |
| 8,946,653 B2 | | 2/2015 | Victor et al. |
| 8,974,438 B2 | | 3/2015 | Hong et al. |
| 9,168,354 B2 | | 10/2015 | Hannon et al. |
| 9,421,290 B2 | | 8/2016 | Victor et al. |
| 9,492,574 B2 | | 11/2016 | Rasooly et al. |
| 9,550,005 B2 | | 1/2017 | Lin et al. |
| 9,808,647 B2 | | 11/2017 | Rhodes et al. |
| 9,865,018 B2 | | 1/2018 | Bowne et al. |
| 9,877,176 B2 | | 1/2018 | Gabel |
| 10,639,389 B2 | | 5/2020 | Paul et al. |
| 10,850,062 B2 | | 12/2020 | Vazales et al. |
| 11,027,112 B2 | | 6/2021 | Kheir et al. |
| 2003/0017073 A1 | | 1/2003 | Eckhardt et al. |
| 2005/0135965 A1 | | 6/2005 | Williams et al. |
| 2005/0205206 A1 | | 9/2005 | Lembersky |
| 2008/0159908 A1 | | 7/2008 | Redmond |
| 2010/0286479 A1 | * | 11/2010 | Ashida ............ A61M 25/10184 |
| | | | 600/116 |
| 2011/0044848 A1 | | 2/2011 | Wright |
| 2011/0224649 A1 | | 9/2011 | Duane et al. |
| 2012/0230868 A1 | | 9/2012 | Reddy et al. |
| 2013/0256560 A1 | | 10/2013 | Yerby |
| 2014/0264074 A1 | | 9/2014 | Victor et al. |
| 2015/0231287 A1 | | 8/2015 | Lin et al. |
| 2015/0362828 A1 | * | 12/2015 | Patel .................... A61B 5/6898 |
| | | | 348/75 |
| 2015/0366462 A1 | | 12/2015 | Ramos |
| 2015/0374868 A1 | | 12/2015 | Bruce et al. |
| 2016/0001037 A1 | | 1/2016 | Hong et al. |
| 2016/0193375 A1 | | 7/2016 | Laflamme et al. |
| 2017/0119915 A1 | | 5/2017 | Lin et al. |
| 2017/0136209 A1 | | 5/2017 | Burnett et al. |
| 2017/0165386 A1 | | 6/2017 | Huang |
| 2017/0224952 A1 | | 8/2017 | Barneck et al. |
| 2017/0252472 A1 | | 9/2017 | Dang et al. |
| 2017/0252473 A1 | * | 9/2017 | Thompson ................ A61L 2/24 |
| 2018/0036510 A1 | | 2/2018 | Tanghoej et al. |
| 2018/0071482 A1 | | 3/2018 | Fitzpatrick et al. |
| 2019/0290791 A1 | | 9/2019 | Baker et al. |
| 2019/0328915 A1 | | 10/2019 | Paul et al. |
| 2020/0188543 A1 | | 6/2020 | Etter et al. |
| 2020/0324006 A1 | | 10/2020 | Paul et al. |
| 2021/0023348 A1 | | 1/2021 | Matsushita et al. |
| 2021/0100982 A1 | | 4/2021 | Laby et al. |
| 2021/0113725 A1 | | 4/2021 | Etter et al. |

FOREIGN PATENT DOCUMENTS

| | | |
|---|---|---|
| CN | 213031135 U | 4/2021 |
| DE | 202011107059 U1 | 1/2013 |
| EP | 3308823 A1 | 4/2018 |
| EP | 2471569 B1 | 10/2018 |
| JP | 6535126 B2 | 6/2019 |
| KR | 20140139477 A | 12/2014 |
| KR | 101657873 B1 | 9/2016 |
| WO | 2020252045 A1 | 12/2020 |
| WO | 2021061661 A1 | 4/2021 |

OTHER PUBLICATIONS

Souvik Paul, CleanCath Catheter Sterilizer, https://designawards.core77.com/Strategy-Research/64780/CleanCath-Catheter-Sterilizer, visited Sep. 2, 2021.

besttechnologyinc.com, Automated Ultrasonic Medical Device Catheter Cleaning System, https://www.besttechnologyinc.com/case-studies/medical-device-catheter-cleaning-system/, visited Sep. 2, 2021.

bardcare.com, Urological Products Product Catalog, visited Sep. 2, 2021.

180medical.com, The Full Guide to No-Touch Catheters, https://www.180medical.com/blog/the-full-guide-to-no-touch-catheters/, visited Sep. 2, 2021.

cincinnatichildrens.org, Sterilization of Urinary Catheters, https://www.cincinnatichildrens.org/health/s/steril-catheters, visited Sep. 2, 2021.

\* cited by examiner

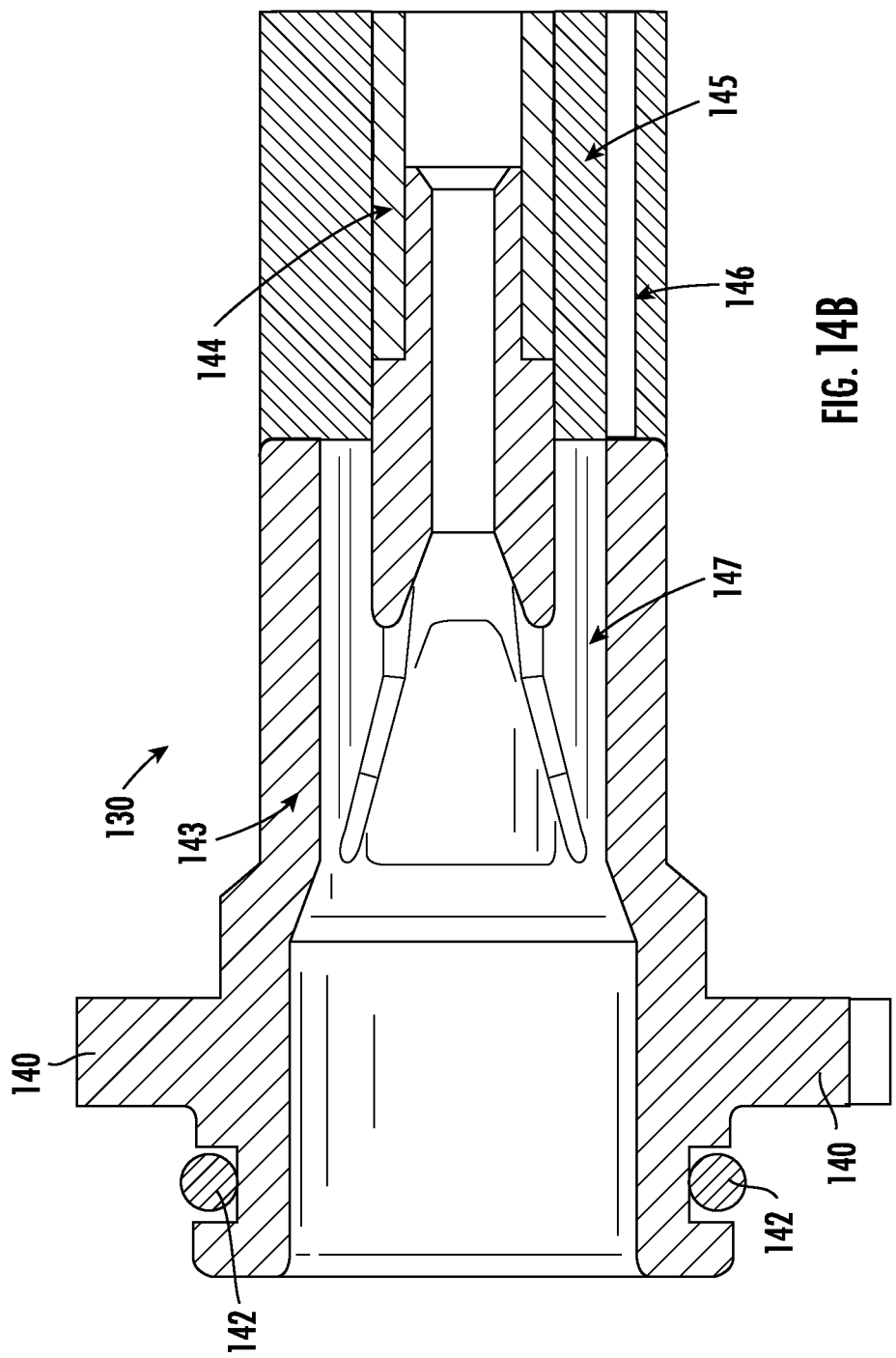

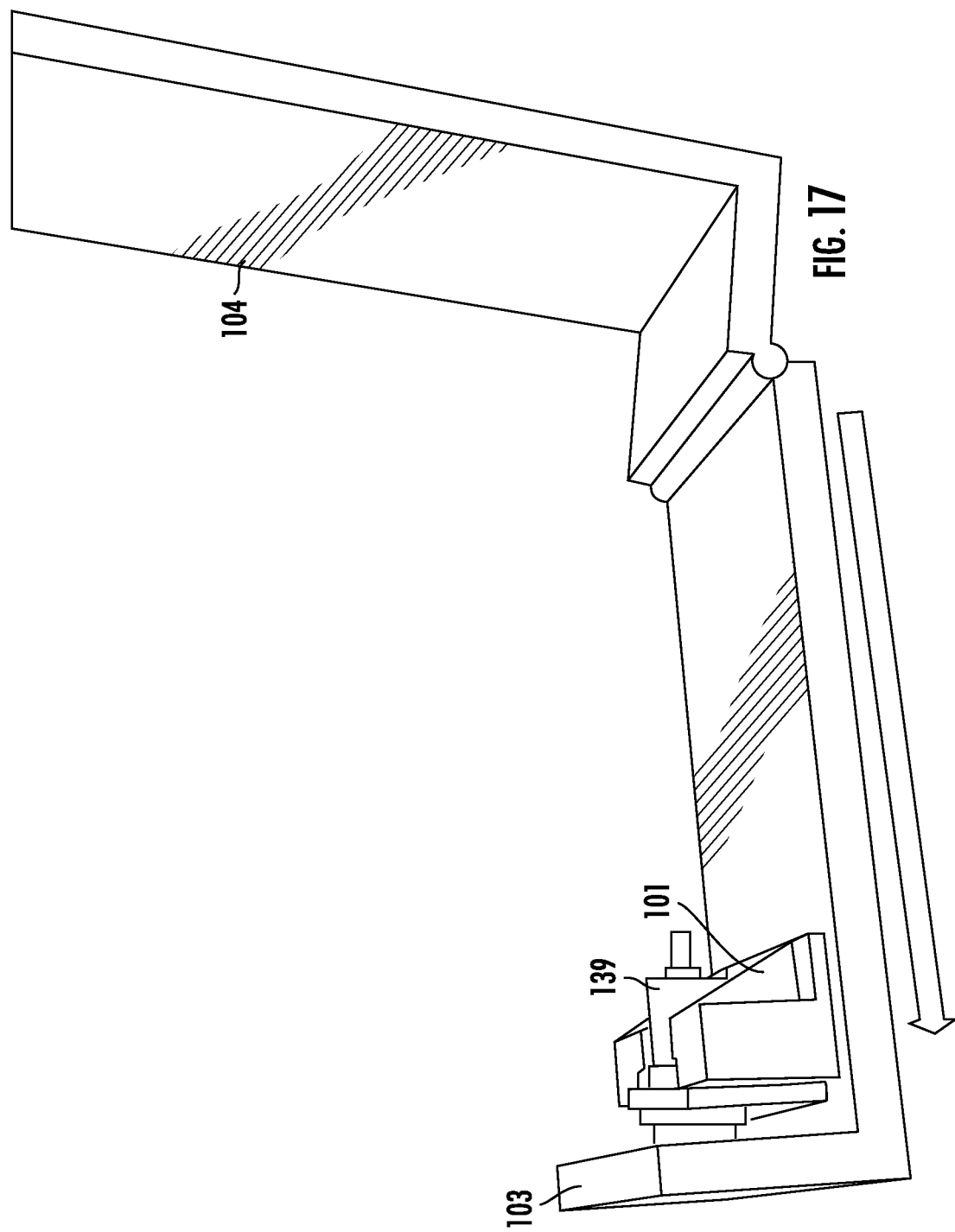

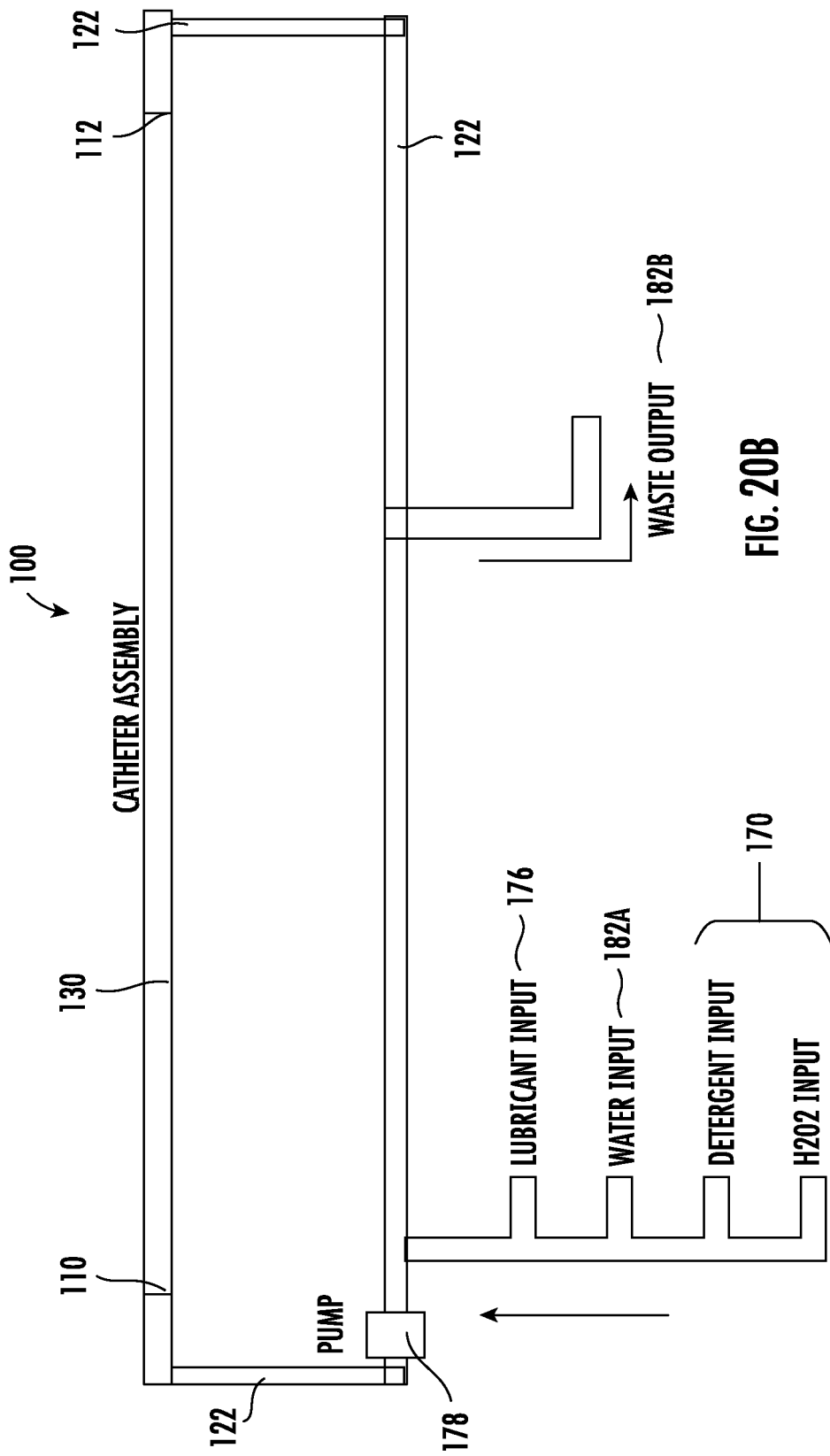

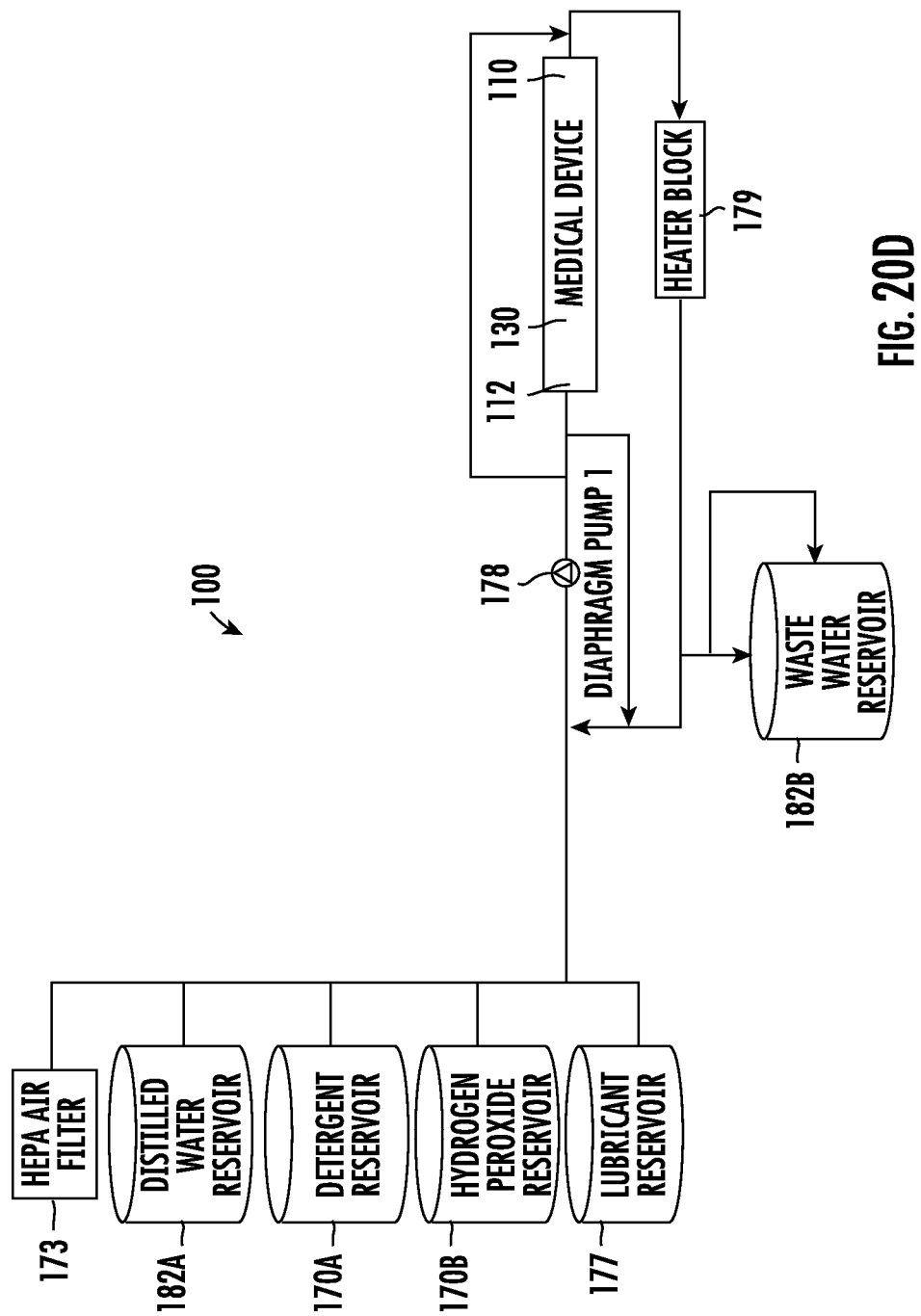

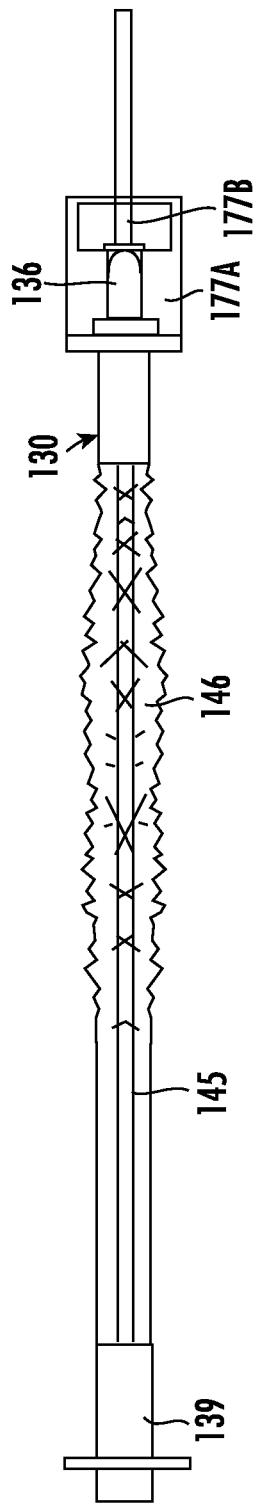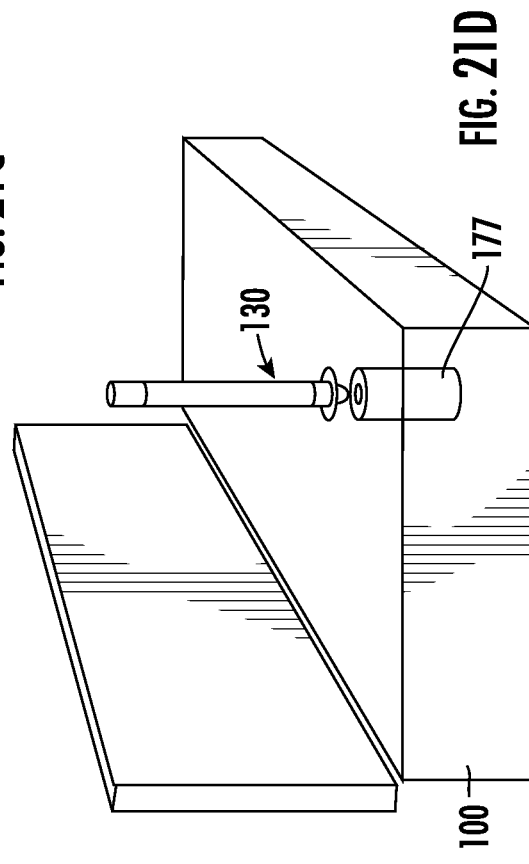
FIG. 21C
FIG. 21D

HANDHELD CLEANER-DISINFECTOR FOR MEDICAL DEVICES

CROSS-REFERENCE TO RELATED APPLICATIONS

This application is a continuation-in-part application to U.S. patent application Ser. No. 16/847,830, filed Apr. 14, 2020, which claims priority and is a continuation to U.S. patent application Ser. No. 16/399,658, filed Apr. 30, 2019, and issued as U.S. Pat. No. 10,639,389 on May 5, 2020, which claims priority to U.S. Provisional Patent Application No. 62/664,744, filed Apr. 30, 2018, entitled Methods and Devices for Portable Sterilization and Containment of Medical Devices, which are all incorporated herein by reference in its entirety and made a part hereof.

TECHNICAL FIELD

The invention relates to cleaning and disinfecting medical devices, and, more particularly, the combined use of cleaning methods and high-level disinfectants to clean and disinfect medical devices in a handheld apparatus.

BACKGROUND OF THE INVENTION

Medical device washer-disinfectors are well known in the art. While medical device washer-disinfectors according to the prior art provide a number of advantageous features, they nevertheless have certain limitations. The present invention seeks to overcome certain of these limitations and other drawbacks of the prior art, and to provide new features not heretofore available. A full discussion of the features and advantages of the present invention is deferred to the following detailed description, which proceeds with reference to the accompanying drawings.

SUMMARY

The present invention generally provides methods and devices for the handheld cleaning and disinfection of medical devices and supplies.

According to one embodiment, a system for reprocessing one or more medical devices that may comprise: a portable, medical device washer-disinfector to execute a reprocessing cycle with one or more medical devices. The medical device washer-disinfector may comprise a first housing with a first flow connector configured connect to a first end of the medical device, and a second housing with a second flow connector configured to connect to a second end of the medical device, thereby creating a closed-loop fluid pathway for reprocessing fluids to flow through the one or more medical devices and the medical device washer-disinfector.

According to another embodiment, a medical device washer-disinfector to execute a reprocessing cycle with one or more medical devices, with the medical device washer-disinfector comprising: a base unit and a detachable case configured to detach from the base unit, a first housing with a first flow connector configured connect to a first end of the medical device, and a second housing with a second flow connector configured to connect to a second end of the medical device. Additionally, the detachable case may include a mounting tray configured to hold the one or more medical devices and a lid that provides access to the mounting tray. The connections with the first end and the second end of the medical device thereby creating a closed-loop fluid pathway for reprocessing fluids to flow through the one or more medical devices and the medical device washer-disinfector. The medical device washer-disinfector may further comprise an RFID/NFC system that includes an RFID/NFC scanner located within the medical device washer-disinfector that is configured to scan an RFID/NFC tag located within the one or more medical devices.

According to another embodiment, a method for reprocessing one or more medical devices, the method may comprise: enclosing a medical device in a cleaning-disinfection system; sealing the first end of the medical device against the first housing and first flow connector; sealing the second end of the medical device against the second housing and the second flow connector; filling with water a clean water reservoir connected to the closed-loop fluid pathway; activating a reprocessing cycle for the medical device washer-disinfector; cleaning, by the medical device washer-disinfector, surfaces of the medical device with water and enzymatic cleaning detergents; and disinfecting, by the medical device washer-disinfector, the surfaces of the medical device with high-level disinfectants or a liquid chemical sterilant. The cleaning-disinfection system may include a portable, medical device washer-disinfector to execute a reprocessing cycle with one or more medical devices. The medical device washer-disinfector may comprise: a first housing with a first flow connector configured connect to a first end of the medical device, and a second housing with a second flow connector configured to connect to a second end of the medical device, thereby creating a closed-loop fluid pathway for reprocessing fluids to flow through the one or more medical devices and the medical device washer-disinfector.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIGS. 14A and 14B are cross-section views of the flow connectors and housings for cleaning-disinfecting system for a medical device according to one embodiment of the invention.

FIG. 17 is a perspective view of another illustrative embodiment of a closing system for a cleaning-disinfecting system for a medical device according to one embodiment of the invention.

FIGS. 20B-20D are flow charts for various cleaning-disinfecting systems for a medical device according to one or more embodiments of the invention.

FIGS. 21A-21D are various views of a cleaning-disinfecting systems for applying lubricant according to one embodiment of the invention.

Figure 1:
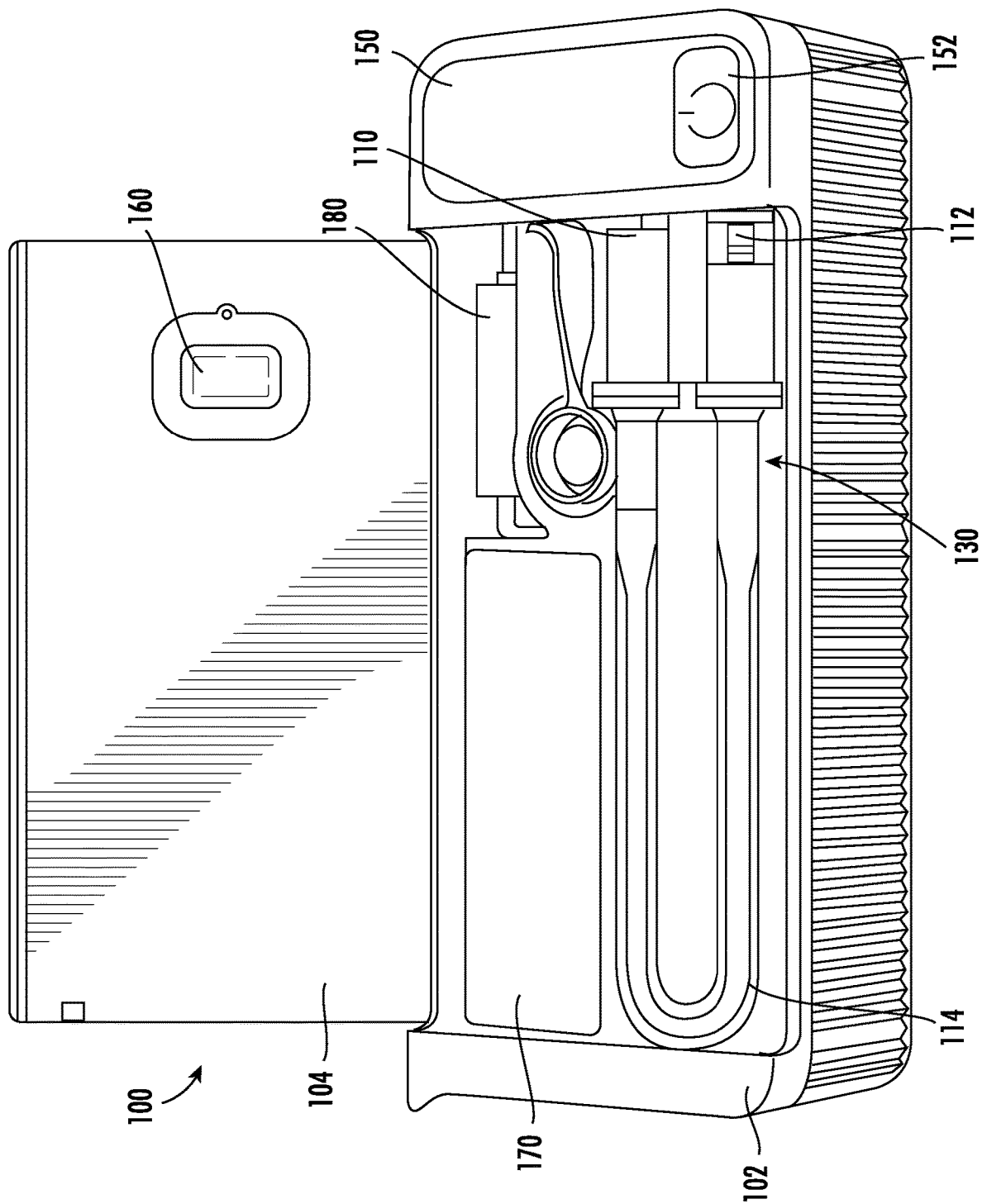
FIG. 1 is a perspective view of an illustrative embodiment of a cleaning-disinfecting system for a medical device according to one embodiment of the invention.

The above-mentioned and other features of the inventions disclosed herein are described below with reference to the drawings of the preferred embodiments. The illustrated embodiments are intended to illustrate, but not to limit the inventions.

DETAILED DESCRIPTION

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

In the following detailed description for purposes of explanation and not limitation, exemplary embodiments disclosing specific details are set forth in order to provide a thorough understanding of the present invention. It will be apparent, however, to one having ordinary skill in the art that the present invention may be practiced in other embodiments that depart from the specific details disclosed herein. In other instances, detailed description of well-known devices and methods may be omitted so as not to obscure the description of the present invention.

In the practice of medicine, reusable medical devices are typically defined as devices that healthcare providers can reprocess and reuse on multiple patients. Washer-disinfectors are utilized primarily in hospital or other clinical settings to clean and disinfect reusable medical devices that are classified as semi-critical or non-critical devices according to the degree of risk of infection associated with the use of the device, whereas sterilizers are used to sterilize critical medical devices, such as surgical forceps. Endoscopes are an example of semi-critical reusable medical devices, whereas stethoscopes are an example of non-critical reusable medical devices. These reusable medical devices may themselves have accessories that need to be reprocessed and cleaned and disinfected in a manner consistent with the reusable medical device itself.

Reprocessing may be known and used in the art to define validated processes used to render a medical device, which has been previously used or contaminated, fit for a subsequent single use. These processes are designed to remove soil and contaminants by cleaning and to inactivate microorganisms by disinfection and/or sterilization.

Cleaning may be known and used in the art to define the application of detergents and surfactants to remove soils. Cleaning is a chemically distinct process from sterilization or disinfection. Cleaning is the removal of visible soil (e.g., organic and inorganic material) from objects and surfaces to the extent necessary for further processing. Cleaning may be normally accomplished manually or mechanically using water with detergents or enzymatic products. Thorough cleaning is essential before high-level disinfection and sterilization because inorganic and organic materials that remain on the surfaces of instruments interfere with the effectiveness of these processes. Decontamination removes pathogenic microorganisms from objects so they are safe to handle, use, or discard.

Disinfection may be known and used in the art to define a process that destroys pathogens and other microorganisms by physical or chemical means. Disinfection processes do not ensure the same margin of safety associated with sterilization processes. The lethality of the disinfection process may vary, depending on the nature of the disinfectant. A disinfectant is an agent that destroys pathogenic and other kinds of microorganisms by chemical or physical means. A disinfectant may destroy most recognized pathogenic microorganisms, but not necessarily all microbial forms, such as bacterial spores. High-level disinfection may be defined as the process of using a sterilant in which all forms of microbial life, except for large numbers of bacterial spores, is killed.

The need to reprocess medical devices comes from the fact that medical devices require financial capital and resources to manufacture, and using these medical devices in a single-use fashion is not economically or environmentally sustainable. In the course of their intended use, these medical devices may come into contact with biological soils that harbor and transmit microorganisms that cause illness and disease. The purpose of reprocessing is to remove any buildup of biological soils, such as but not limited to blood, fat, or protein, prior to the deactivation of microorganisms so that they cannot reproduce and potentially cause infection when the device is reused on another patient.

The FDA has issued guidelines for processes used to clean and disinfect or sterilize reusable medical devices. Reprocessing begins at the point of use, when reusable devices are segregated from use and typically wiped clean of visible soil. Thorough cleaning involves the disassembly of medical devices to facilitate cleaning and the removal of bodily soils through the use of detergents, enzymatic cleaners, ultrasound baths, and brushes. Final processing involves the use of disinfection or sterilization methods to inactivate any microorganisms that remain on the surfaces of the medical devices being reprocessed.

Separately, there are industry standards that govern the quality of water that is used in medical device reprocessing so as to avoid scenarios where contaminated water re-inoculates a disinfected or sterilized medical device with additional pathogens.

Medical device reprocessing typically occurs in hospitals or similar clinical settings where reusable medical devices are typically utilized, or in specialized facilities that receive large volumes of used reusable medical devices from hospitals for reprocessing. The reprocessing of medical devices therefore usually involves the simultaneous reprocessing of several devices at once. As a result, medical device washer-disinfectors and medical device sterilizers are configured to be large appliances with capacity for multiple devices. Furthermore, medical device washer-disinfectors and medical device sterilizers are typically operated by healthcare professionals.

Intermittent urinary catheters are essential medical devices that are typically used by individuals with neurogenic bladder and lower urinary tract symptoms to manually empty the bladder of urine if it is neurologically or physically obstructed. While the use of these catheters is oftentimes considered to be the healthiest short- or long-term method for bladder management, especially when compared to alternatives like suprapubic or indwelling catheters, improper use of these catheters can result in contact contamination of the catheter, the subsequent introduction of pathogens to the bladder, and an overall substantially higher urinary tract infection [UTI] risk for the individual. Additionally, improper use of the catheter is extremely likely given the overall lack of ergonomic consideration in the design of the catheter in the case of standard, low-cost catheters. While easier-to-use catheters do exist, they do so at a price point that is often 5-7× the price of standard, low-cost catheters. Insurance coverage of these easier-to-use catheters is limited, and reuse is prevalent to offset the financial cost to the individual. Moreover, compliance with clean catheterization guidelines is generally low due to their onerous nature and requirement of a vast kit of parts that are difficult, if not impossible, to transport.

A need exists for an easy-to-use and affordable catheterization cleaning-disinfecting system that mitigates the UTI risk associated with the use of today's catheters.

The cleaning-disinfecting system relates to enabling individuals who rely on medical devices and supplies in their daily lives to reuse these medical devices and supplies safely, in compliance with FDA recommendations with an automated and handheld medical device washer-disinfector, while in contexts including but not limited to their homes, their workplaces, and in transit. Moreover, the devices, systems, and methods according to the cleaning-disinfecting system preferably provide increased standardization for cleaning and disinfecting medical devices along with the combined data acquisition and deposition for those medical devices.

One preferred embodiment relates to devices, systems, or methods directed to a cleaning-disinfecting system that may be utilized for one or both of cleaning and/or disinfecting. The cleaning-disinfecting system may be a portable battery-powered medical device washer-disinfector. In another embodiment, the systems, devices, or methods may be specifically designed for use at home and can wash and disinfect multiple medical devices simultaneously. In yet another embodiment, the devices, systems, or methods may be intended to be stored on a flat horizontal surface such as a countertop or a desk, or may be disguised as a commonplace consumer object such as, but not limited to, a bookbag.

Another embodiment relates to devices, systems, or methods that may automatically reprocesses medical devices placed within the cleaning-disinfecting system. The cleaning-disinfecting system may store medical devices after reprocessing without exposing the medical devices to potential contamination from the environment. Moreover, the devices, systems, and methods according to an embodiment may preferably provide automated standardization for cleaning and disinfecting and/or sterilization in a manner that minimizes the need for operator input to reduce the risk of inadequate and/or inconsistent reprocessing.

Another embodiment relates to devices, systems, or methods that may have the capability to actively monitor critical process parameters such as, but not limited to, concentration of reprocessing materials being circulated in and around the medical device, time elapsed, temperature of the system, and atmospheric pressure in order to dynamically change the length of the reprocessing process to ensure complete cleaning and disinfection of the medical device inserted into the cleaning-disinfecting system.

Another embodiment relates to devices, systems, or methods that may be capable of high-level disinfecting or sterilizing medical devices and supplies, preferably catheters, or other products, using a combination of enzymatic cleaners and high level disinfectants or liquid chemical sterilants. According to one preferred embodiment, the medical device or supply, when inserted into the cleaning-disinfecting system, interfaces with the cleaning-disinfecting system through a water-tight and air-tight seal, forming a closed-loop fluid pathway with the cleaning-disinfecting system. This embodiment of the cleaning-disinfecting system helps to reduce the overall fluid volume needed to completely reprocess the medical device and supply in question. One embodiment of the cleaning-disinfecting system may achieve the circulation of reprocessing materials through the medical device and supply using a diaphragm or peristaltic pump.

According to another preferred embodiment, medical devices or supplies are loaded into the system in a particular orientation to facilitate the flow of fluids through the devices or supplies in order to minimize the amount of air trapped in the system. In the preferred embodiment of the system, magnets are utilized to properly seat the medical devices or supplies into the cleaning-disinfecting system, reducing the operator's need to physically push or pull the medical devices or supplies into position. The medical device may be further positioned optimally within the cleaning-disinfecting system through the use of spring-loaded, dynamic or static features with lead-ins that compress the medical device against the cleaning-disinfecting system in order to create a water-tight and/or air-tight seal. Another embodiment of the cleaning-disinfecting system may utilize an asymmetric array of magnets to facilitate the loading of the medical device in a particular orientation to prevent twisting or otherwise disadvantageous positioning of the medical device in the cleaning-disinfecting system that may damage the device or prevent the complete cleaning and disinfection of the device within the cleaning-disinfecting system. The medical device itself may feature magnets or ferrous metal to facilitate a magnetically-augmented loading mechanism into the cleaning-disinfecting system. In various embodiments of the cleaning-disinfecting system, the medical devices may be stored in a straight orientation, a u-shaped orientation, a looped orientation, or a coiled orientation to reduce the amount of space that the medical device takes up within the cleaning-disinfecting system.

In another embodiment of the cleaning-disinfecting system, the medical device may connect to an electronic interface that charges an on-board battery present on the medical device; charging of the on-board battery may also be facilitated through wireless charging interfaces. The medical devices inserted into the cleaning-disinfecting system may be oriented such that the proximal end of the device which enters the user's body when being used faces against the flow of reprocessing fluids in the system; in other embodiments of the cleaning-disinfecting system, the proximal end of the device may face inline with the flow of reprocessing fluids in the system.

In another embodiment of the system, the medical devices may be loaded into the system in an orientation that facilitates the scanning of an embedded RFID or NFC tag in the device with an NFC or RFID scanner present in the cleaning-disinfecting system; the scanning of the RFID or NFC tag may facilitate the identification of the medical device as suitable to be reprocessed within the system and the prevention of reprocessing of medical devices that are not intended to be reprocessed within the system. In the preferred embodiment of the cleaning-disinfecting system, a valid RFID or NFC tag must be identified as a prerequisite to begin the reprocessing cycle, otherwise the cleaning-disinfecting system displays an error message to the user through a human-computer interface and does not begin the reprocessing cycle. The cleaning-disinfecting system can also utilize the RFID or NFC tag to track how many times a device has been reprocessed with the cleaning-disinfecting system by writing to the RFID or NFC tag after every successfully completed cycle—this is done to prevent overuse of the cleaning-disinfecting system to reprocess the medical device beyond its safe lifetime of use. In another embodiment of the system, medical devices are identified through the scanning of barcodes present on the primary packaging of the medical device in question or medical devices are identified through the use of computer vision and machine learning algorithms. The cleaning-disinfecting system is able to positively identify the medical device in question and consume the medical device's lot number and other product-specific identification numbers and features in order to log the number of times that specific medical device has been used. In further embodiments of the cleaning-disinfecting system, the cleaning-disinfecting system is able to access a database stored in its firmware to alter the reprocessing cycle that is utilized by the system to match the material requirements of the specific kind of device that has been inserted into the cleaning-disinfecting system for reprocessing. Other embodiments of the cleaning-disinfecting system include mechanisms through which the cleaning-disinfecting system is able to detect the bioburden present on the medical device that is being reprocessed in real-time, both through direct analysis of the device's surface as well as through the analysis of extracted materials using rinse water and UV spectrophotometry, as an example.

In another embodiment of the system, usage data relating but not limited to time of use and usage frequency of medical devices may be stored in the cleaning-disinfecting system's on-board memory for transmission via Bluetooth, Wi-Fi, or wired data connections to the user's computer, the user's cellphone, to private HIPAA-compliant company servers, or to the user's physician's electronic health records system. This data may also be utilized to streamline the reordering process of medical devices or supplies on a monthly, quarterly, or otherwise regular basis, minimizing the need for direct user interaction to place these orders. In yet another embodiment of the cleaning-disinfecting system, this usage data may also facilitate the analysis of the user's online calendar connected to the cleaning-disinfecting system through user registration in order to book a medical visit through the user's registered physician's scheduling system for the renewal of prescriptions needed for the ordering of the medical device or supply in question. The cleaning-disinfecting system then issues an email, text, or push notification to the user's phone notifying them of the appointment. In yet another embodiment of the cleaning-disinfecting system, in lieu of directly making the appointment on the user's behalf, the cleaning-disinfecting system issues an email, text, or push notification to the user's phone that they need to schedule an appointment with their physician for the purposes of prescription renewal. In another embodiment of the cleaning-disinfecting system, the cleaning-disinfecting system issues a digital reminder to the physician to reorder or rewrite the user's prescription for the medical device that is reprocessed in the cleaning-disinfecting system. Preferably, the cleaning-disinfecting system provides the user with a survey or other data collection mechanism to ascertain whether or not any complications have arisen from the use of the medical device over the period for which the prescription is valid, and only sends the reminder to the physician if there have been minimal low-risk complications; otherwise the cleaning-disinfecting system schedules an appointment with the physician on the user's behalf or issues a push notification to the user in lieu of directly making an appointment.

In another embodiment, the RFID or NFC tag on the medical device may contain data that is gathered during use of the medical device when it is inserted or otherwise interfaces with the user or recipient of the medical device; in this embodiment, the cleaning-disinfecting system is able to download the data onto its on-board system memory for transmission via Bluetooth, Wi-Fi, or wired data connection in a HIPAA-compliant fashion. In various embodiments, this data transmission may be effected to the user's computer, the user's cellphone, to private HIPAA-compliant company servers, or to the user's physician's electronic health records system. In yet other embodiments of the system, the data that is transferred to its on-board system via RFID or NFC scanning may be analyzed by the cleaning-disinfecting system's firmware or algorithms that analyze data stored on private HIPAA-compliant company servers for early warning signs of disease using machine learning algorithms; following this analysis, the cleaning-disinfecting system may alert the user through its human-computer interface, through push notifications to the user's phone, through text messages, through electronic mail, or through some other form of electronically-mediated communication. In other embodiments of the cleaning-disinfecting system, the cleaning-disinfecting system may connect to the user's calendar and user's physician's scheduling system to automatically book an appointment for a check-up and detailed review of the data gathered by the medical device to facilitate early action and prevention of adverse medical outcomes.

In another embodiment, reprocessing fluids utilized in the system may include water, enzymatic cleaners, hydrogen peroxide, and lubricant and are pumped through the medical device or supply in a manner that exposes all surfaces of the medical device or supply that contact the user of that medical device or supply with sufficient duration as to render those surfaces clean, disinfected, and lubricious. Preferably, the systems and/or apparatuses can repeatedly reprocess medical devices and supplies without damaging them.

In various embodiments of the system, water used during the process is collected in a hard plastic reservoir, a flexible water bladder, or a detachable bottle. Preferably, the water used in the reprocessing cycle is tap water that is then pumped through a water filter with sufficiently small pores so as to filter out water-borne pathogens such as *Mycobacterium* spp. which are known to be present in the water supply. In other embodiments of the system, the water used is distilled water, deionized water, or purified water. In another embodiment of the cleaning-disinfecting system, the water which is fed into the system by the user is further treated with chemical buffers to alter the pH of the water to fall within the industry guidelines for critical water according to a pre-programmed process. In another embodiment of the cleaning-disinfecting system, the area of the system that facilitates the collection of water for reprocessing, whether a bladder, a reservoir, or other container, also analyzes the water for pH and dissolved minerals and compounds, and initiates an automated process of filtering or buffering the water using on-board reservoirs of materials so that the water falls within industry guidelines for critical water. Preferably, in various embodiments of the system, waste water from the process is collected in a hard plastic reservoir, a flexible water bladder, or a detachable bottle. In another embodiment of the system, the waste water is treated to reduce odor for discreet disposal in public areas such as restrooms.

In yet another embodiment, automated cleaning may be achieved through the use of an ultrasonic wave transducer that transmits ultrasonic waves, preferably in the 20-40 kHz range, to create cavitation bubbles that collapse with high energy and remove soils from the surfaces of medical devices or supplies. In another embodiment of the system, concentrated enzymatic cleaners are diluted with water and circulated through and around the medical devices and supplies for a period of time sufficient to remove soils from the surfaces of medical devices or supplies. During this circulation period, the system preferably uses a heating element to increase the temperature of the system fluids to approximately 40 degrees Celsius to maximize the efficacy of the enzymatic reaction. In another embodiment of the system, antimicrobial soap is circulated through the system to facilitate the automated cleaning of medical devices and supplies placed within the cleaning-disinfecting system.

In another embodiment, hydrogen peroxide may be utilized by the system to disinfect medical devices placed within the cleaning-disinfecting system. In various embodiments of the cleaning-disinfecting system, the cleaning-disinfecting system is compatible with a variety of high-level disinfectants or liquid chemical sterilants, including but not limited to Glutaraldehyde, Ortho-Phthaldehyde, Peracetic acid, Hydrogen peroxide, Hypochlorous acid, Hypochlorite, Chlorines, Iodophors, Phenols and Phenates. In other embodiments of the system, germicidal wavelengths of light, including but not limited to UV light, are utilized to disinfect or sterilize medical devices placed within the cleaning-disinfecting system. Ozone gas, steam, dry heat, and hot water pasteurization are utilized in embodiments of the cleaning-disinfecting system to disinfect or sterilize medical devices. In embodiments of the system, the system has the ability to utilize multiple disinfectants and sterilants to reprocess medical devices; the cleaning-disinfecting system can recognize the medical device placed within it for reprocessing, determine an optimal reprocessing endpoint for that medical device, and dynamically update process parameters to reach the endpoint. Similarly, the cleaning-disinfecting system can recognize the supply type that the user has placed within the cleaning-disinfecting system for reprocessing and automatically update process parameters to reflect the specific disinfection method chosen by the user. In a preferred embodiment of the system, the user is able to place concentrated disinfectants or sterilants into the cleaning-disinfecting system, which are diluted with water to a predetermined concentration for use in reprocessing medical devices through the use of dosing pumps or similar mechanism.

In an embodiment of the cleaning-disinfecting system, lubricant is applied to the medical device that is being reprocessed after the completion of the cleaning and disinfection stages of the reprocessing cycle using the primary pumping apparatus and fluid flow path in the cleaning-disinfecting system. In another embodiment of the cleaning-disinfecting system, a secondary syringe pump is utilized to apply lubricant to specific regions of the reprocessed medical device that are otherwise inaccessible using the primary fluid pathway. In another embodiment of the cleaning-disinfecting system, lubricant is first sterilized or disinfected using a UV diode with germicidal capabilities. In other embodiments of the system, users are able to configure how much lubricant is applied to the medical device to match their preference, or configure the system to mix additives into the lubricant that confer additional beneficial properties such as a germicidal property. Another embodiment of the system utilizes powdered lubricant and rehydrates it according to the manufacturer instructions prior to coating the medical device with it. In other embodiments of the system, lubricant is applied to the medical device by physically manipulating the medical device and advancing the portion of the medical device that needs to be lubricated into a lubricant reservoir; alternatively, the medical device itself features a fluid pathway that facilitates the deposition of lubricant in the appropriate area of the device. In another embodiment of the cleaning-disinfecting system, if the medical device is pre-coated, the cleaning-disinfecting system is capable of circulating the polymer substrate that coats the medical device throughout the closed-loop fluid pathway of the cleaning-disinfecting system prior to exposing the medical device to a polymerization agent that polymerizes the polymer substrate to the surface of the medical device, effectively re-coating the device. In a preferred embodiment of the system, the cleaning-disinfecting system circulates a polymer substrate that has lubricious or antimicrobial properties.

In preferred embodiments of the cleaning-disinfecting system, supplies used to reprocess medical devices are packaged together in a convenient format for storage, transportation, and use by the user of the reprocessor. These supplies may be packaged together in a single-use format where enough material is packaged for a single reprocessing cycle, packaged together in a daily-use format where enough material is packaged for a day's worth of reprocessing cycles, or packaged together in sufficient quantity to account for the full usable life of the medical device being reprocessed, depending on the medical device being reprocessed and typical frequency of use. These packages may feature flexible bladders or stiff compartments utilized in conjunction with one-way valves or water-tight and air-tight seals to prevent leakage or contamination during supply transport. These packages may also feature spring-loaded pistons that apply force to inject reprocessing suppliers into the closed-loop fluid pathway of the cleaning-disinfecting system.

In various embodiments of the cleaning-disinfecting system, each supply used in the system may be packaged separately from the others in a modular format, both for daily use and for single-use. Supplies may also be tagged with RFID or NFC tags so that the system can recognize the specific supplies being inserted into it for use in the reprocessing cycle. In another embodiment of the cleaning-disinfecting system, the cleaning-disinfecting system is able to receive and interface with a reusable secondary package that in turn accepts modular single- or multi-use supply packages in order to enable the user to reuse the secondary package and reduce the environmental footprint associated with use of the system. In yet another embodiment of the cleaning-disinfecting system, supplies are received on-board the cleaning-disinfecting system in reservoirs that are filled manually by the user. In one specific embodiment of the cleaning-disinfecting system, lubricant is stored in a static reservoir and is applied to the reprocessed medical device through a manual process wherein the user dips the medical device into the reservoir.

In other embodiments of the cleaning-disinfecting system, an on-board battery provides enough power to complete one reprocessing cycle, two reprocessing cycles, a day's worth of reprocessing cycles, or enough reprocessing cycles to account for the full usable lifespan of the medical device that is being reprocessed by the cleaning-disinfecting system. In various embodiments, this battery may be removable or permanently affixed to the cleaning-disinfecting system, and the cleaning-disinfecting system may have the ability to accept an external battery to supplement the on-board battery. In other embodiments, the cleaning-disinfecting system may be able to be charged with a wired connection, through wireless charging, through miniaturized solar panels, or through an on-board hand crank.

In a preferred embodiment of the cleaning-disinfecting system, the cleaning-disinfecting system features at least two distinct components that can be detached from one another to facilitate the transportation of the medical device that has been reprocessed in a manner that does not expose it to the external environment until it is ready to be used. The cleaning-disinfecting system may be configured so that hardware components such as displays, pumping mechanisms, batteries, on-board computers, filters, in-line water heaters, reprocessing supplies, or some combination thereof, are contained in a base unit, while the medical device and input and waste water bladders or reservoirs or some combination thereof are contained in a detachable carrying case unit so that the user has access to the device and the ability to refill the input water and drain the waste water from the previous cycle without the added bulk of the remainder of the system. Embodiments of the cleaning-disinfecting system may feature one-way valves in both the base and carrying case units to prevent leakage or seepage of liquids after the parts are detached from one another.

In another embodiment of the cleaning-disinfecting system, the medical devices that are reprocessed within it are sealed off from the external environmental through sterile packaging that is applied to and sealed around the medical device after the completion of a reprocessing cycle with the help of a separate supply of sterile packaging components and a heat sealer, allowing the user to remove the medical device and store or transport it without concerns of contamination of the device from external environments. This embodiment preferably includes a printer or other mechanism to indicate the duration for which the packaging will remain sterile, e.g. shelf life, to the user through on-package printing or labeling. In other embodiments of the system, the shelf life of the reprocessed medical device in its sterile packaging is transmitted to the user's smartphone or other device via text, push notification, or email, otherwise the shelf-life is obtainable through the cleaning-disinfecting system's human computer interface.

In a preferred embodiment of the cleaning-disinfecting system, it is mountable to a wheelchair frame via a stiff flange that slides onto the wheelchair frame. In other embodiments of the cleaning-disinfecting system, it is possible to temporarily mount the device to a wall or other vertical surface through the use of Velcro, suction, magnetic, static electric, microsuction tape, or adhesive attachment methods.

In preferred embodiments of the cleaning-disinfecting system, the cleaning-disinfecting system is configured to have a dedicated protective case that prevents damage to the cleaning-disinfecting system in case of accidental drops. In other embodiments of the cleaning-disinfecting system, this protective case contains compartments for additional supplies such as reprocessing supplies, back-up batteries, gloves, sterile pads, betadine, iodine wipes, hand sanitizer, or accessories intended to facilitate the use of the medical device in context such as urine drainage bags, extension tubes, catheter clamps, and tools for users with limited dexterity. In other embodiments of the system, both the base unit and the carrying case unit have a dedicated protective case that can be one case that is itself modular, detachable, and separable or can be two separate cases. In an embodiment of the cleaning-disinfecting system, accessories such as the ones mentioned above can form part of the closed-loop fluid pathway in the cleaning-disinfecting system so that they are cleaned or cleaned and disinfected/sterilized alongside the medical device.

In an embodiment of the cleaning-disinfecting system, the cleaning-disinfecting system may feature a human computer interface that communicates device status to users through the use of audiovisual cues. These audiovisual cues are communicated through a screen in a preferred embodiment; an embodiment of the cleaning-disinfecting system may feature a capacitive touch screen. These audiovisual cues are communicated through lights and piezo resistors or speakers in another embodiment of the cleaning-disinfecting system. Another embodiment of the cleaning-disinfecting system utilizes the user's cellphone to communicate device status information through texts, push notifications, or a mobile app that is synced to the cleaning-disinfecting system using Bluetooth or Wi-Fi.

In a preferred embodiment of the cleaning-disinfecting system, the medical device or supply being reprocessed in the system features channels in both the proximal and distal ends of the device to ensure that reprocessing fluids can circulate throughout the device and that all user-contacting surfaces of the device are reprocessed to the standards set out by the FDA. In another embodiment of the cleaning-disinfecting system, the medical device or supply being reprocessed in the system may contain flexible electronic sensors powered by a small on-board battery that gather diagnostic data during its use and save them onto the RFID/NFC chip on the medical device for later transfer to the handheld washer-disinfector when the device or supply is placed within the washer-disinfector. In another embodiment of the cleaning-disinfecting system, the medical device or supply in question is coated with a coating that has antimicrobial properties, to prevent the deposition or growth of pathogens on the surface of the medical device during use. In an embodiment of the cleaning-disinfecting system, this coating is attached to the medical device to preserve the user's ability to reuse it through cleaning and disinfection in the cleaning-disinfecting system after an extended period of time after initial use lasting for hours, days, or weeks.

In other embodiments of the cleaning-disinfecting system, the medical device may feature handles, flanges, and accessories that aim to make the process of using the medical device easier in context; these accessories may include mirrors with or without lights, spreaders used to manipulate the user's tissue and skin without directly contacting them, adjustable mechanisms that help create physical support or leverage as the medical device is being used in order to prevent accidental insertion or use of the device in a manner or into a bodily opening that the user did not intend. In another embodiment of the cleaning-disinfecting system, the medical device features caps at either end of the device to prevent the leakage of fluids from the medical device after it is removed from the cleaning-disinfecting system; preferably these caps are tethered to the medical device to prevent accidental loss of the caps. These caps may preferably feature one-way valves to allow for the flow of fluid through the caps during the reprocessing cycle, but not when the device is not being reprocessed. These caps may be connectable to the device through the use of magnets, living hinges, mechanical hinges, or other attachment mechanism. In a preferred embodiment, the medical device in question is a urinary intermittent catheter. In an embodiment of the cleaning-disinfecting system, the user can customize their medical device along predefined parameters such as length, material, flexibility, and accessories to better suit their individual needs.

The foregoing has outlined some of the aspects of the present cleaning-disinfecting system. These aspects should be construed strictly as illustrative of some of the more prominent features and applications of the cleaning-disinfecting system, rather than as limitations on the cleaning-disinfecting system.

Many other beneficial results can be obtained by modifying the embodiments within the scope of the cleaning-disinfecting system. Accordingly, for other objects and a full understanding of the embodiments, refer to the summary of the invention, the detailed description describing the preferred embodiment in addition to the scope of the embodiments defined by the claims and the accompanying drawings. The unique features characteristic of this cleaning-disinfecting system and operation will be understood more easily with the detailed description and drawings. It is to be understood that the drawings are for illustration and description only and do not define the limits of the invention.

Referring now to the Figures, there is shown a variety of embodiments of cleaning-disinfecting systems. Additionally, each of these variations may have a variety of optional equipment, components, and features associated therewith.

FIGS. 1-9E show various embodiments of a cleaning-disinfecting system 100 for a medical device. The medical device illustrated is a catheter 130. Other medical devices may be utilized with the cleaning-disinfecting system 100. The cleaning-disinfecting system 100 may be portable and battery-powered. As illustrated, the cleaning-disinfecting system 100 may include a reprocessor base 102 and a lid 104 that is able to open and close. The lid 104 may include an RFID scanner 160 for the medical device or catheter 130. The RFID scanner 160 may be located in other locations on the cleaning-disinfecting system 100.

Figure 20A:
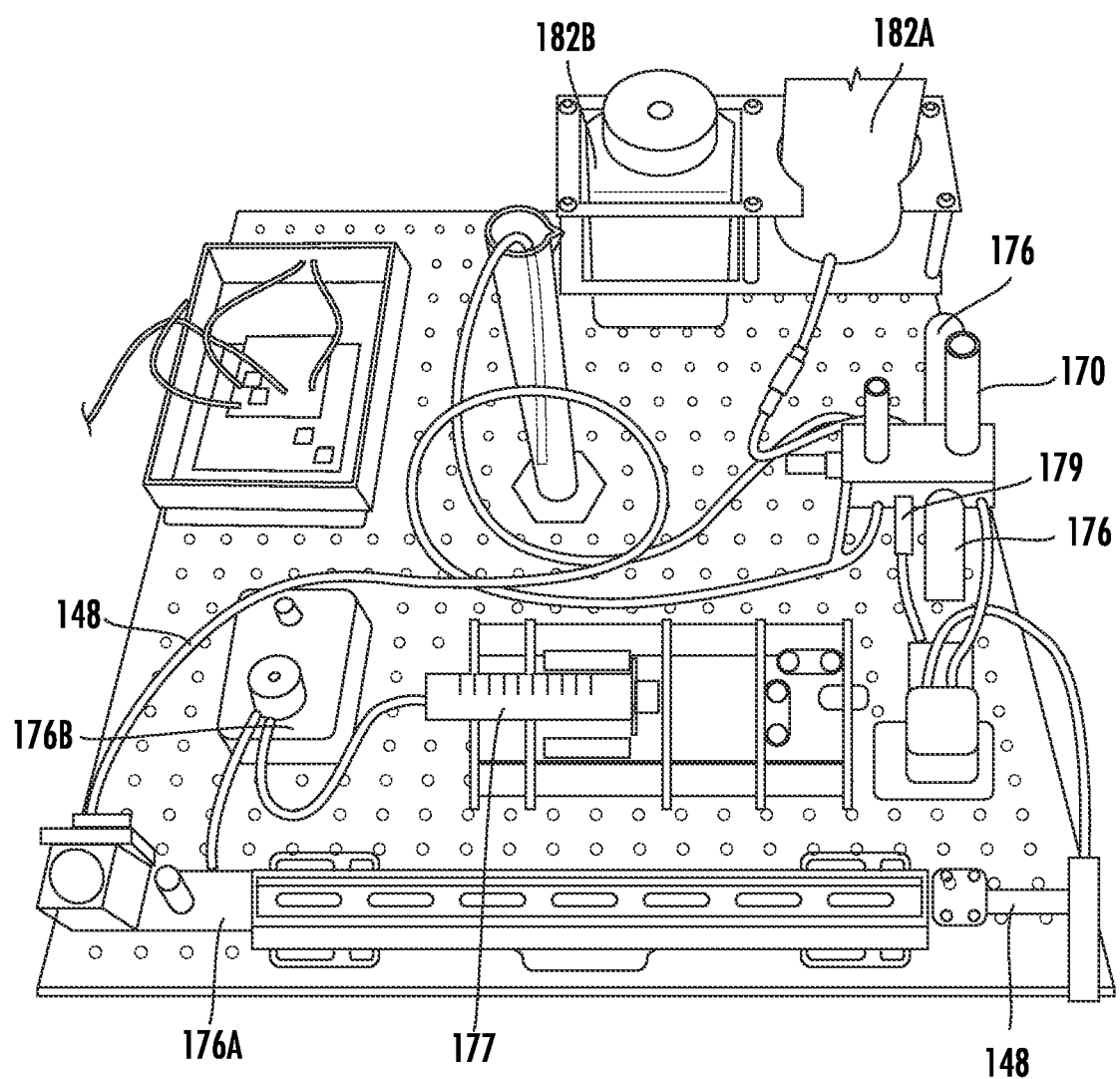
FIG. 20A is a perspective view of a cleaning-disinfecting system for a medical device according to one embodiment of the invention.
Figure 20C:
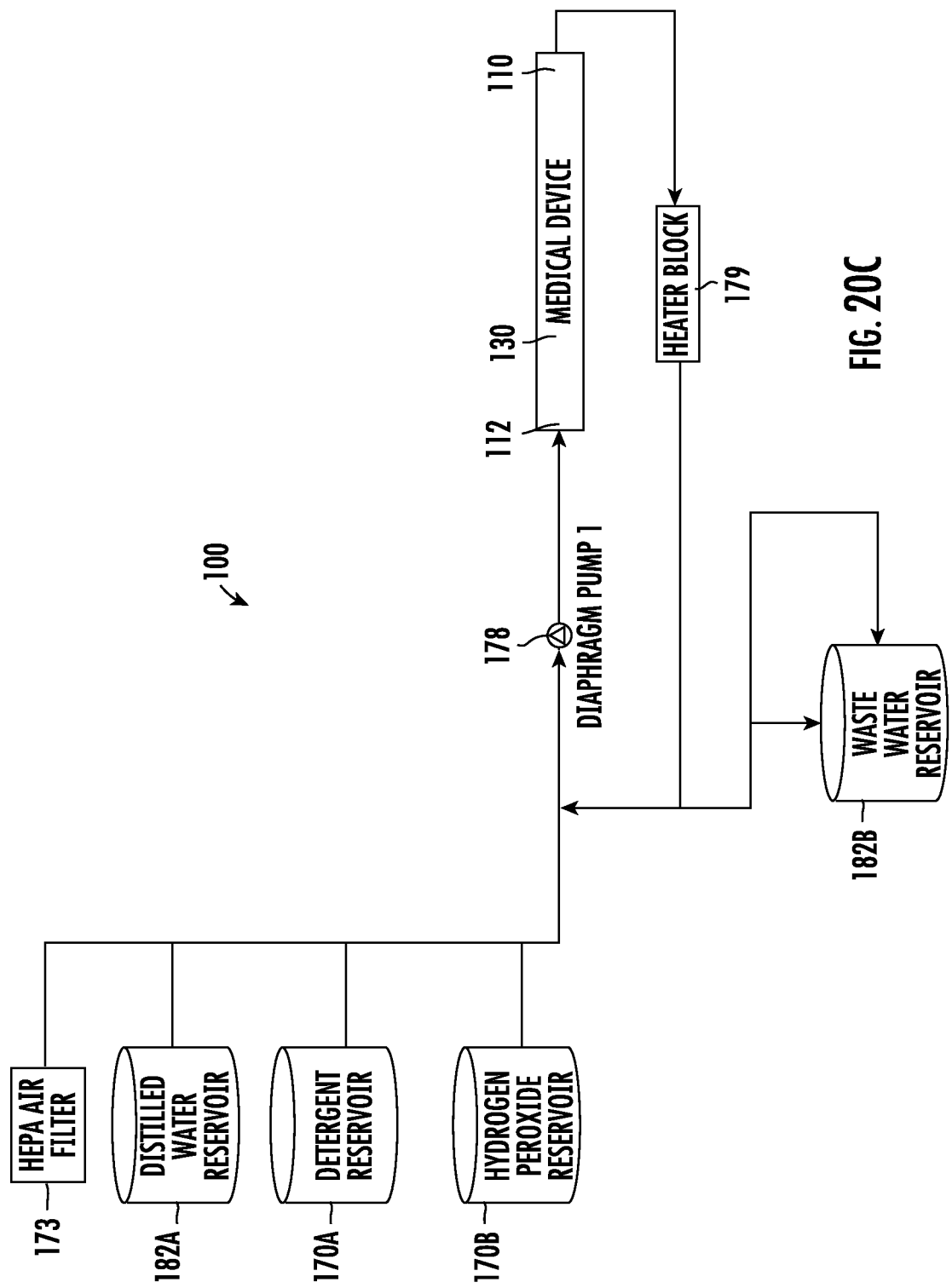
Figure 21A:
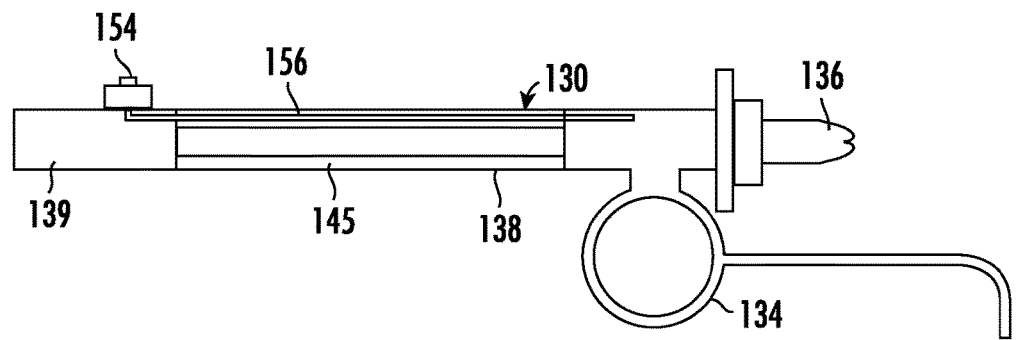
Figure 21B:
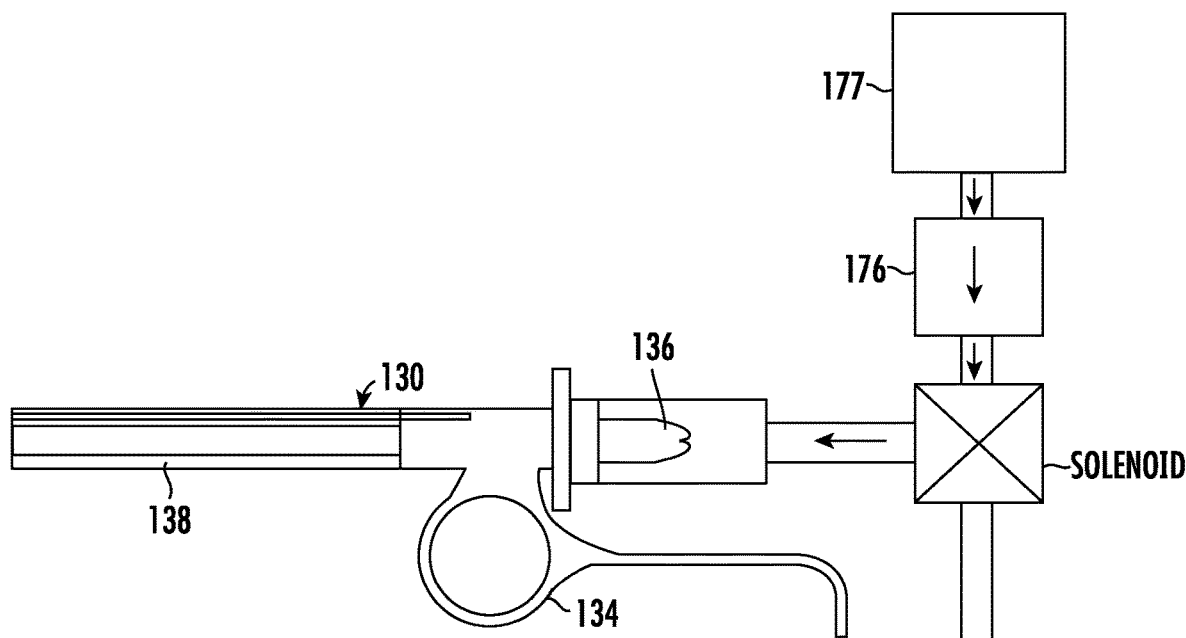

The cleaning-disinfecting system 100 may include a closed-loop fluid pathway 122 (shown in at least FIG. 20B) for cleaning and/or disinfecting the medical device/catheter 130. For example, a first end with the tip of the catheter 130 may connect to a catheter tip housing 110 and a second end of the catheter 130 may connect to a catheter funnel housing 112 to create the closed-loop fluid pathway 122. The catheter tip housing 110 and the catheter funnel housing 112 may include a flow connector that specifically connects to the ends of the catheter 130. The medical device/catheter 130 may sit in a mounting tray 114 within the reprocessor base 102. A water filter 180 and/or a cleaning supply reservoir 170 may be connected to and/or be a part of the closed-loop fluid pathway 122 for the cleaning/disinfecting system 100. The water filter 180 and cleaning supply reservoir 170 may be located within the reprocessor base 102.

The cleaning-disinfecting system 100 may also include a screen with a user interface 150. The screen/user interface 150 may be a human computer interface that communicates device status to users through the use of audiovisual cues. These audiovisual cues may be communicated through screen with a user interface 150 in a preferred embodiment. The screen with a user interface 150 may also a capacitive touch screen. These audiovisual cues may be communicated through lights and piezo resistors or speakers in another embodiment of the cleaning-disinfecting system 100. Another embodiment of the cleaning-disinfecting system 100 utilizes the user's cellphone to communicate device status information through texts, push notifications, or a mobile app that is synced to the cleaning-disinfecting system 100 using Bluetooth or Wi-Fi.

The cleaning-disinfecting system 100 may also include a start/stop/actuation button 152. The start/stop/actuation button 152 may include one or more button switches that are two-state depressible such that the start/stop/actuation button 152 is seated in a neutral position when untoggled and seats in a depressed position when toggled until the intended operation is completed or interrupted. (e.g., pressable buttons with locking states; depressed in one state; upright in the other).

Figure 2:
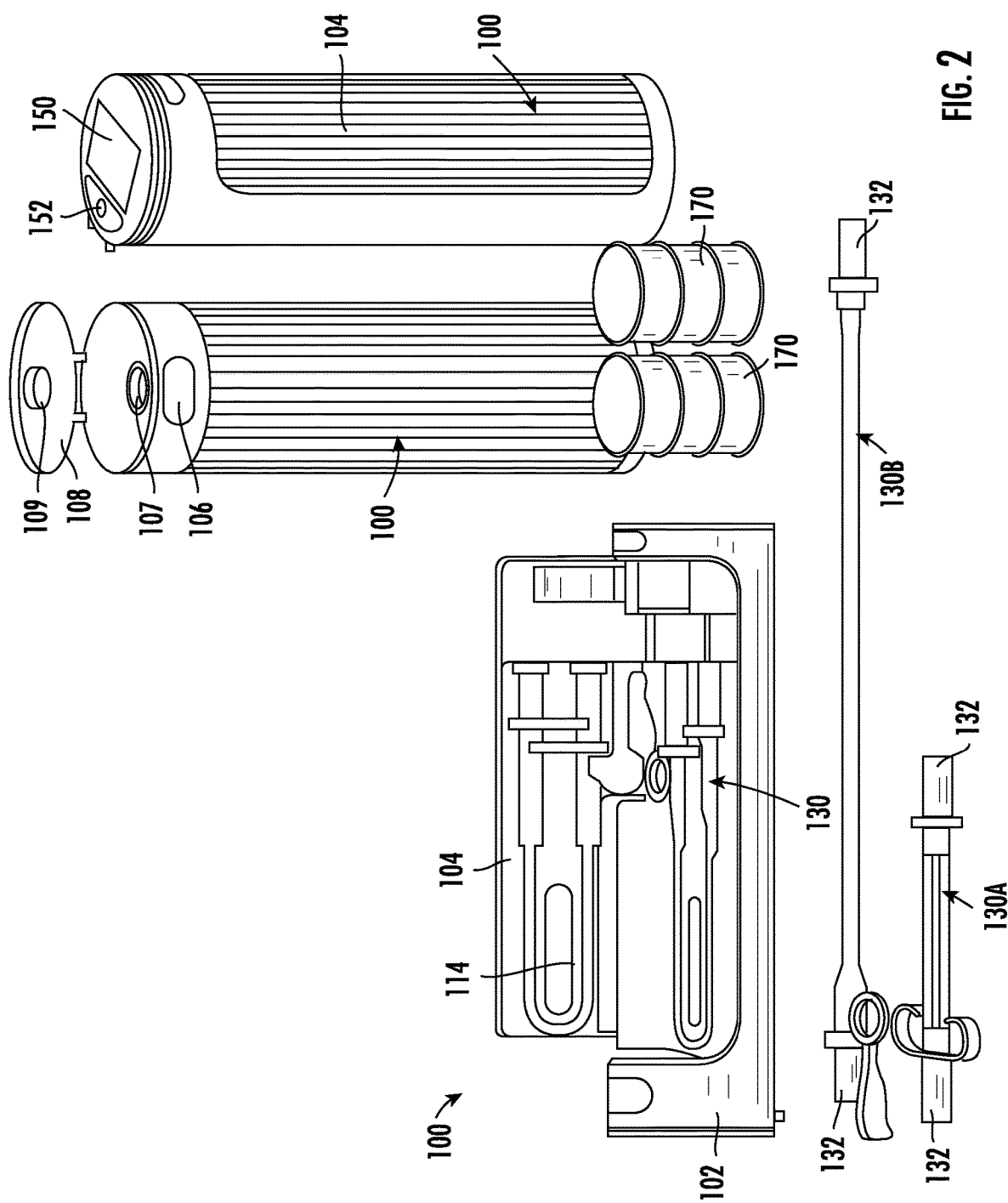
FIG. 2 is a perspective view of another illustrative embodiment of a cleaning-disinfecting system for a medical device according to one embodiment of the invention.

The cleaning-disinfecting system 100 illustrated in FIG. 2 is circular-shaped with a filling lid 108 and an opening 107. The filling lid 108 may include a sealing device 109 for the opening 107 such as a gasket or an O-ring to prevent leakage of environmental fluids from contaminating the medical device. The filling lid 108 may also include an open button 106 to open and release the filling lid 108. The opening 107 may be utilized to fill the cleaning-disinfecting system 100 with water directly through the water filter 180. The opening 107 may also be utilized to fill a water reservoir 180 with water.

FIG. 2 also illustrates a female catheter 130A and a male catheter 130B. The female catheter 130A and the male catheter 130B may include one or more removable catheter caps 132. The caps 132 may be located at either end of the medical device to prevent the leakage of fluids from the medical device after it is removed from the cleaning-disinfecting system 100. The caps 132 may be tethered to the medical device to prevent accidental loss of the caps 132. The caps 132 may include one-way valves to allow for the flow of fluid through the caps 132 during the reprocessing cycle, but not when the medical device is not being reprocessed. The caps 132 may be connectable to the medical device through the use of magnets, living hinges, mechanical hinges, or other attachment mechanisms.

In embodiments of the cleaning-disinfecting system 100, the cleaning-disinfecting system 100 may include at least two distinct components that can be detached from one another to facilitate the transportation of the medical device that has been reprocessed in a manner that does not expose it to the external environment until it is ready to be used, as illustrated in at least FIGS. 3A-B, 4A-C, and 5.

Figure 3A:
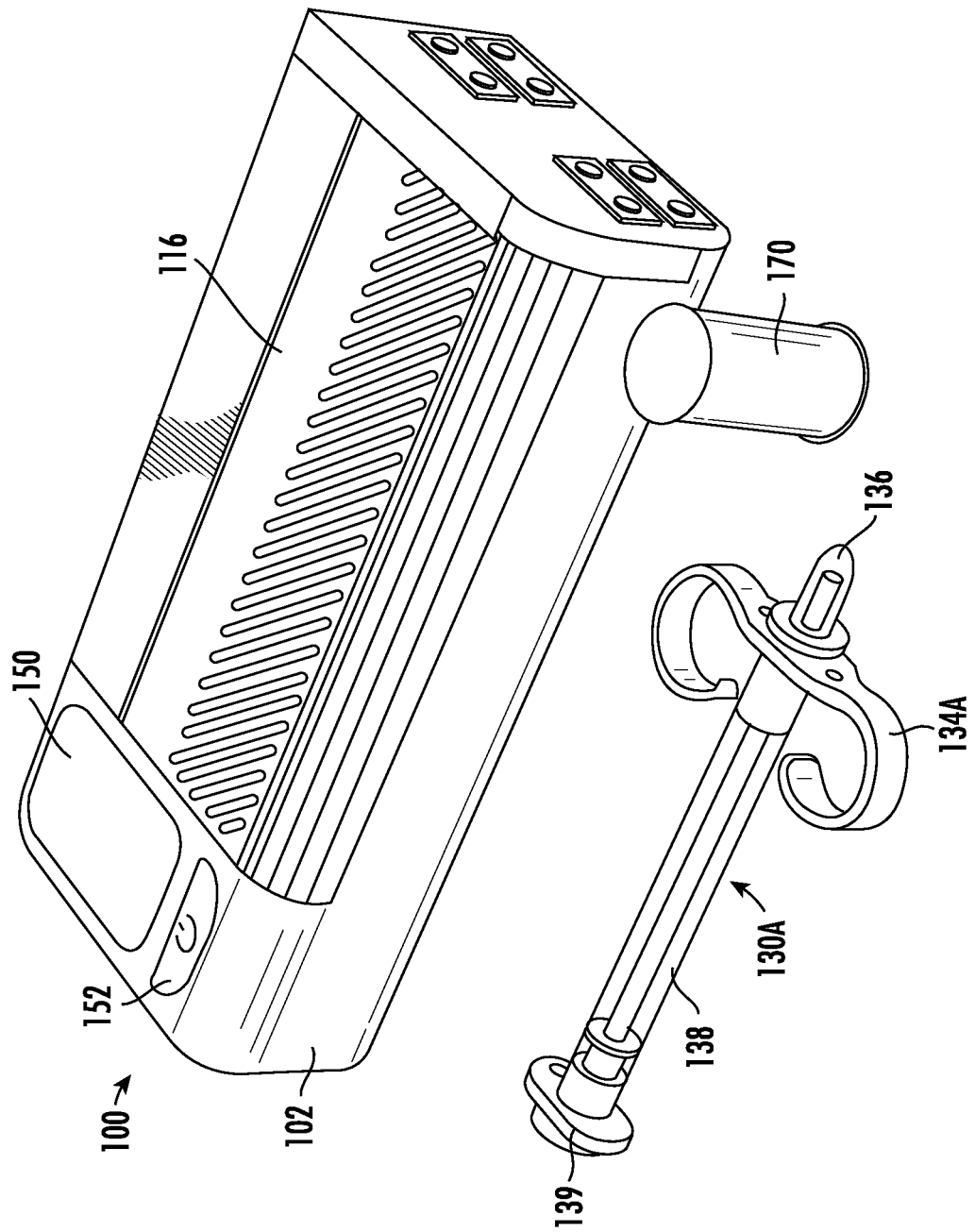
FIGS. 3A and 3B are perspective views of another illustrative embodiment of a cleaning-disinfecting system for a medical device according to one embodiment of the invention.
Figure 3B:
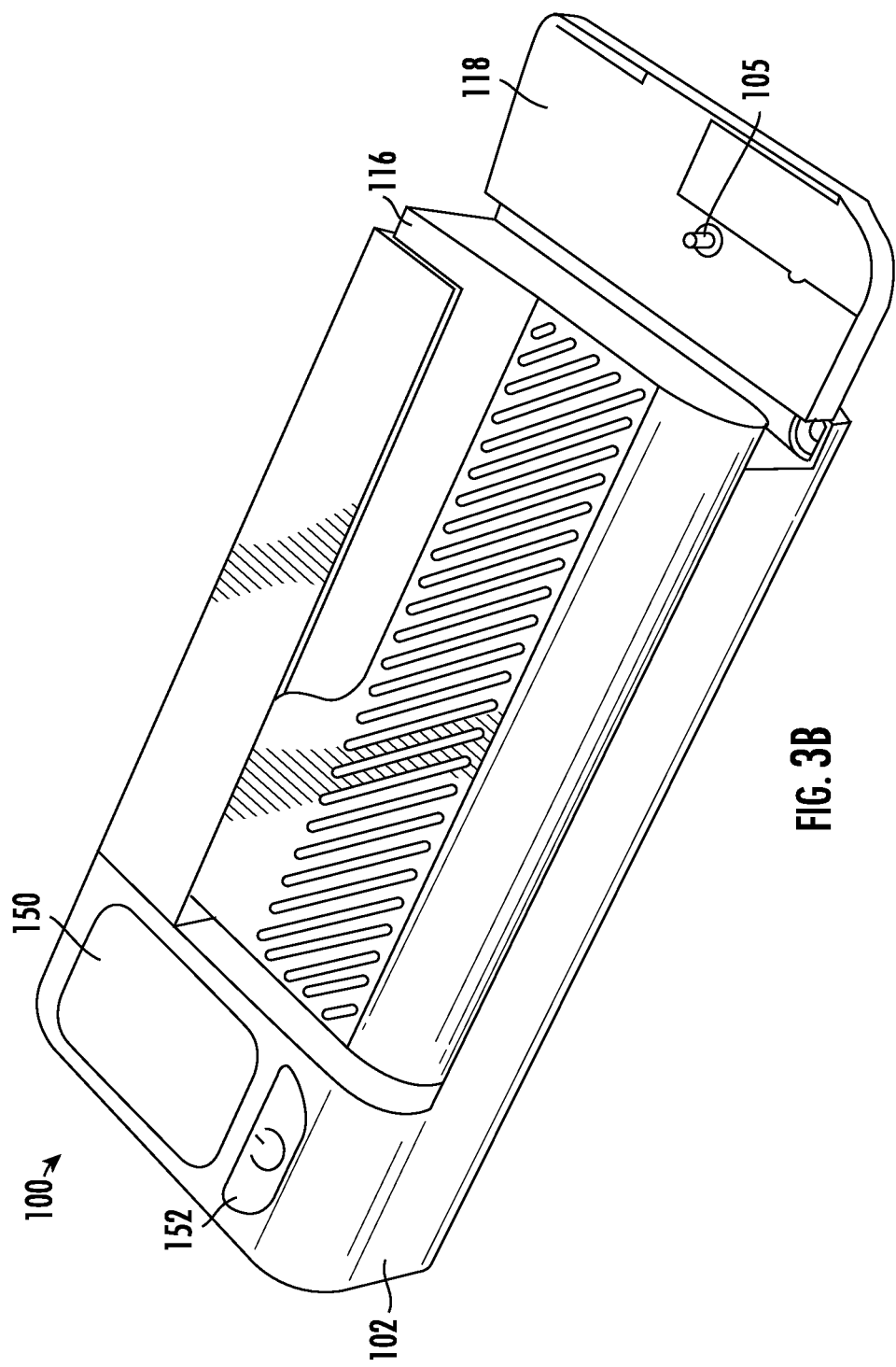

FIGS. 3A and 3B illustrate a cleaning-disinfecting system 100 with a removable catheter carrying case 116 and a reprocessor base 102. FIGS. 4A-C, 5, and 9A-E also illustrate a removable catheter carrying case 116 with a reprocessor base 102. The removable and detachable carrying case 116 may provide the user access to the medical device and the ability to refill the input water and drain the waste water from the previous cycle without the added bulk of the remainder of the system. Embodiments of the cleaning-disinfecting system 100 may feature one-way valves in both the reprocessor base 102 and removable catheter carrying case 116 to prevent leakage or seepage of liquids after the parts are detached from one another. A protective case may prevent damage to the cleaning-disinfecting system 100 in case of accidental drops.

Figure 4A:
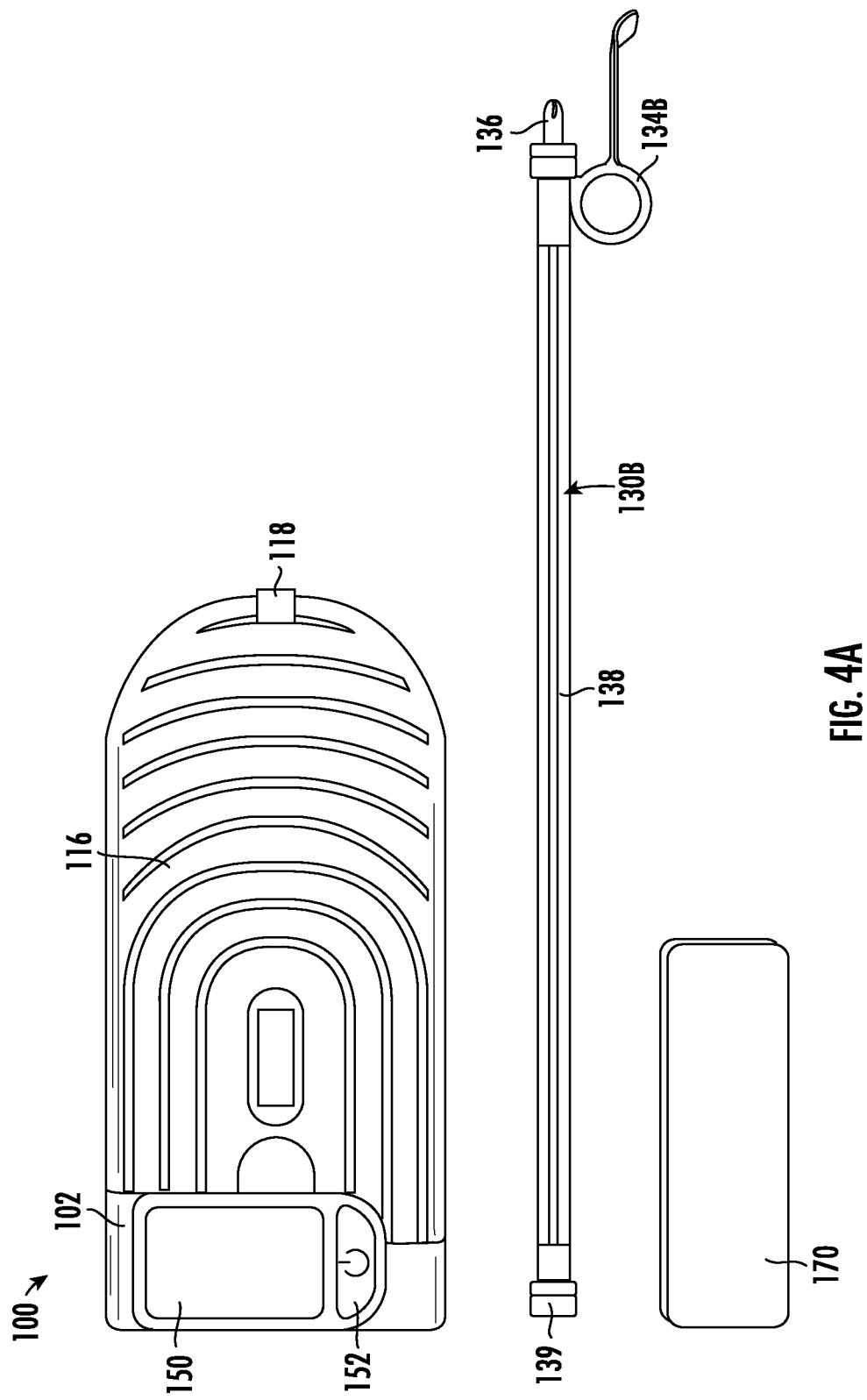
FIGS. 4A-4C are perspective views of another illustrative embodiment of a cleaning-disinfecting system for a medical device according to one embodiment of the invention.
Figure 4B:
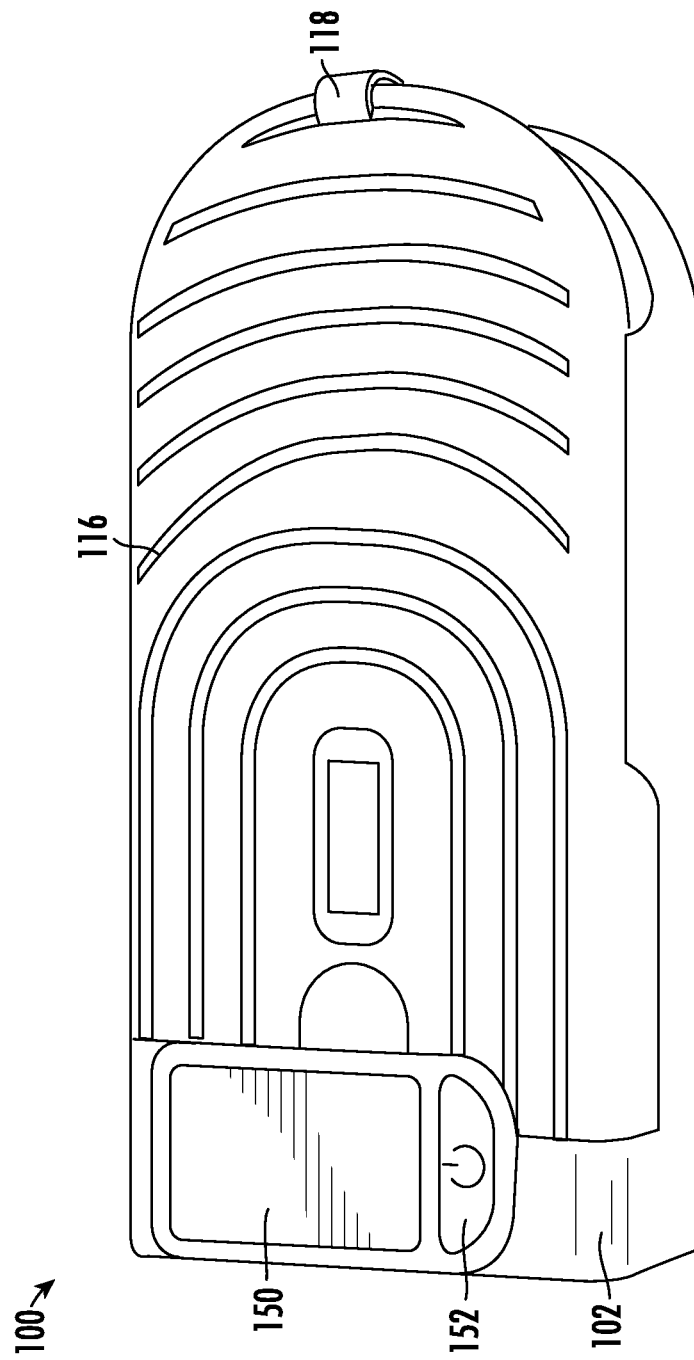

FIG. 3A illustrates a female catheter 130A that may be utilized and reprocessed within the cleaning-disinfecting system 100. The female catheter 130A may include a female insertion aid 134A, an introducer tip 136, an insertion sleeve 138, and a catheter funnel 139. FIG. 4A illustrates a male catheter 130B that may be utilized and reprocessed within the cleaning-disinfecting system 100. The male catheter 130B may include a male insertion aid 134B, an introducer tip 136, an insertion sleeve 138, and a catheter funnel 139.

The carrying case 116 illustrated in FIGS. 3B, 4A-C, and 5 illustrate a carrying case latch 118 that may be used to open and close the carrying case 116. In other embodiments of the cleaning-disinfecting system 100, the carrying case 116 may contain compartments for additional supplies such as reprocessing supplies, back-up batteries, gloves, sterile pads, betadine, iodine wipes, hand sanitizer, or accessories intended to facilitate the use of the medical device in context such as urine drainage bags, extension tubes, catheter clamps, and tools for users with limited dexterity. In other embodiments of the cleaning-disinfecting system 100, both the carrying case 116 with a reprocessor base 102 may have a dedicated protective case that can be modular, detachable, and separable or can be two separate protective cases. In an embodiment of the cleaning-disinfecting system 100, accessories such as urine drainage bags, extension tubes, catheter clamps, and tools may form part of the closed-loop fluid pathway 122 in the cleaning-disinfecting system 100 so that the accessories are cleaned or cleaned and disinfected/sterilized alongside the medical device.

Figure 4C:
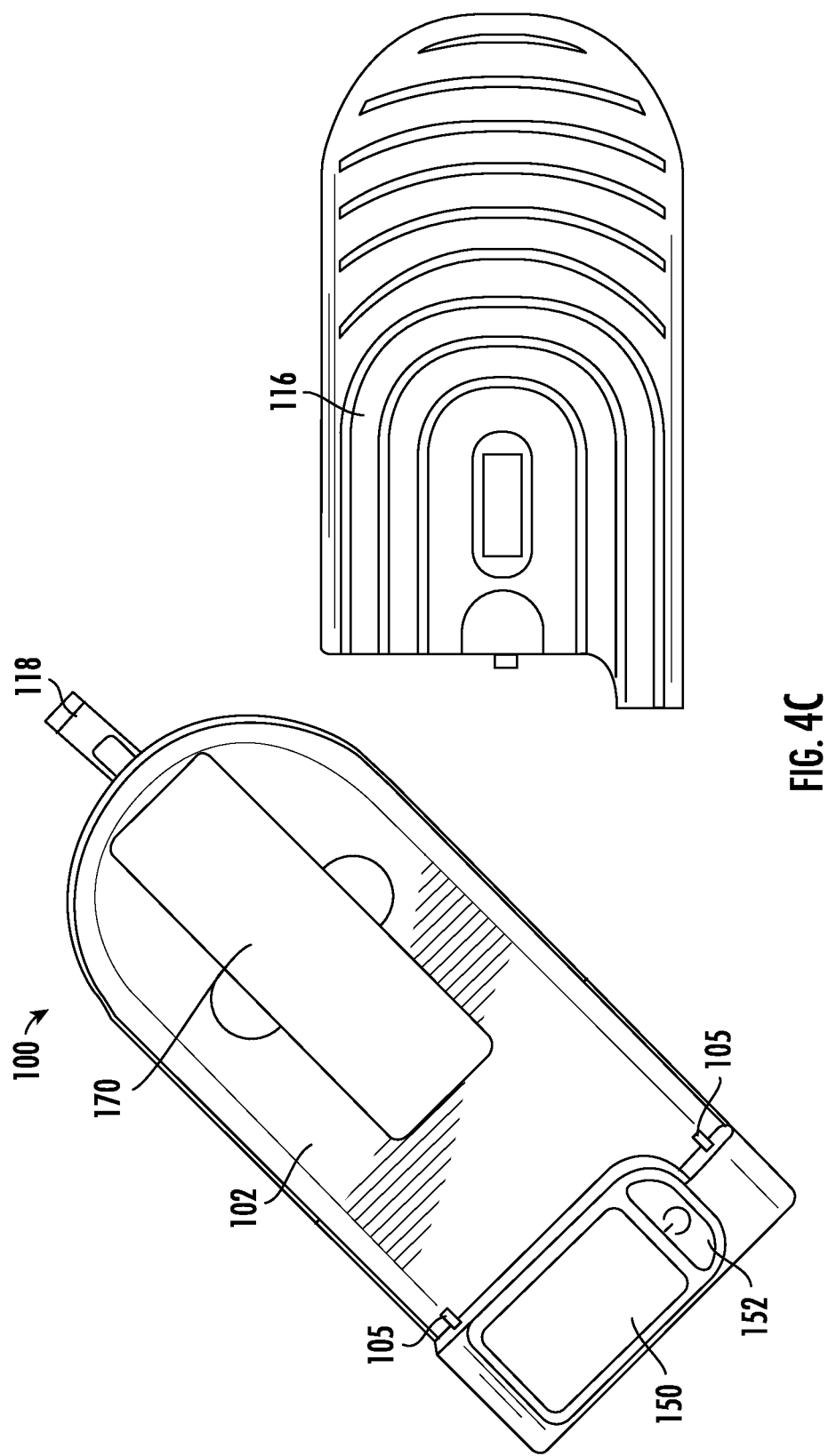

Further, as illustrated in FIGS. 3B and 4C, the reprocessor base 102 may include one or more ports 105. The one or more ports 105 may be male connections or female connections that include a valve. The valve and connections of the one or more ports 105 may provide an air-tight and water-tight valve connection with the medical device or the catheter 130 to prevent leakage or contamination during supply transport. The one or more ports 105 may include one-way valves in both the reprocessor base 102 and/or carrying case 116 to prevent leakage or seepage of liquids after the parts are detached from one another.

Figure 5A:
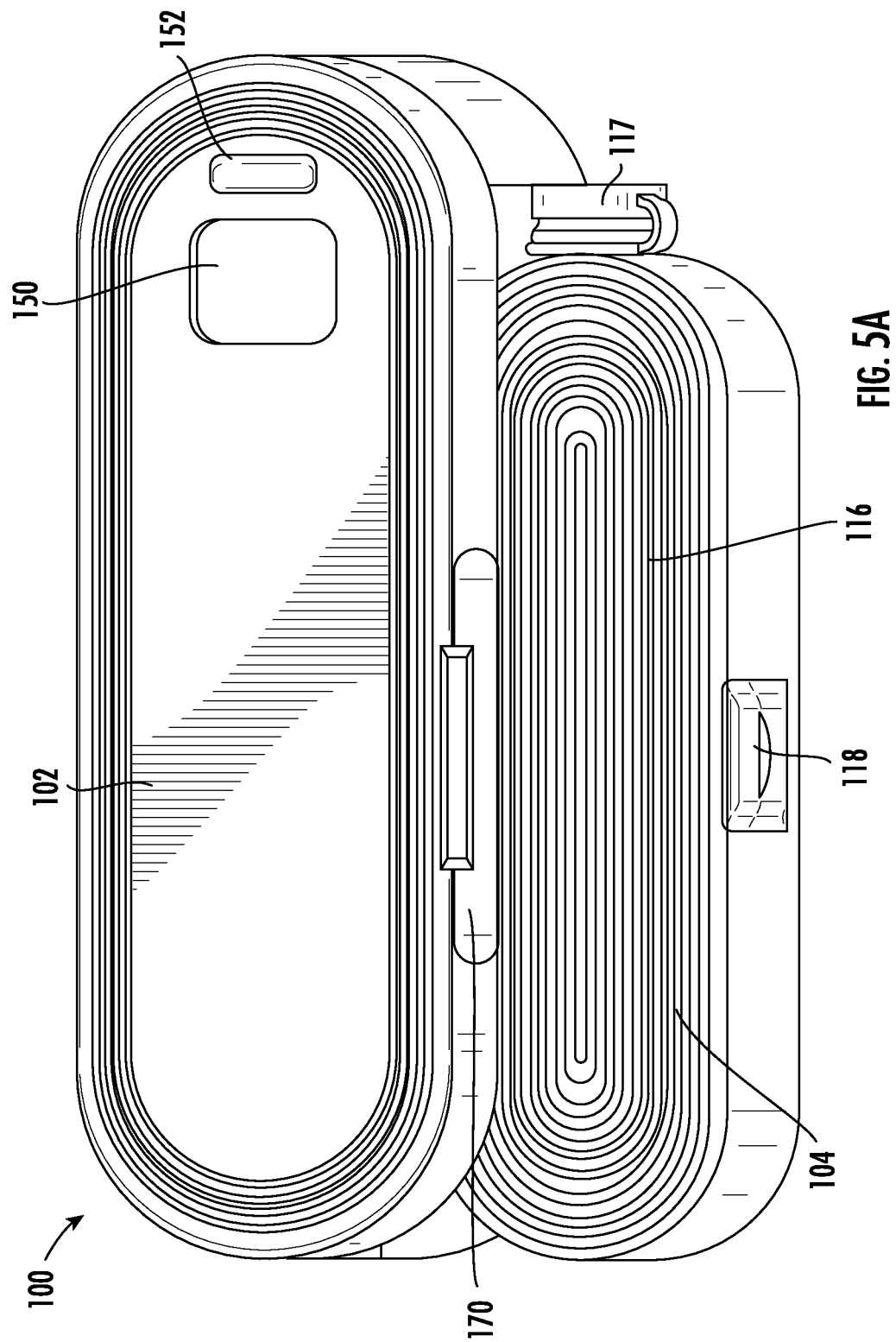
FIGS. 5A and 5B are perspective views of another illustrative embodiment of a cleaning-disinfecting system for a medical device according to one embodiment of the invention.
Figure 5B:
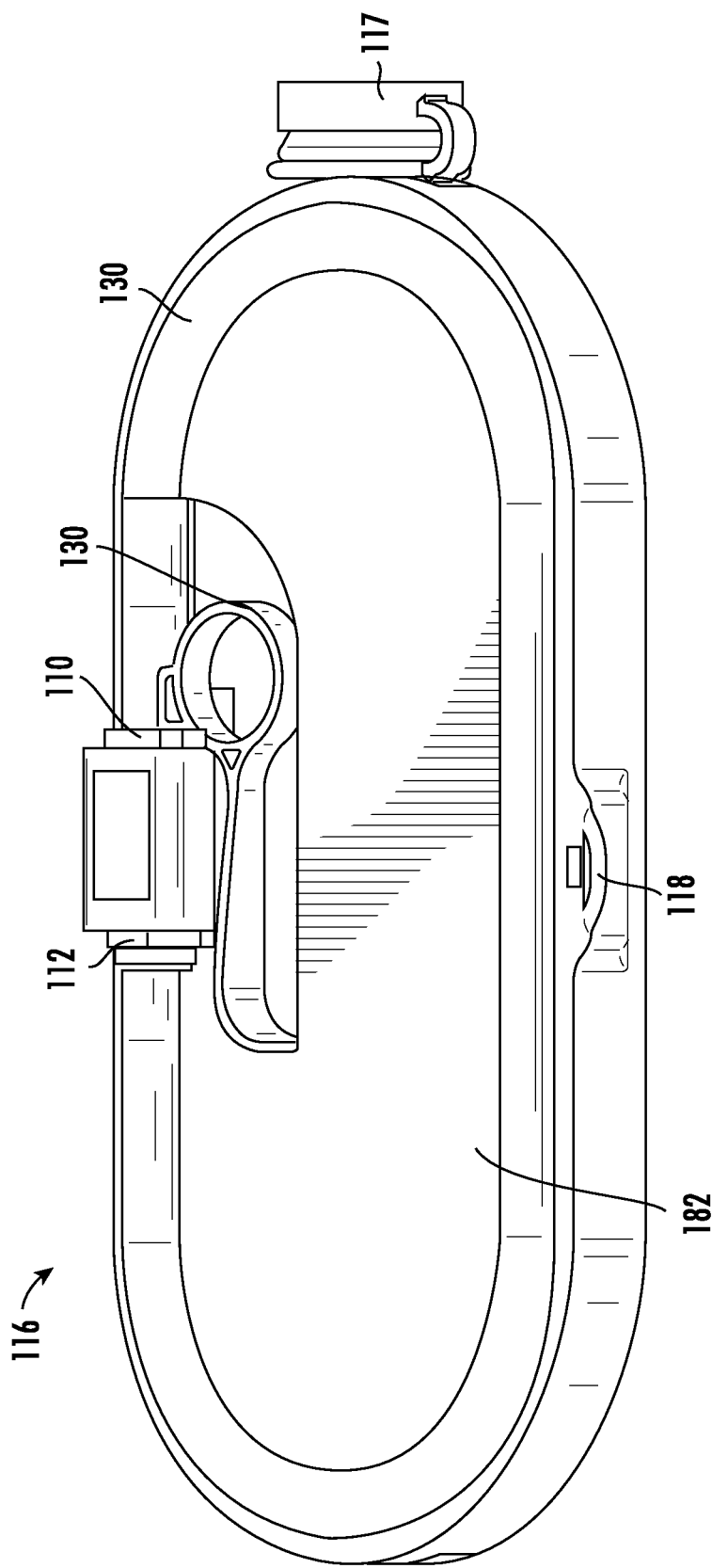

FIGS. 5A and 5B illustrate a cleaning-disinfecting system 100 with a removable catheter carrying case 116 adjacent to the reprocessor base 102. The removable catheter carrying case 116 may include a carrying case water inlet 117 to fill water. Additionally, the cleaning-disinfecting system 100 includes a cleaning supply reservoir 170 located between the removable catheter carrying case 116 and the reprocessor base 102. As illustrated in FIG. 5B, the removable catheter carrying case 116 may include a catheter tip housing 110 and a catheter funnel housing 112. A first end with the tip of the catheter 130 may connect to the catheter tip housing 110 and specifically to a flow connector on the catheter tip housing 110. A second end of the catheter 130 may connect to the catheter funnel housing 112 and specifically to a flow connector on the catheter funnel housing 112. Further as illustrated in FIG. 5B, the catheter carrying case 116 may include a water reservoir 182 (lid 104 not shown in FIG. 5B). The water reservoir 182 may include one or more flexible water bladders, such as a clean water flexible water bladder 183 and/or a dirty water flexible water bladder 184.

Figure 6:
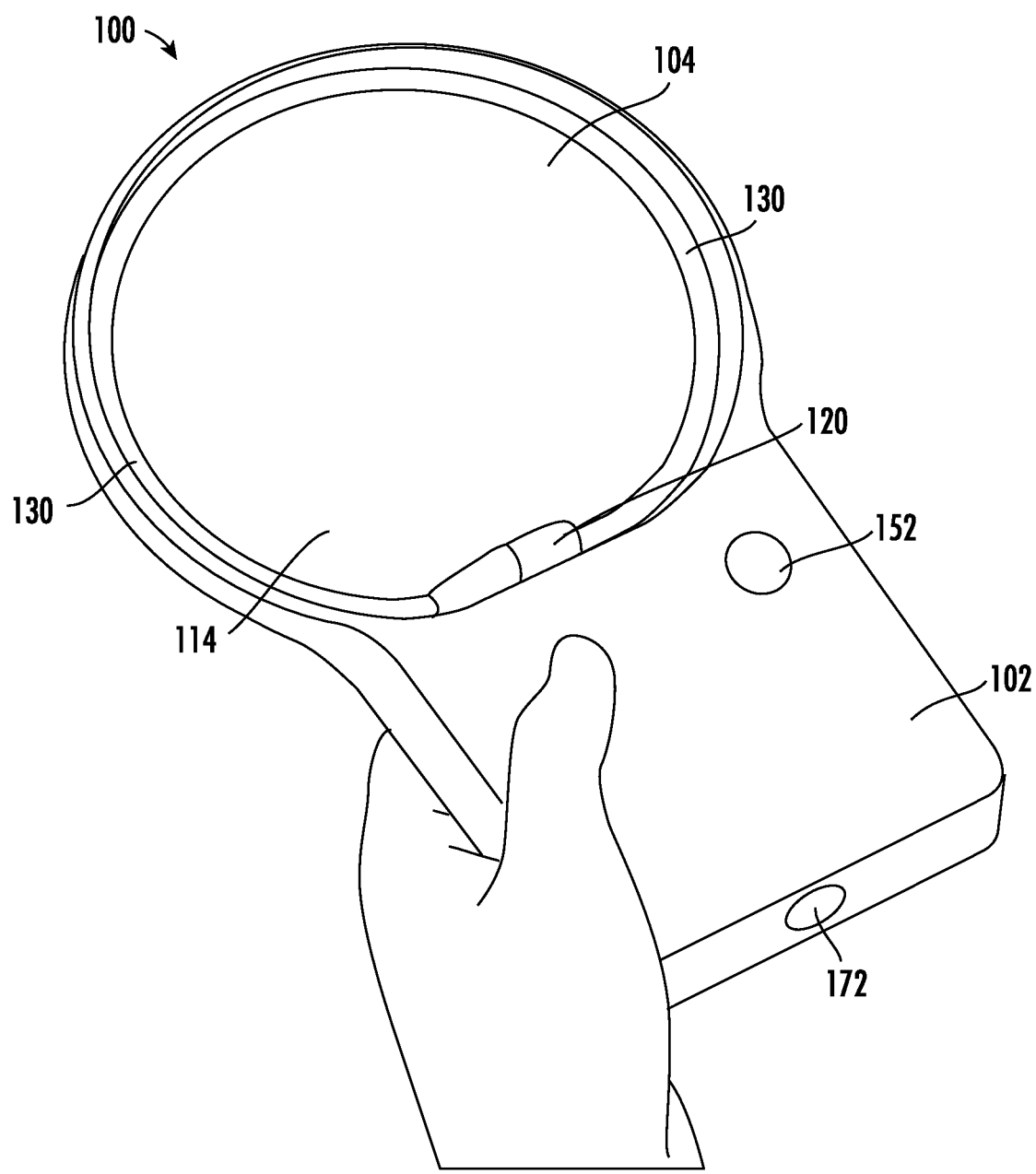
FIG. 6 is a perspective view of another illustrative embodiment of a cleaning-disinfecting system for a medical device according to one embodiment of the invention.

FIG. 6 illustrates another embodiment of a cleaning-disinfecting system 100 that includes a reprocessor base 102 with a lid 104 and an actuation button 152. The cleaning-disinfecting system 100 may also include a circular tray 114 to hold a medical device, such as a catheter 130. The reprocessor base 102 may also include a catheter mounting port 120 to mount each of the ends of the catheter 130 to the reprocessor base 102. Further, the cleaning-disinfecting system 100 as illustrated in FIG. 6 may include a cleaning supply inlet 172 that may be in-line with the cleaning supply reservoir 170.

Figure 7A:
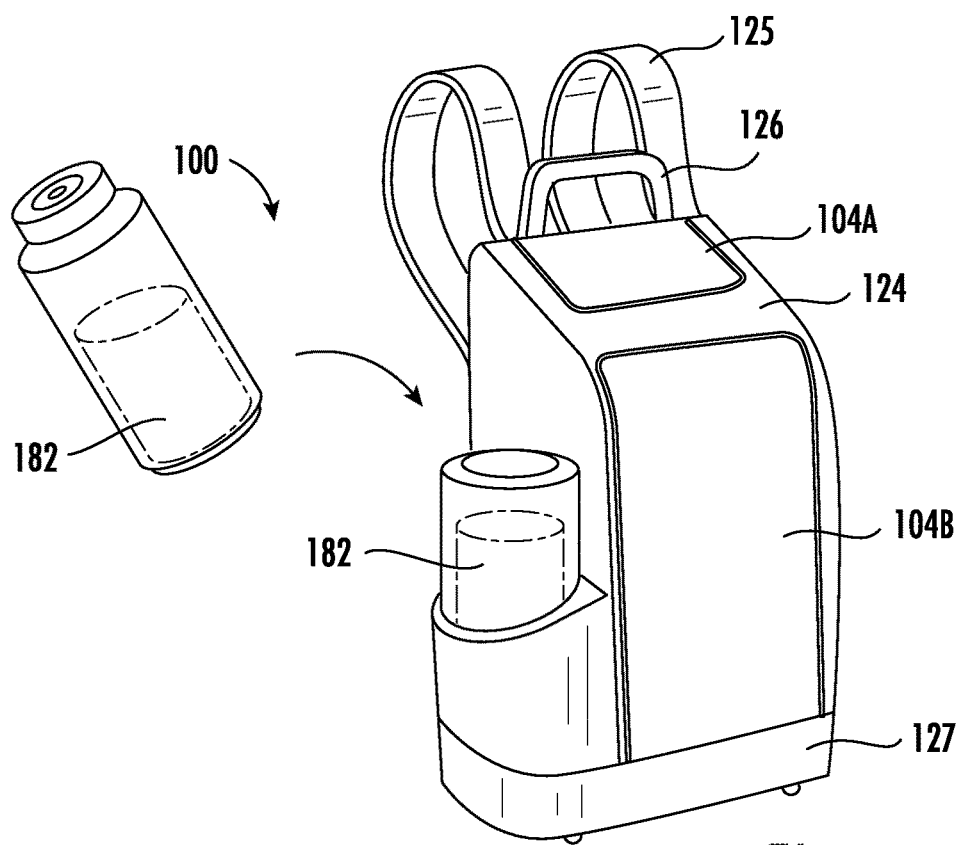
FIGS. 7A and 7B are perspective views of another illustrative embodiment of a cleaning-disinfecting system for a medical device according to one embodiment of the invention.
Figure 7B:
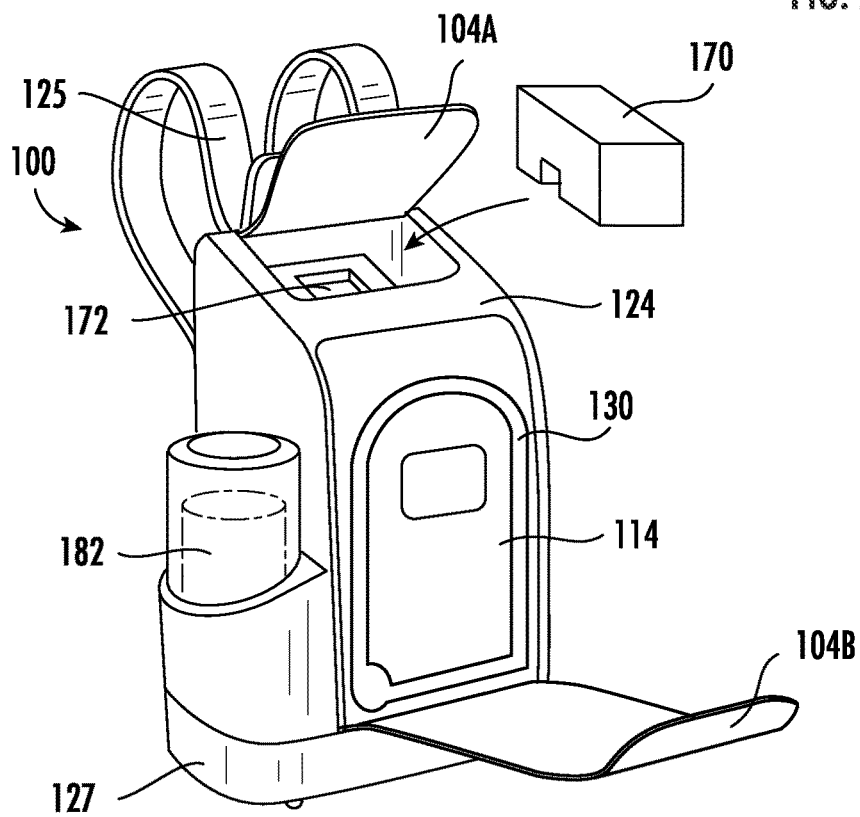

In various embodiments of the cleaning-disinfecting system 100, water used during the process may be collected in a hard plastic reservoir, a flexible water bladder, or a detachable bottle, specifically as illustrated in FIGS. 7A, 7B, 8A-D, 9A-E, and 10A-B. FIGS. 7A and 7B illustrate a cleaning-disinfecting system 100 with an integrated bulk reprocessor design. The cleaning-disinfecting system 100 may comprise a container 124 (e.g., bag, carrier, case, backpack) and the cleaning-disinfecting system 100 (including components) can be enclosed in the container 124. Preferably, the container 124 can be carried by a patient. Preferably, the largest dimension of the container 124 may be less than two feet and weight less than ten pounds. The container 124 may include straps 125 and/or a hook 126 to hang the container 124 and the cleaning-disinfecting system 100. The container 124 may include a rigid bottom 127 for easy wipe down. The container 124 may include one or more removable water reservoirs 182. Additionally, as illustrated in FIG. 7B, the cleaning-disinfecting system 100 includes one or more lids 104. A first lid 104A may open for access to a cleaning supply inlet 172. The cleaning supply inlet 172 may be utilized for the insertion of daily cleaning supplies 170 which may be in the form of a chemical cup or chemical pack that can be utilized for one or more reprocessing cycles. A second lid 104B may open for access to the medical device mounting tray 114 and the medical device or catheter 130.

Figure 8A:
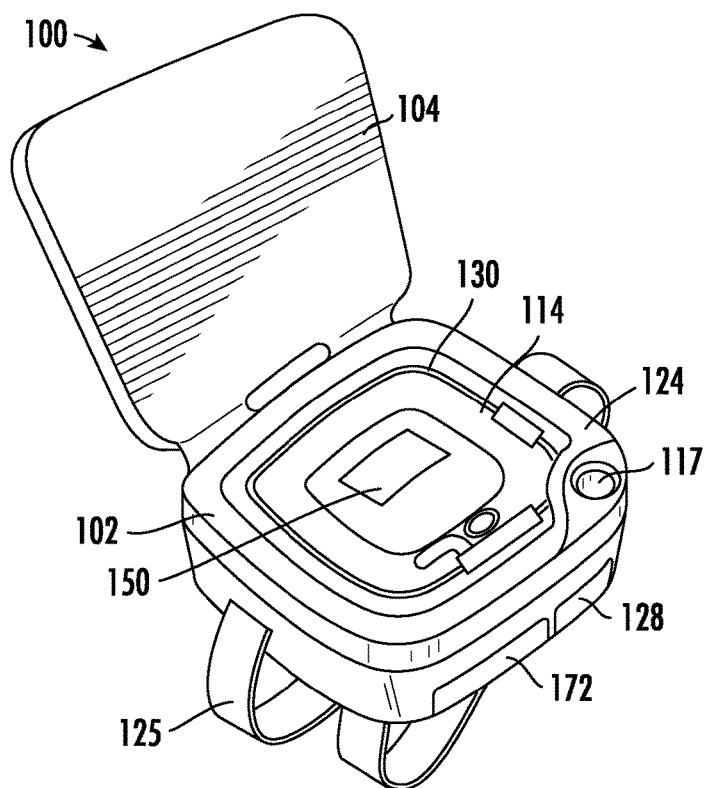
FIGS. 8A-8D are various views of another illustrative embodiment of a cleaning-disinfecting system for a medical device according to one embodiment of the invention.
Figure 8B:
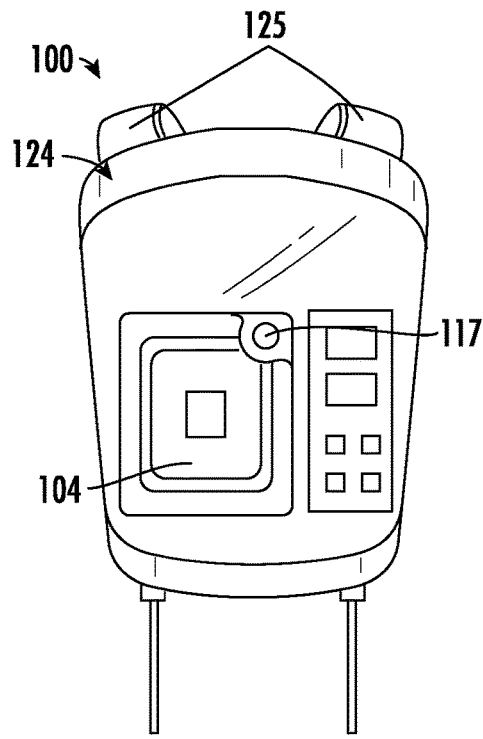
Figure 8C:
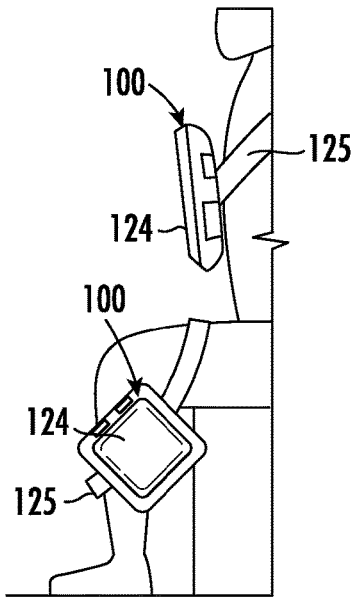
Figure 8D:
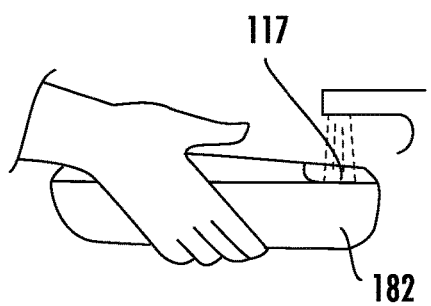

FIGS. 8A-D illustrate another embodiment of a cleaning-disinfecting system 100 providing container 124 (e.g., bag, carrier, case, backpack) with a flexible strapping system 125. As illustrated in FIG. 8B, the strapping system 125 may be utilized to strap the cleaning-disinfecting system 100 along the torso or legs of a patient. The cleaning-disinfecting system 100 includes a reprocessing base 102 with a lid 104. The lid 104 may provide access to the medical device mounting area and a medical device mounting tray 114 for the medical device or catheter 130. Further, the cleaning-disinfecting system 100 may include a water inlet 117. As illustrated in FIG. 8D, the cleaning-disinfecting system 100 and/or a water reservoir 182 may be directly filled with water through the water inlet 117 from a faucet or other water source. The cleaning-disinfecting system 100 may also include a cleaning supply inlet 172 positioned along the side of the reprocessing base 102 and the cleaning supply inlet 172 may be in-line with a cleaning supply reservoir 170.

Additionally, as illustrated in FIG. 8A, the cleaning-disinfecting system 100 may include an on-board battery 128. All of the embodiments of the cleaning-disinfecting system 100 may include an on-board battery 128. The on-board battery 128 may be rechargeable and/or removable. The on-board battery 128 may provide enough power to complete one reprocessing cycle, two reprocessing cycles, a day's worth of reprocessing cycles, or enough reprocessing cycles to account for the full usable lifespan of the medical device that is being reprocessed by the cleaning-disinfecting system. In various embodiments, the on-board battery 128 may be removable or permanently affixed to the cleaning-disinfecting system, and the cleaning-disinfecting system may have the ability to accept an external battery to supplement the on-board battery 128. In other embodiments, the cleaning-disinfecting system 100 may be able to be charged with a wired connection, through wireless charging, through miniaturized solar panels, or through an on-board hand crank. Additionally, charging of the on-board battery 128 may be facilitated through wireless charging interfaces.

FIGS. 9A-E illustrate another embodiment of a cleaning-disinfecting system 100 with a reprocessor base 102 a removable catheter case 116. The removable catheter case 116 may fit within a portion of the reprocessor base 102. The removable catheter case 116 may include a handle 115. The removable and detachable carrying case 116 may provide the user access to the medical device and the ability to refill the input water and drain the waste water from the previous cycle without the added bulk of the remainder of the system. Embodiments of the cleaning-disinfecting system 100 may feature one-way valves in both the reprocessor base 102 and removable catheter carrying case 116 to prevent leakage or seepage of liquids after the parts are detached from one another. The protective case may prevent damage to the cleaning-disinfecting system 100 in case of accidental drops. The reprocessing base 102 may include a cleaning supply inlet 172. The cleaning supply inlet 172 may be utilized for the insertion of daily cleaning supplies 170 which may be in the form of a chemical cup or chemical pack that can be utilized for one or more reprocessing cycles.

Figure 9A:
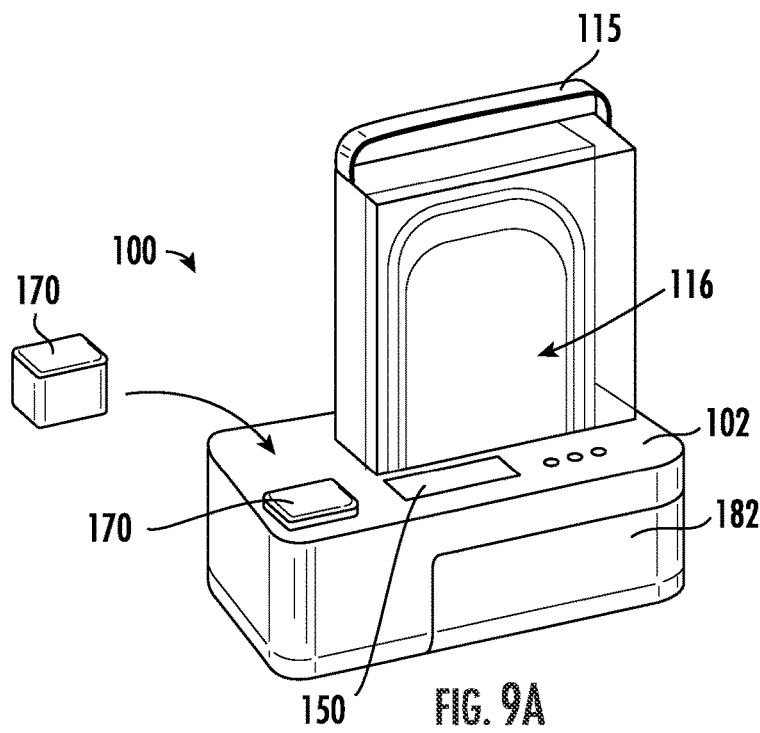
FIGS. 9A-9E are various views of another illustrative embodiment of a cleaning-disinfecting system for a medical device according to one embodiment of the invention.
Figure 9B:
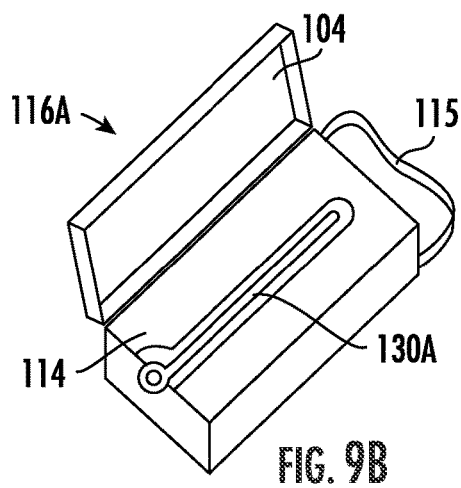
Figure 9C:
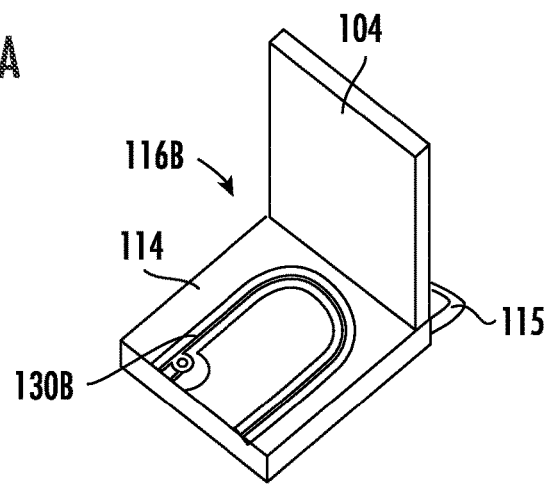

FIGS. 9B and 9C illustrate the removable catheter case 116, with FIG. 9B showing a female catheter case 116A and FIG. 9C showing a male catheter case 116B. The catheter case 116A, 116B include a lid 104 that provides access to the medical device mounting area and a medical device mounting tray 114 for the medical device or catheter 130.

Figure 9D:
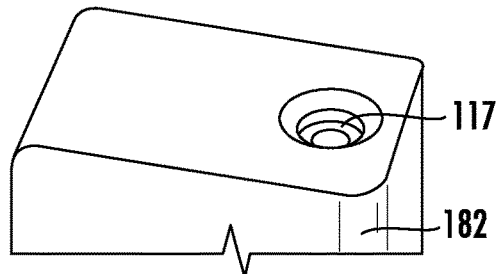
Figure 9E:
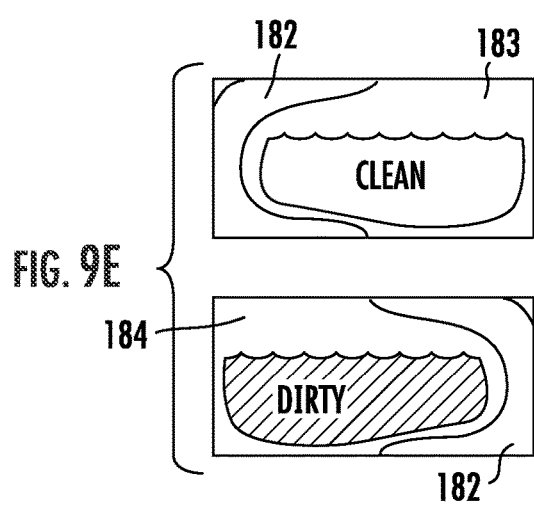

The cleaning-disinfecting system 100 may include a water reservoir 182. The water reservoir may be a removable water tank 182. As illustrated in FIG. 9D, the removable water tank 182 may include a water inlet 117. The cleaning-disinfecting system 100 and/or the removable water tank 182 may be directly filled with water through the water inlet 117 from a faucet or other water source. In various embodiments of the system, water used during the process may be collected in the removable water tank 182. The removable water tank 182 may include one or more flexible water bladders, as illustrated in FIG. 9E, such as a clean water flexible water bladder 183 and/or a dirty water flexible water bladder 184. The clean water flexible water bladder 183 and/or the dirty water flexible water bladder 184 may be refillable flexible bladders for holding both clean water and waste water. For example, when the clean water is pulled from the clean water flexible water bladder 183 for a reprocessing cycle, waste water from the reprocessing cycle begins to fill the dirty water flexible water bladder 184 within the removable water tank 182. Preferably, the water used in the reprocessing cycle may be tap water held in the clean water flexible water bladder 183 that is then pumped through a water filter 180 with sufficiently small pores so as to filter out water-borne pathogens such as *Mycobacterium* spp. which are known to be present in the water supply. In other embodiments of the cleaning-disinfecting system 100, the water used is distilled water, deionized water, or purified water. In another embodiment of the cleaning-disinfecting system 100, the water which is fed into the cleaning-disinfecting system 100 by the user is further treated with chemical buffers to alter the pH of the water to fall within the industry guidelines for critical water according to a pre-programmed process. In another embodiment of the cleaning-disinfecting system 100, the dirty water flexible water bladder 184 may include components that analyze the water for pH and dissolved minerals and compounds, and initiates an automated process of filtering or buffering the water using on-board reservoirs of materials so that the water falls within industry guidelines for critical water. Preferably, in various embodiments of the cleaning-disinfecting system 100, waste water from the process may be collected in the dirty water flexible water bladder 184. In another embodiment of the cleaning-disinfecting system 100, the waste water may be treated to reduce odor for discreet disposal in public areas such as restrooms.

Figure 10A:
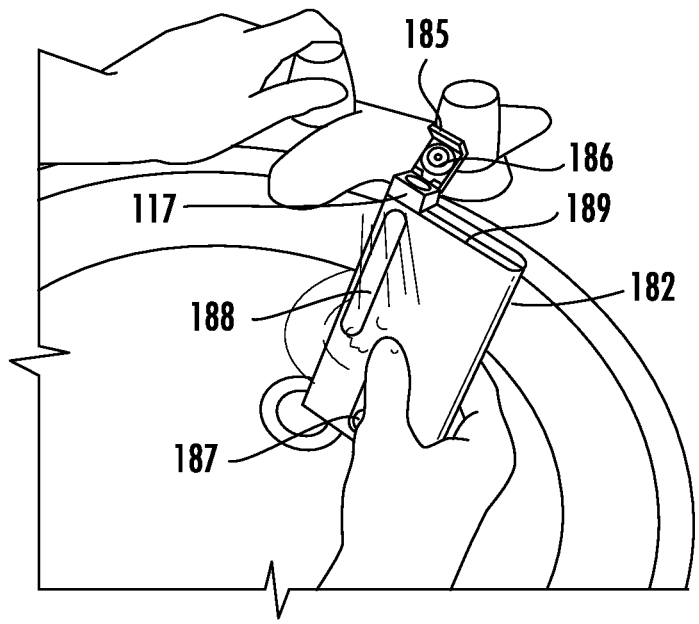
FIGS. 10A and 10B are perspective views of an illustrative embodiment of a clean water reservoir for a cleaning-disinfecting system for a medical device according to one embodiment of the invention.
Figure 10B:
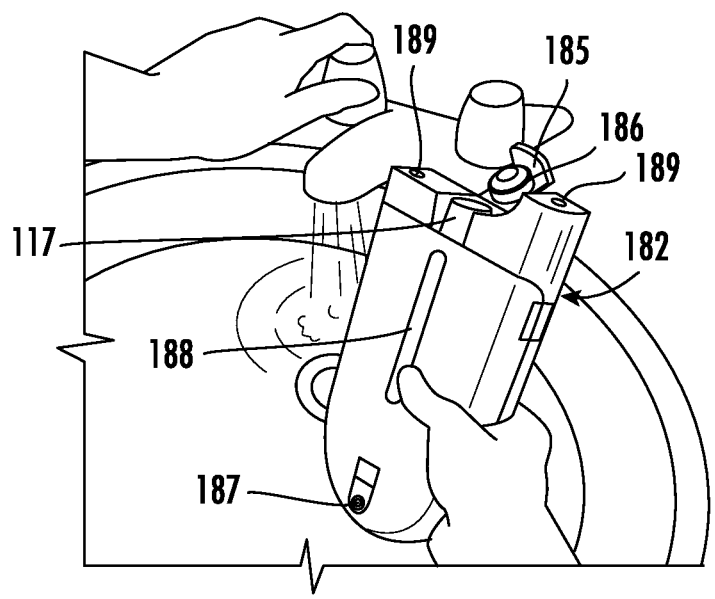

FIGS. 10A and 10B illustrate other embodiments of a water reservoir 182. The water reservoir 182 may include one or more water bladders (as shown in FIG. 9E), such as a clean water flexible water bladder 183 and/or a dirty water flexible water bladder 184. The water reservoir 182 may include a water reservoir lid 185 with an O-ring 186 for the clean water inlet 117 connected to the clean water flexible water bladder 183. The water reservoir 182 may also include a waste water outlet 187 connected to the dirty water flexible water bladder 184. The water reservoir 182 may include a fill window 188.

Additionally, the water reservoir 182 may include one or more ports 189. The one or more ports 189 may be female connections or male connections that include a valve. The valve and connections of the one or more ports 189 may provide an air-tight and water-tight valve connection with the water reservoir 182 to prevent leakage or contamination during supply transport and water transport. The one or more ports 189 may include one-way valves in the water reservoir 182 to prevent leakage or seepage of liquids after the water reservoir 182 is detached from the cleaning-disinfecting system 100.

Figure 11:
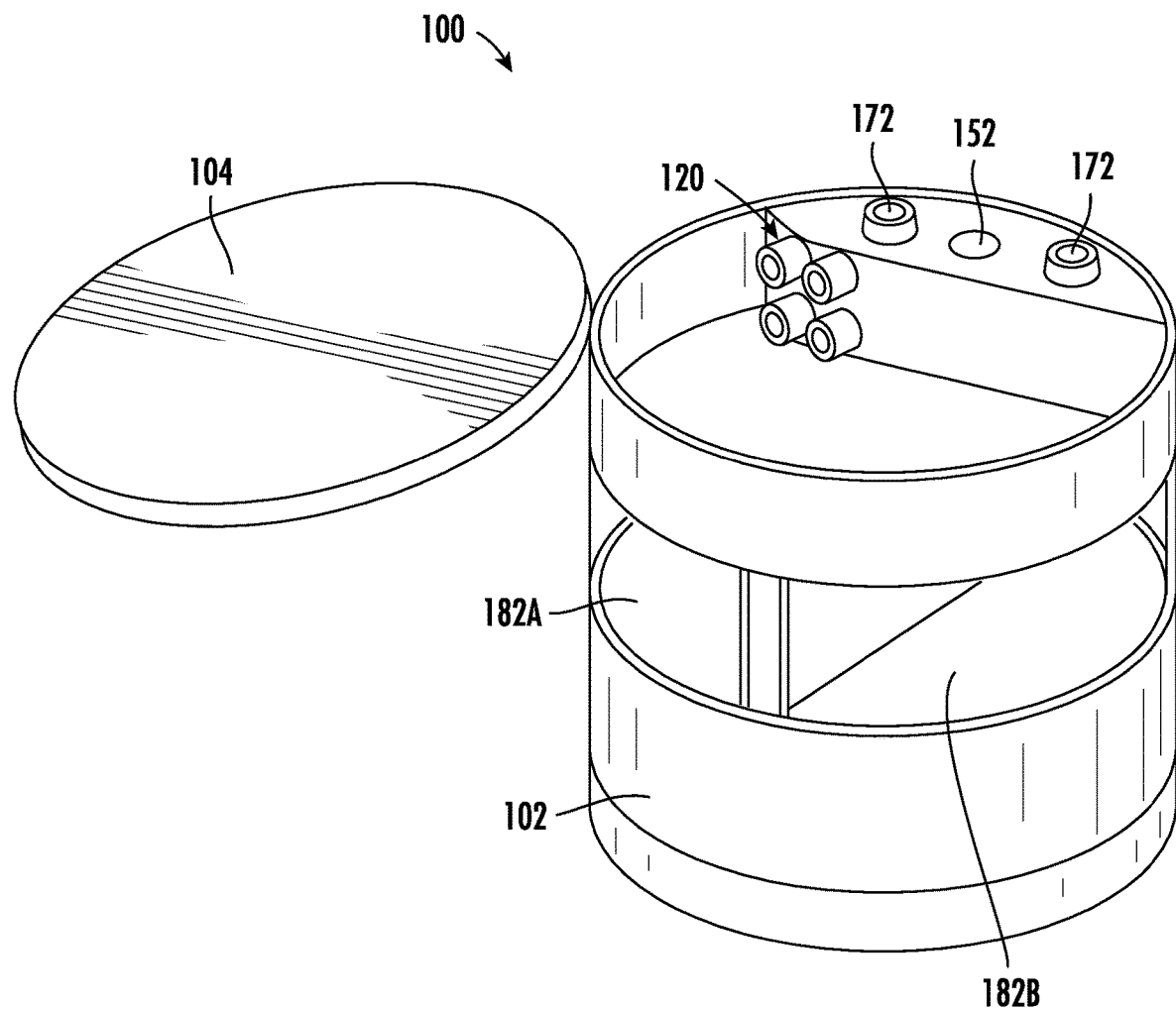
FIG. 11 is a perspective view of another illustrative embodiment of a cleaning-disinfecting system for a medical device according to one embodiment of the invention.
Figure 12:
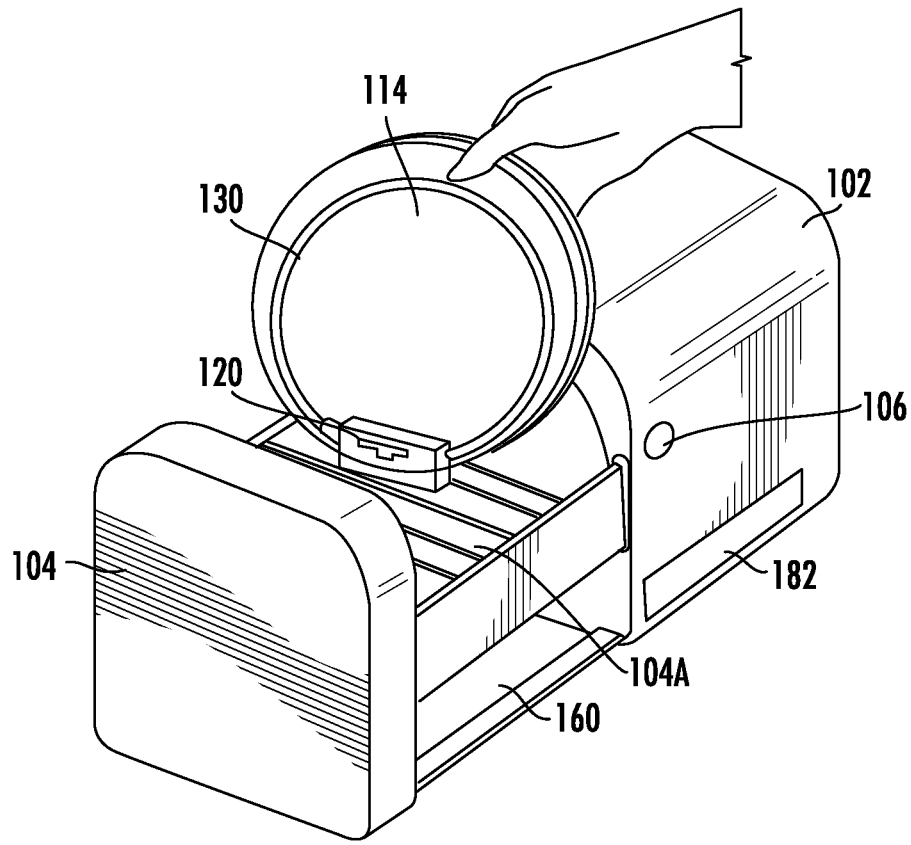
FIG. 12 is a perspective view of another illustrative embodiment of a cleaning-disinfecting system for a medical device according to one embodiment of the invention.
Figure 13:
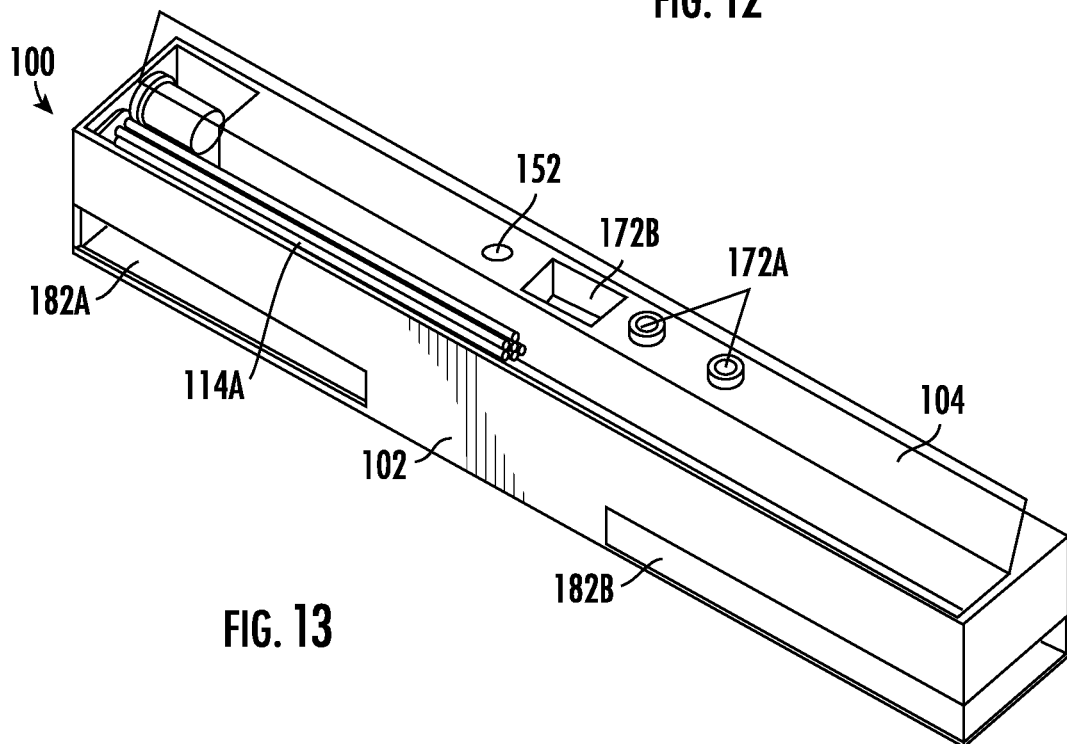
FIG. 13 is a perspective view of another illustrative embodiment of a cleaning-disinfecting system for a medical device according to one embodiment of the invention.

FIGS. 11-13 illustrate various embodiments of a cleaning-disinfecting system 100 that may be utilized to clean and disinfect multiple medical devices simultaneously. For example, the cleaning-disinfecting system 100 may be used at home to clean disinfect multiple medical devices, such as catheters.

FIG. 11 illustrates a cleaning-disinfecting system 100 that may include multiple medical device mounting ports 120, such as for multiple catheters. The cleaning-disinfecting system 100 may include a lid 104 with a reprocessor base 102. The cleaning-disinfecting system 100 may also include a slot for a removable clean water reservoir 182A and a separate location for a removable waste water reservoir 182B. Further, on a top portion, the cleaning-disinfecting system 100 may include one or more of a power button 152 and one or more cleaning/detergent/disinfectant inlets 172.

FIG. 12 illustrates a cleaning-disinfecting system 100 that may include a door 104 that slides open from a base 102. The base 102 may include an eject or open button 106. The cleaning-disinfecting system 100 may include one or more catheter trays or mounts 114 that slide into one of a plurality of slots 104A in the door 104. The catheter trays 114 may include a pair of mounting ports 120 for the ends of a catheter 130. The cleaning-disinfecting system 100 may include an RFID scanner 160. The cleaning-disinfecting system 100 may include a clean water inlet 117 located within the base 102 of the cleaning-disinfecting system 100.

FIG. 13 illustrates a linear cleaning-disinfecting system 100 with a catheter spindle rack 114A to hold and mount a plurality of catheters 130. The cleaning-disinfecting system 100 may include a base 102 with a lid 104 that opens for access to the catheter spindle rack 114A and plurality of catheters 130. The cleaning-disinfecting system 100 may include a power button 152 located on the base 102. The base 102 of the cleaning-disinfecting system 100 may also include one or more cleaning/detergent/disinfectant inlets 172A. Further, the cleaning-disinfecting system 100 may include a secondary cleaning supply inlet/port 172B that may be utilized for the insertion of daily cleaning supplies which may be in the form of a chemical cup or chemical pack that can be utilized for one or more reprocessing cycles. The cleaning-disinfecting system 100 and the base 102 may include a slot for both a removable clean water reservoir 182A and a separate location for a removable waste water reservoir 182B.

Figure 14A:
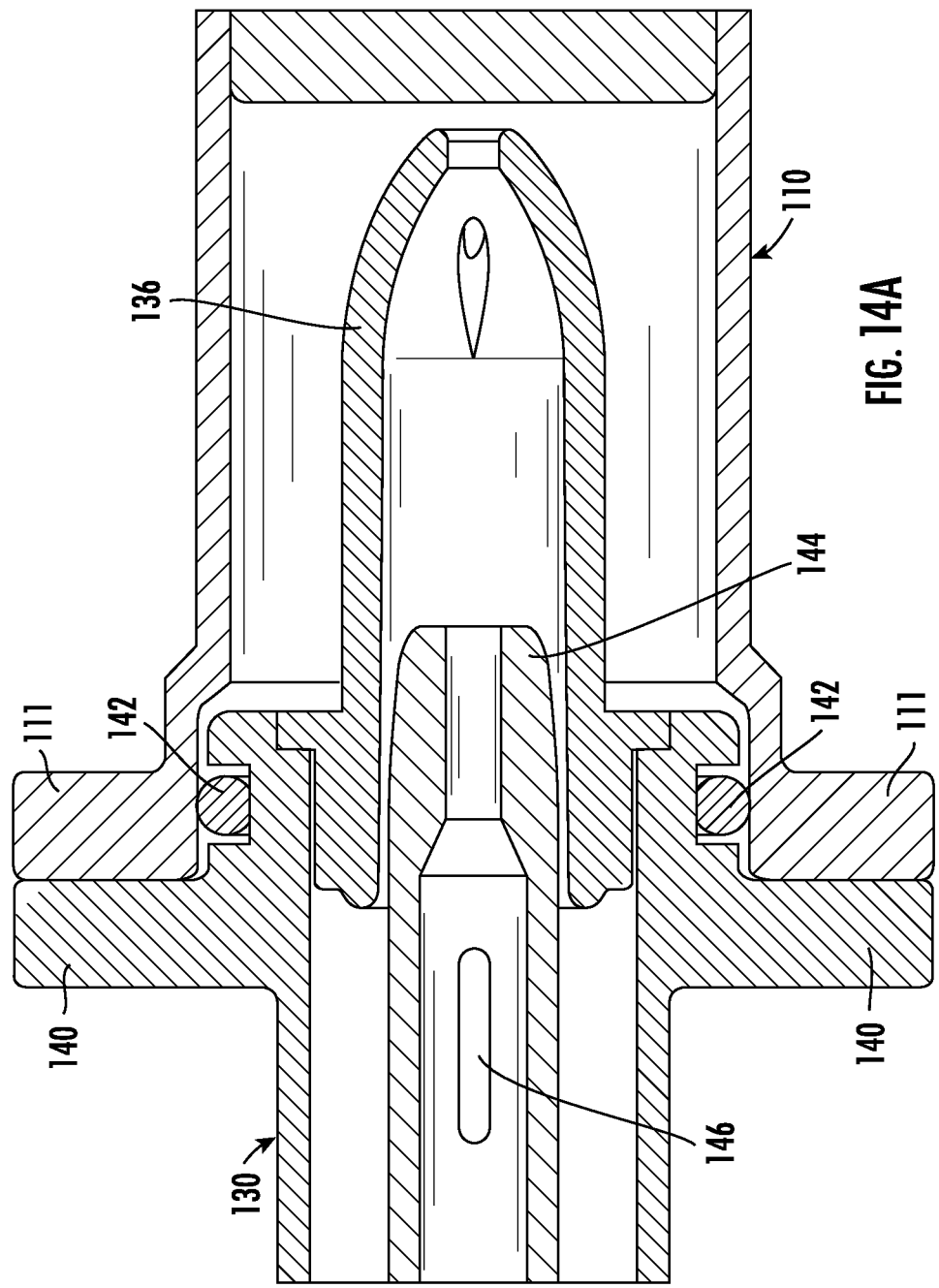
Figure 15A:
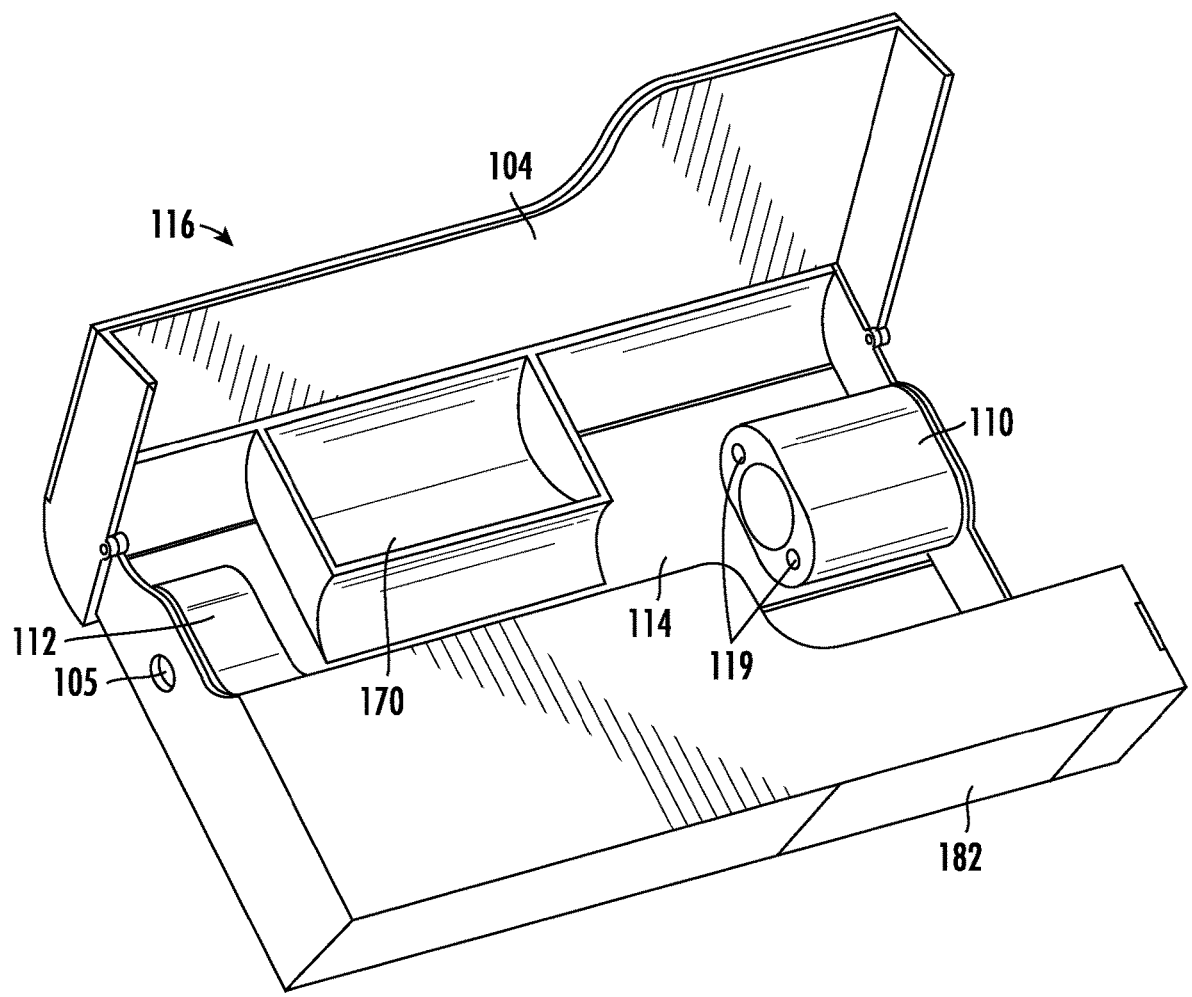
FIGS. 15A and 15B are views of a mounting tray and housing for a cleaning-disinfecting system for a medical device according to one embodiment of the invention.
Figure 15B:
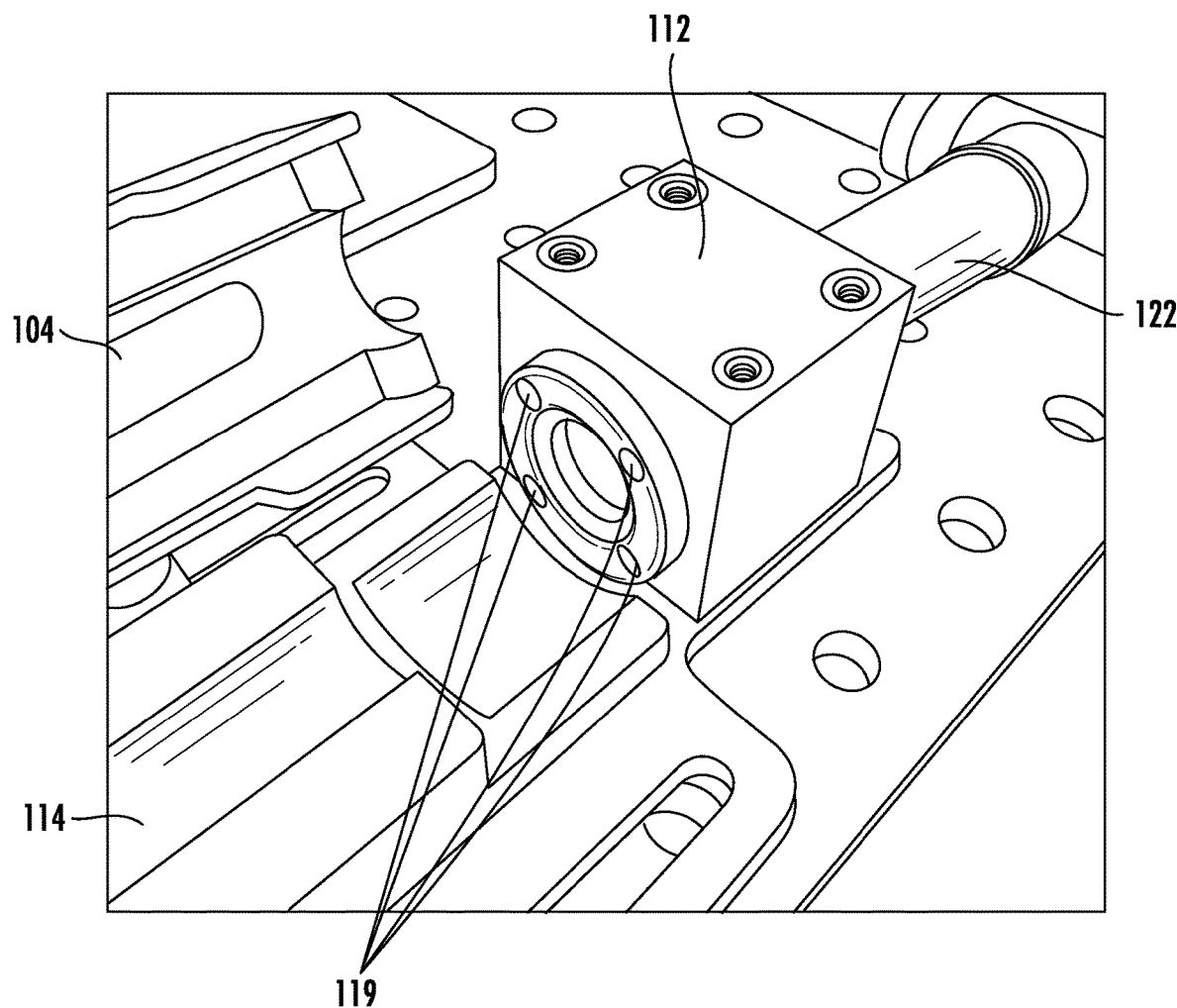
Figure 16A:
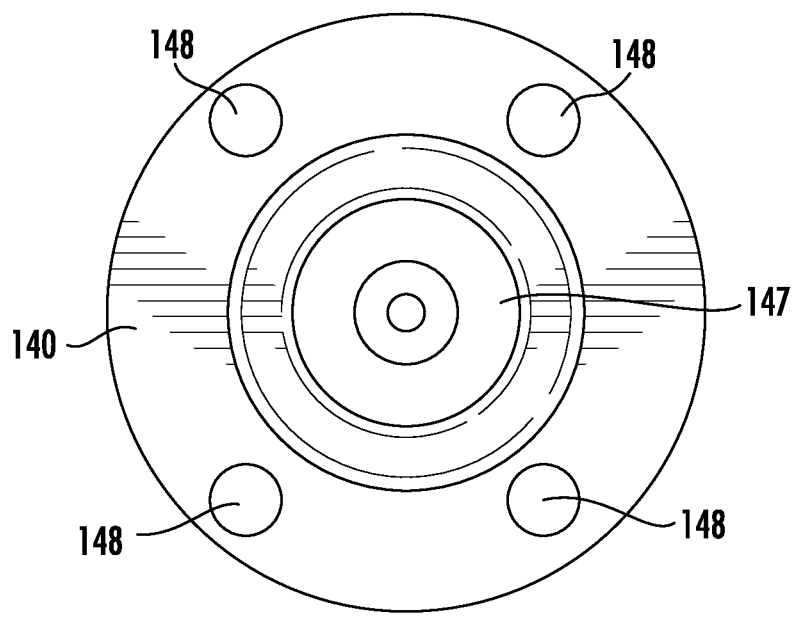
FIGS. 16A-16D are front views of a flange for a medical device according to one embodiment of the invention.
Figure 16B:
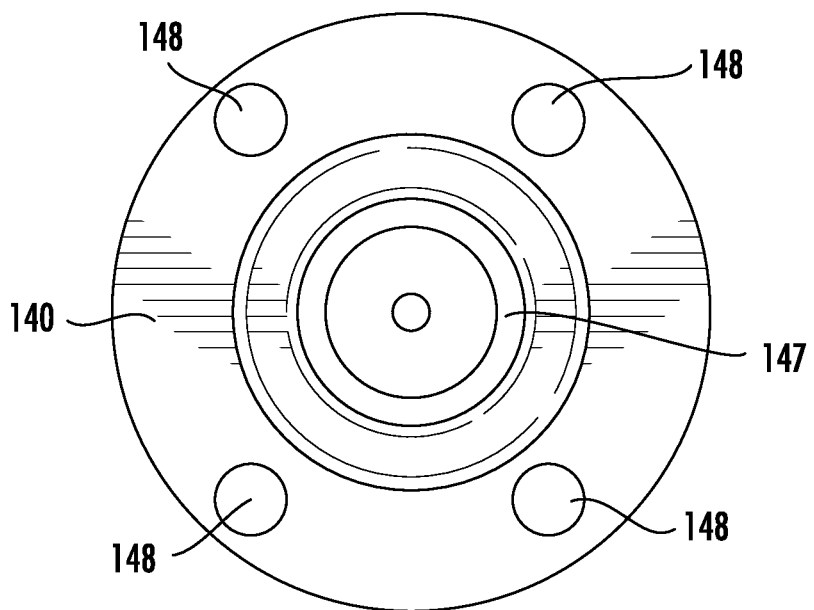
Figure 16C:
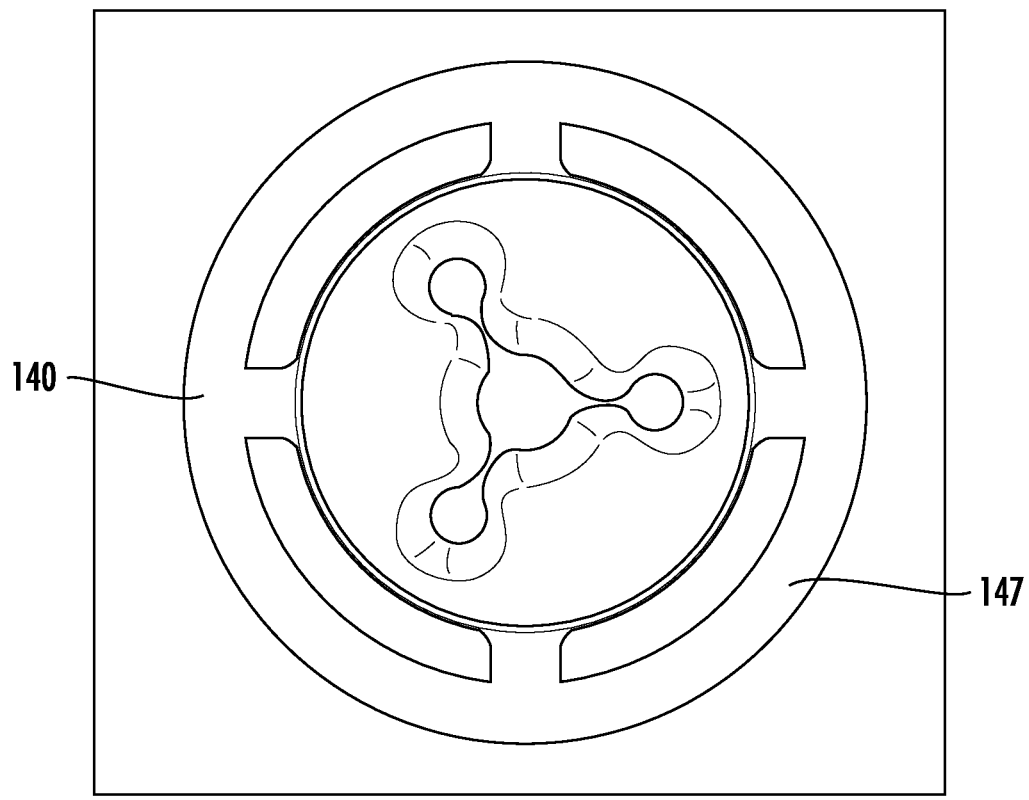
Figure 16D:
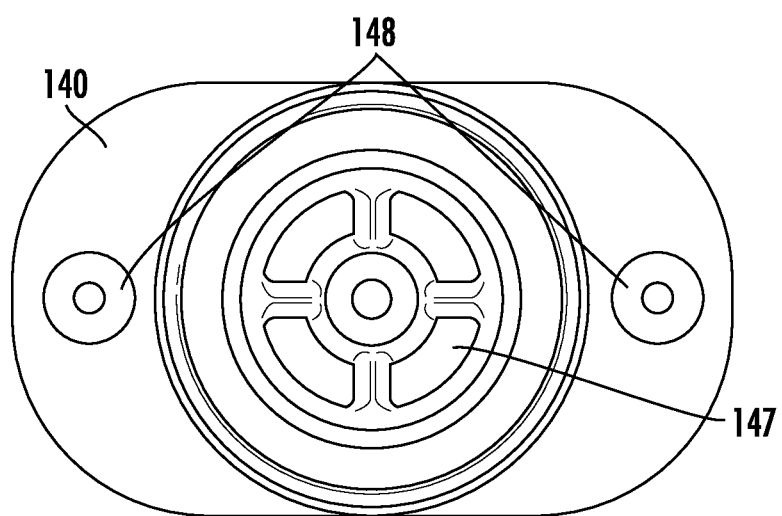

FIGS. 14A and 14B illustrated exemplary embodiments of the interface between the ends of a medical device or catheter 130 and a catheter tip housing 110 and a catheter funnel housing 112. As illustrated in FIG. 14A, a first end with the introducer tip 136 of the catheter 130 may connect to the catheter tip housing 110. As illustrated in FIG. 14B, a second end of the catheter 130 may connect to the catheter funnel housing 112. Each of the catheter tip housing 110 and the catheter funnel housing 112 may include flow connectors to connect to the first end and the second end of the catheter 130. The interfaces and flow connectors between the cleaning-disinfecting system 100 and the catheter 130 provide a water-tight and air-tight seal and forms a closed-loop fluid pathway 122 with the cleaning-disinfecting system 100. Each of the catheter tip housing 110 and the catheter funnel housing 112 may include flow connectors that interface and connect with the ends of the catheter 130. Each of the ends of the catheter 130 may include one or more flanges 140 that interface and connect with one or more flanges 111 of the catheter tip housing 110 and the catheter funnel housing 112. The flanges 140 on the catheter 130 may also include an o-ring 142 or other sealing mechanism to help provide the water-tight and air-tight seal between the flanges 140 on the catheter 130 and the flanges 111 on the housings 110, 112. As further illustrated in FIG. 14A, the catheter 130 may include a council tip 143 and an eyelet 144. FIG. 14B specifically illustrates the funnel end of the catheter 130. As illustrated in FIG. 14B, the catheter 130 may include on the second end, a funnel 139, an internal catheter seat 144, a catheter shaft 145, a catheter sheath 146, and a fluid channel 147. The funnel end of the catheter 130 may also include flanges 140 and an o-ring 142 for the interface between the funnel 139 and the catheter funnel housing 112 (not shown in FIG. 14B).

According to another embodiment, medical devices or supplies may be loaded into the cleaning-disinfecting system 100 in a particular orientation to facilitate the flow of fluids through the fluid channel 147 of the devices or supplies in order to minimize the amount of air trapped in the system. FIGS. 15A, 15B, and 16A-D illustrate the interaction between the magnets 119, 148 and the loading of medical devices or supplies with the cleaning-disinfecting system 100. The magnets 119, 148 may be utilized to properly seat the medical devices or supplies into the cleaning-disinfecting system 100, reducing the operator's need to physically push or pull the medical devices or supplies into position. Another embodiment of the cleaning-disinfecting system 100 may utilize an asymmetric array of magnets 148 to facilitate the loading of the medical device in a particular orientation to prevent twisting or otherwise disadvantageous positioning of the medical device in the cleaning-disinfecting system 100 that may damage the device or prevent the complete cleaning and disinfection of the device within the cleaning-disinfecting system 100. The medical device itself may feature magnets or ferrous metal to facilitate a magnetically-augmented loading mechanism into the cleaning-disinfecting system 100. For example, the flanges 140 of the medical device or catheter 130 may interface and connect with magnets 119 on the catheter tip housing 110 and/or the catheter funnel housing 112 of the cleaning-disinfecting system 100. In various embodiments of the cleaning-disinfecting system 100, the medical devices may be stored in a straight orientation, a u-shaped orientation, a looped orientation, or a coiled orientation to reduce the amount of space that the medical device takes up within the cleaning-disinfecting system. In a preferred embodiment of the cleaning-disinfecting system 100, the medical device or supply being reprocessed in the cleaning-disinfecting system 100 features fluid channels 147 in both the proximal and distal ends of the device to ensure that reprocessing fluids can circulate throughout the device and that all user-contacting surfaces of the device are reprocessed to the standards set out by the FDA.

As further illustrated in FIG. 17, the medical device may be further positioned optimally within the cleaning-disinfecting system 100 through the use of spring-loaded, dynamic or static features with lead-ins that compress the medical device against the cleaning-disinfecting system in order to create a water-tight and/or air-tight seal. Static or dynamic features with lead-ins that compress the medical device against the cleaning-disinfecting system in order to create a water-tight and/or air-tight seal. FIG. 17 shows a representation of a lid 104 of the cleaning-disinfecting system 100 closing to compress the medical device to create a water-tight and/or air-tight seal. For example, the closing of the lid 104 may pushes against a surface or dynamic lead-in 101 pushing towards a compression surface 103 within the cleaning-disinfecting system 100, thereby creating a water-tight and/or air-tight seal for the closed-loop fluid pathway 122 of the cleaning-disinfecting system 100 and medical device or catheter components.

Figure 18A:
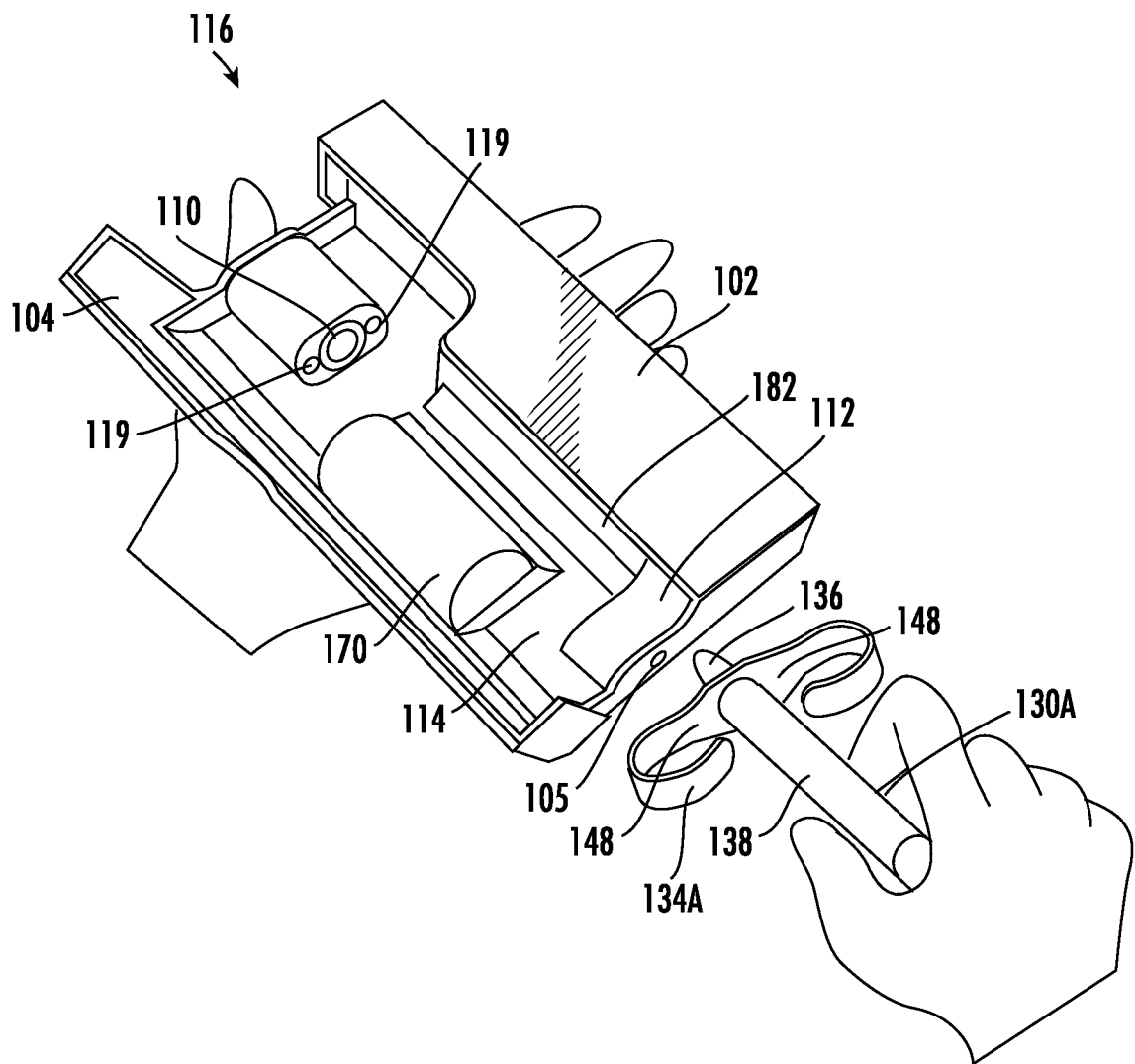
FIGS. 18A-18C are perspective views of a cleaning-disinfecting system for a medical device according to one embodiment of the invention.
Figure 18B:
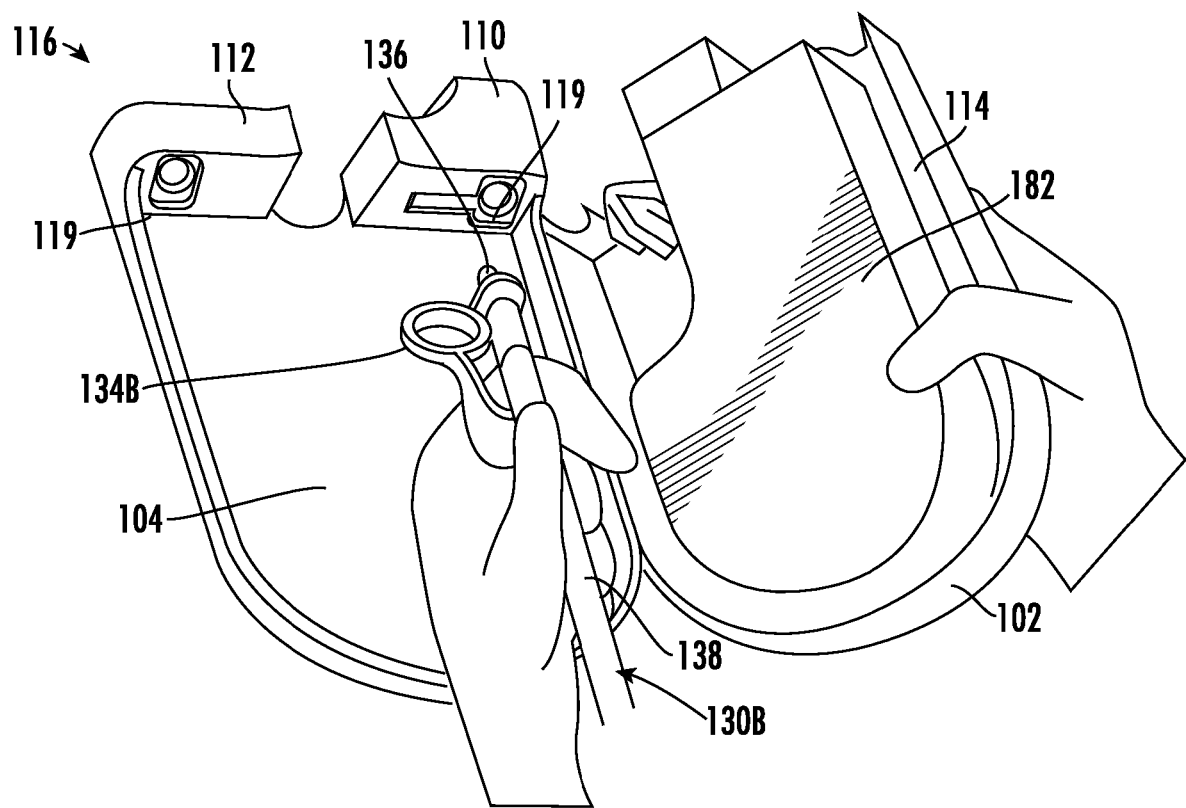
Figure 18C:
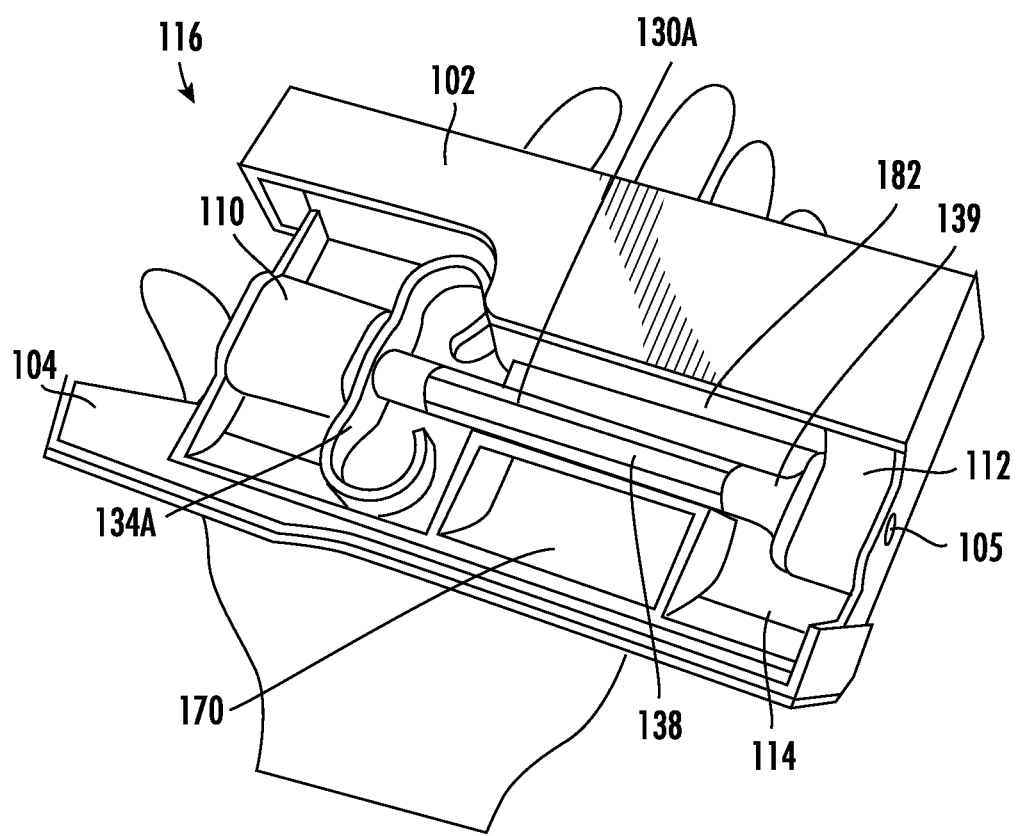

FIGS. 18A-C illustrate the loading of a medical device or catheter 130 into an exemplary cleaning-disinfecting system 100 and specifically a carrying case 116. FIG. 18A specifically shows the loading of a female catheter 130A into the carrying case 116 of the cleaning-disinfecting system 100 and FIG. 18B shows the loading of a male catheter 130B into the carrying case 116 of the cleaning-disinfecting system 100. FIG. 18C shows the female catheter 130A loaded into the cleaning-disinfecting system 100.

Figure 19A:
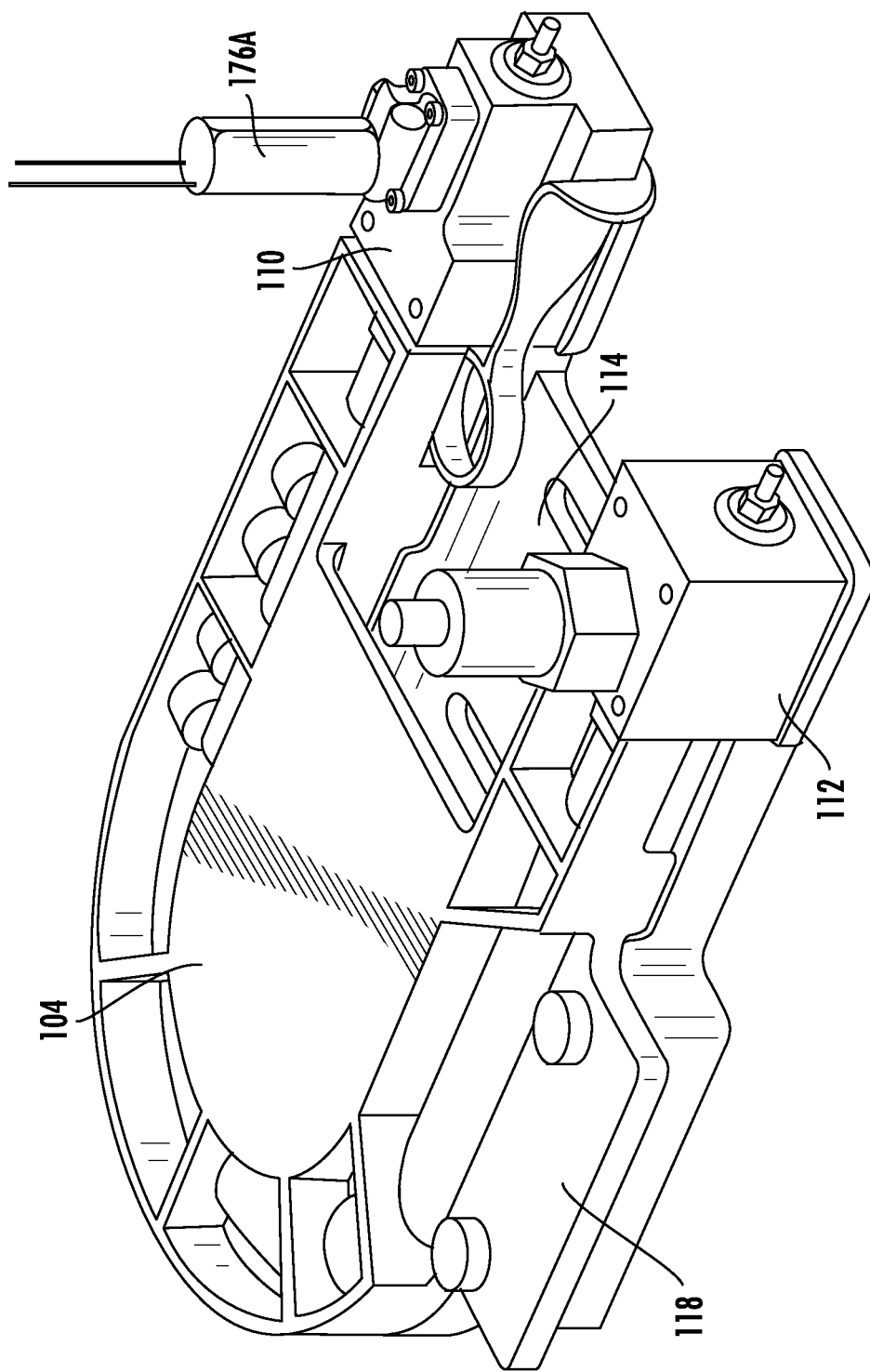
FIGS. 19A and 19B are perspective views of a housing and flow connectors for a cleaning-disinfecting system for a medical device according to one embodiment of the invention.
Figure 19B:
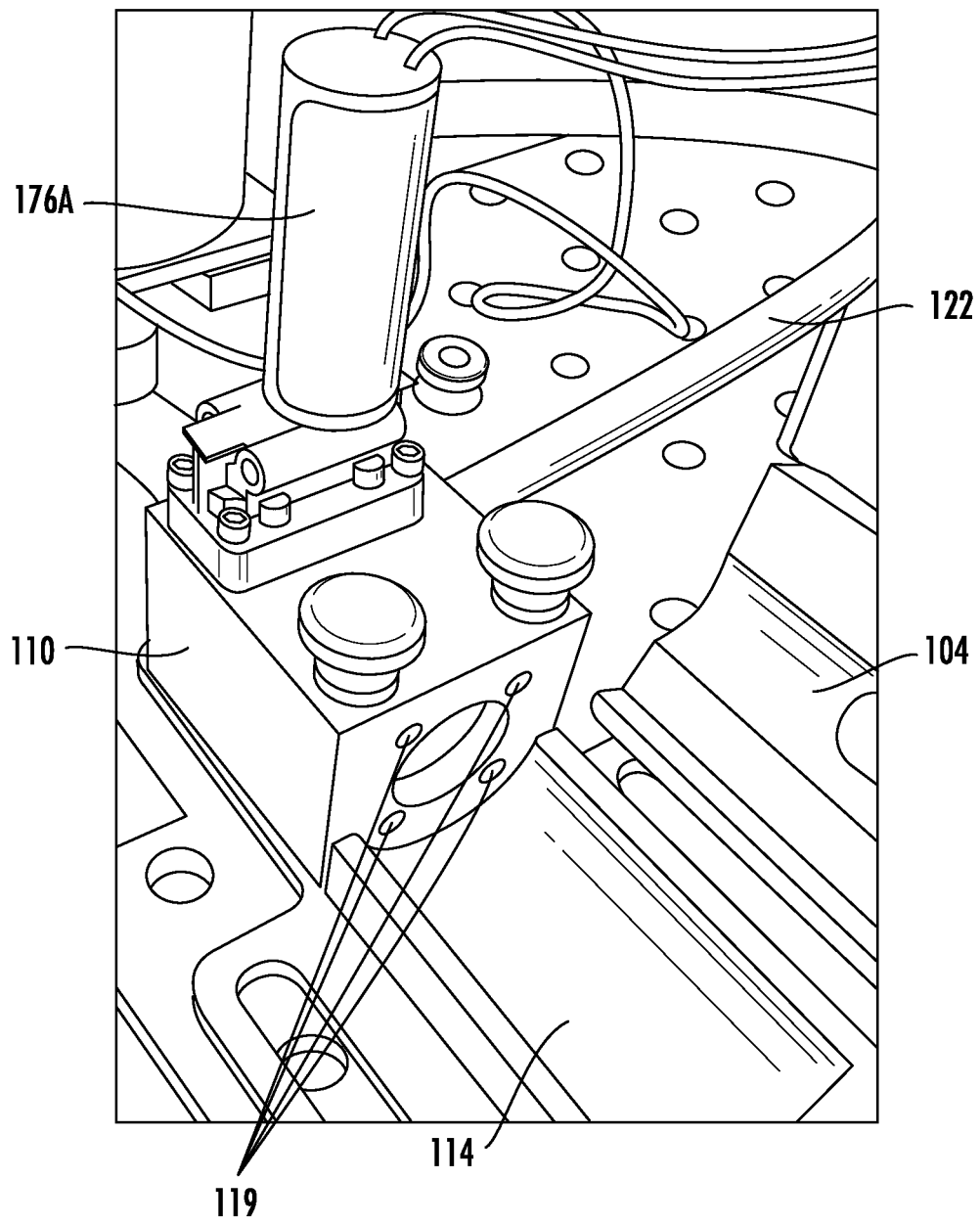

In an embodiment of the cleaning-disinfecting system 100, lubricant may be applied to the medical device that is being reprocessed after the completion of the cleaning and disinfection stages of the reprocessing cycle using a primary pumping apparatus and fluid flow path in the cleaning-disinfecting system. Additionally, another embodiment of the cleaning-disinfecting system 100 achieves the circulation of reprocessing materials through the medical device and supply using a diaphragm or peristaltic pump. Additionally, during this circulation period, the system may use a heating element to increase the temperature of the fluids in the cleaning-disinfecting system 100 to approximately 40 degrees Celsius to maximize the efficacy of the enzymatic reaction. FIGS. 19A, 19B, 20A-D, and 21A-D illustrate various embodiments of the cleaning-disinfecting system 100 and the closed-loop fluid pathway 122 with various other components, such as a lubricant dosing pump 176A, a secondary lubricant pump 176B, a lubricant reservoir 177, a dosing pump 178, and/or a ceramic heater 179. Specifically, FIGS. 19A and 19B illustrate a cleaning-disinfecting system 100 with a lubricant dosing pump 176. FIGS. 20A-D illustrate various schematics and representations of cleaning-disinfecting systems 100 and the closed-loop fluid pathway 122 with one or more of the components of: a cleaning supply reservoir 170 (which may include a detergent reservoir 170A and/or a hydrogen peroxide reservoir 170B), a clean water reservoir 182A, a waste water reservoir 182B, a HEPA filter 173, the lubricant dosing pump 176A, the secondary lubricant pump 176B, the lubricant reservoir 177, the dosing pump 178, and/or the ceramic heater 179.

FIGS. 21A-D illustrate various methods for applying the lubricant from the lubricant dosing pump 176 or other methods. Lubricant may be applied to the catheter 130 by physically manipulating the medical device and advancing the portion of the catheter 130 that needs to be lubricated into a lubricant reservoir 177 through a lubricant fluid port 154. Alternatively, the catheter 130 may feature a lubricant fluid pathway 156 that facilitates the deposition of lubricant in the appropriate area of the catheter 130.

As illustrated in FIG. 21C, the catheter 130 may include a replaceable cartridge of lubricant 177A with one or more pierceable membranes 177B. The insertion aid 134 may be moved back to extend the catheter 130 with the catheter tip 136 piercing the membranes 177B allowing lubrication to flow. The catheter funnel end 139 may be fixed in place. The catheter sheath 146 may compress as the insertion aid 134 is moved toward the funnel 139 to lubricate the catheter 130 and catheter shaft 145.

As illustrated in FIG. 21D, lubricant may be stored in a static reservoir 177 and is applied to the reprocessed medical device/catheter 130 through a manual process wherein the user dips the medical device/catheter 130 into the reservoir 177.

Figure 22:
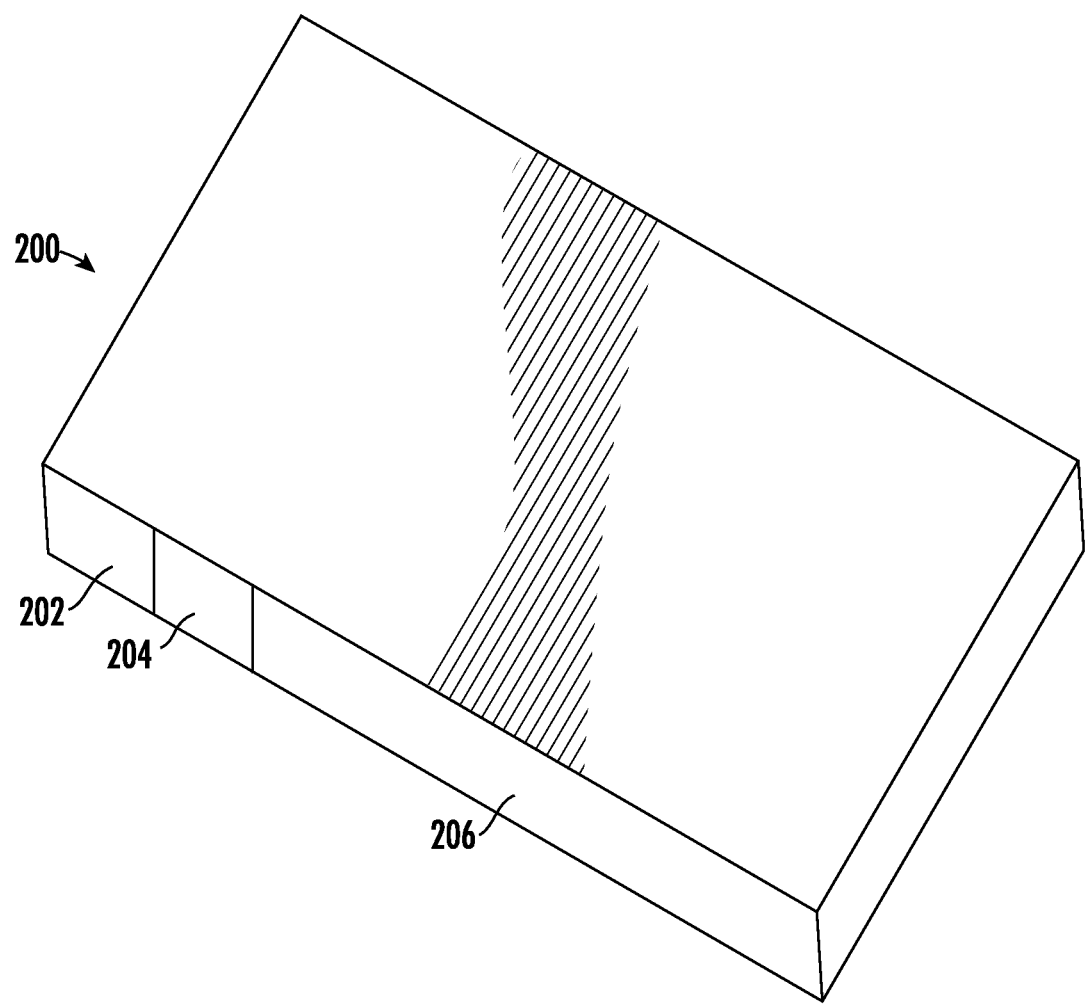
FIG. 22 is a perspective view of a storage case for cleaning and disinfection supplies for a cleaning-disinfecting system according to one embodiment of the invention.
Figure 23A:
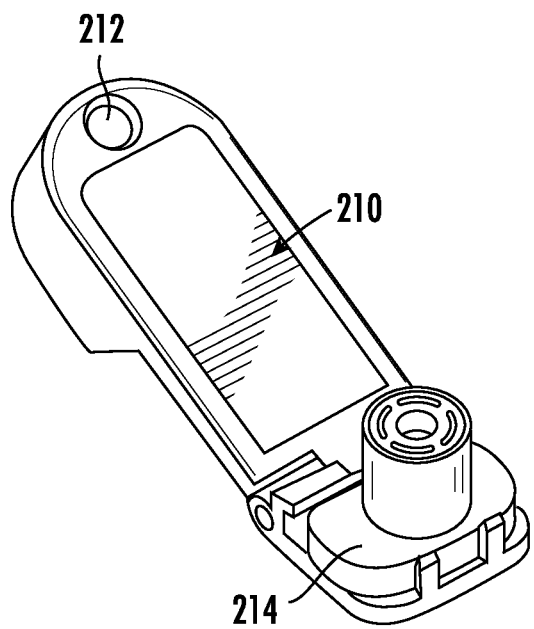
FIGS. 23A-23D and 24A-24C are various views of various configurations of mirrors for a medical device or catheter according to one embodiment of the invention.
Figure 23B:
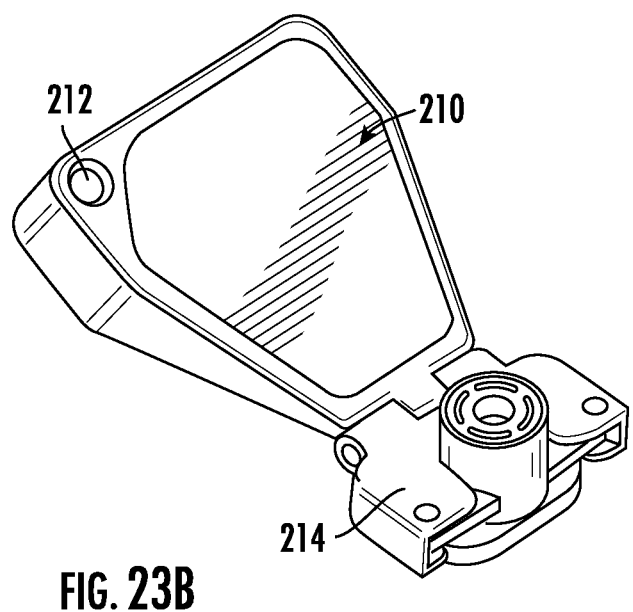
Figure 23C:
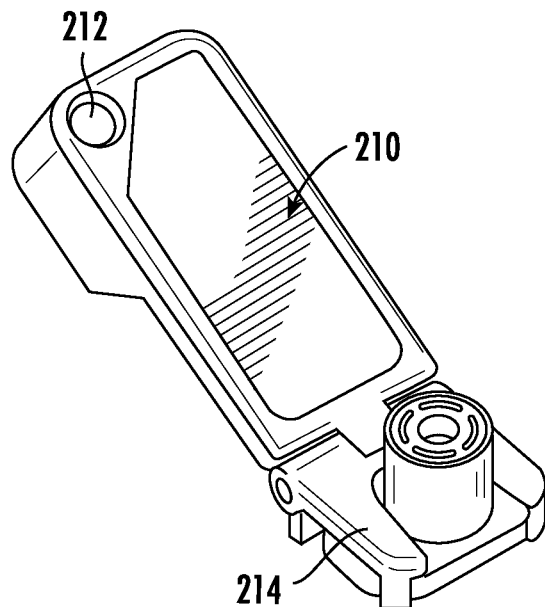
Figure 23D:
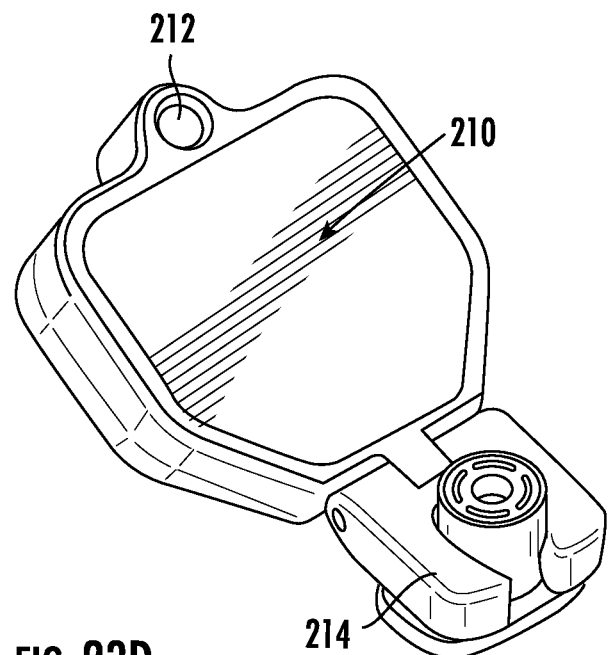
Figure 24A:
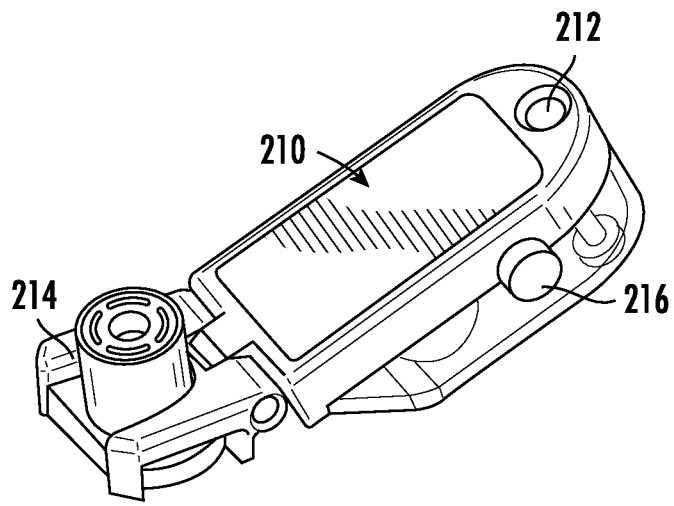
Figure 24B:
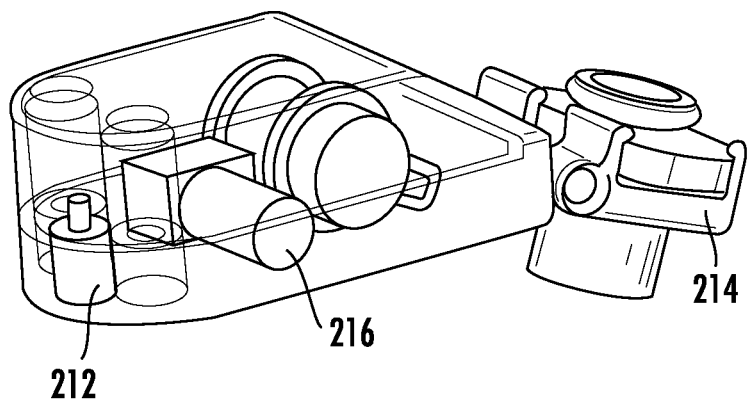
Figure 24C:
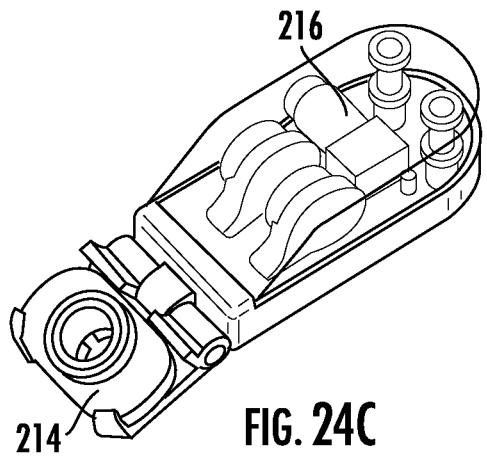

FIG. 22 illustrates an embodiment of the cleaning-disinfecting system 100 that includes a stiff plastic storage case 200 for cleaning and disinfection supplies. The storage case 200 may include supplies used to reprocess medical devices that may be packaged together in a convenient format for storage, transportation, and use by the user of the reprocessor. The storage case 200 may include enzymatic cleaner 202, lubricant 204, and/or a high-level disinfectant 206. The enzymatic cleaner 202, lubricant 204, and/or high-level disinfectant 206 may be stored in a flexible plastic bladder within the storage case 200.

FIGS. 23A-D, 24A-C, 25A-C, 26A-D, 27, and 28 illustrate various accessories for a medical device or catheter 130. Specifically, FIGS. 23A-D and 24A-C illustrate various configurations of mirrors 210 with or without LED lights 212. The mirrors 210 may include a catheter mount 214 to mount the mirror 210 to the catheter 130. The mirrors 210 and lights 212 may be battery driven, such as with two batteries. Additionally, the mirror 210 may include a button switch 216 on the side of the mirror 210 that may be utilized for activating and turning on the lights 212.

Figure 25A:
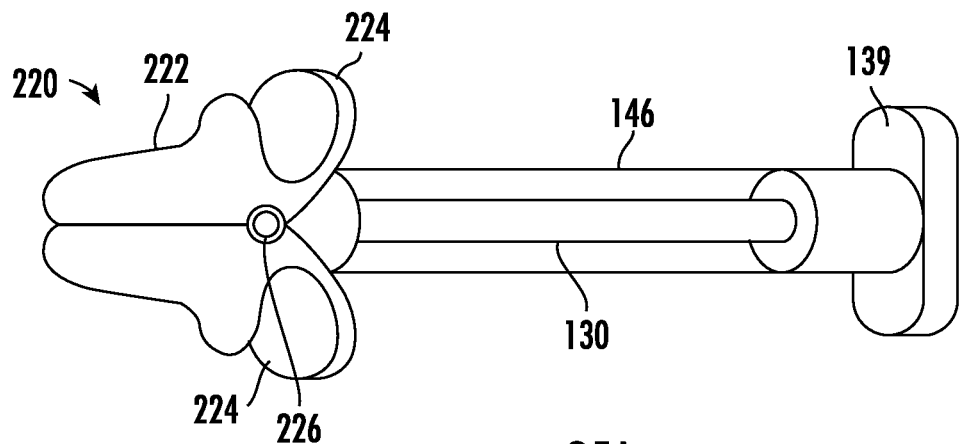
FIGS. 25A-25C are various views of various configurations of a labial spreader for a medical device or catheter according to one embodiment of the invention.
Figure 25B:
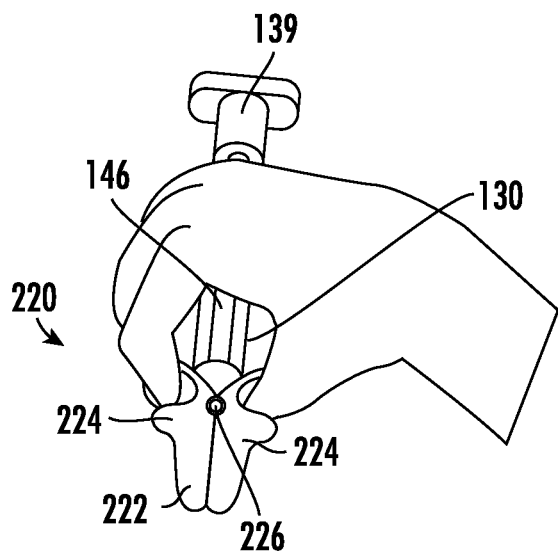
Figure 25C:
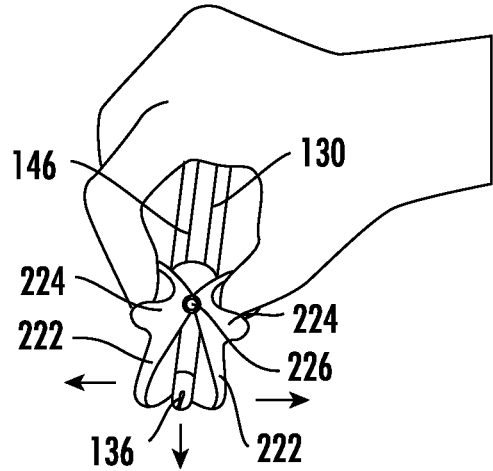

FIGS. 25A-C illustrate a spreader 220 used to manipulate the user's tissue and skin without directly contacting them. The spreader 220 may include a labial spreader 222 with one or more flanges 224 and a fulcrum 226 connected to the introducer tip 136 of the catheter 130. The catheter 130 may further include a collapsible sheath 146 and a funnel 139. As illustrated in FIG. 25B, the catheter may be positioned with the spreader 220 and labial spreader 222 between the labia. As illustrated in FIG. 25C, the user may push the flanges 224, which spreads the labia while advancing the introducer tip 136 into the urethral opening. The other hand of the user may then push the catheter 130 into the urethra with the funnel 139.

FIGS. 26A-D and 27 illustrate adjustable mechanisms that help create physical support or leverage as the medical device or catheter 130 is being used in order to prevent accidental insertion or use of the medical device or catheter 130 in a manner or into a bodily opening that the user did not intend.

Figure 26A:
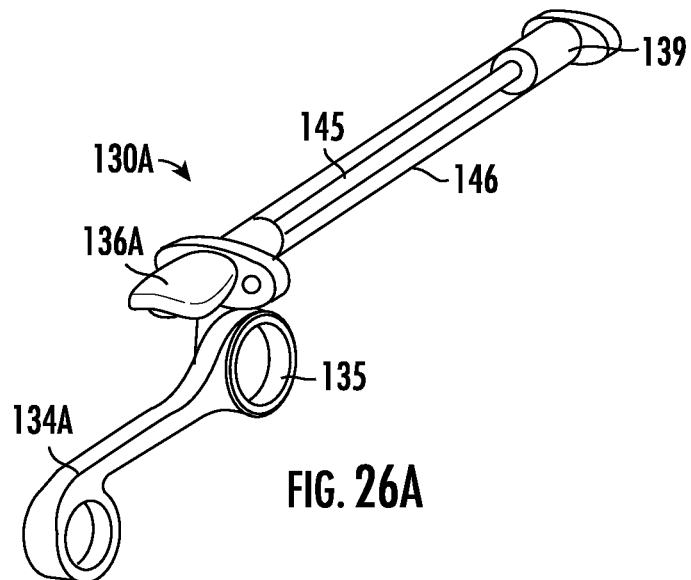
FIGS. 26A-26D are various views of various configurations of a handle and other tip accessories for a medical device or catheter according to one embodiment of the invention.
Figure 26B:
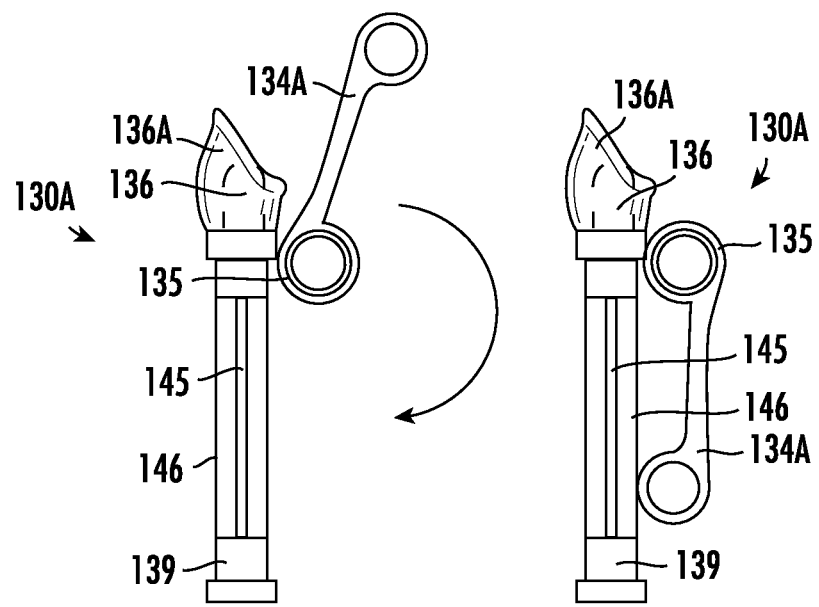
Figure 26C:
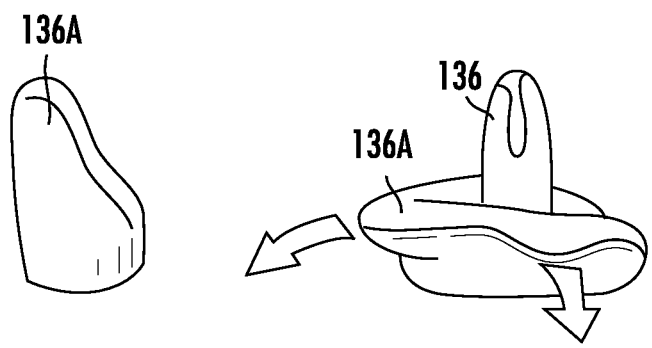
Figure 26D:
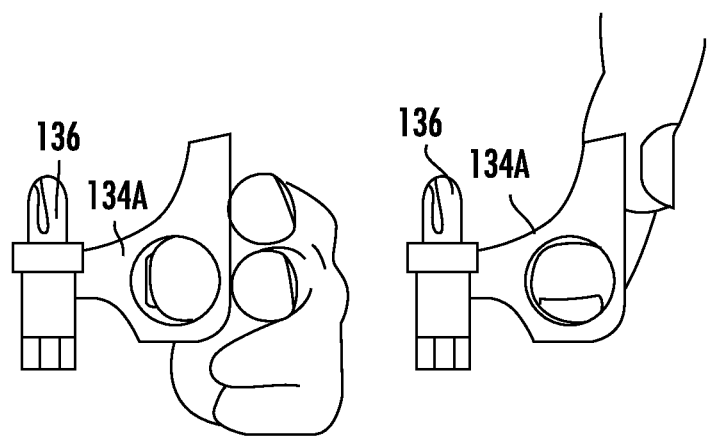
Figure 27:
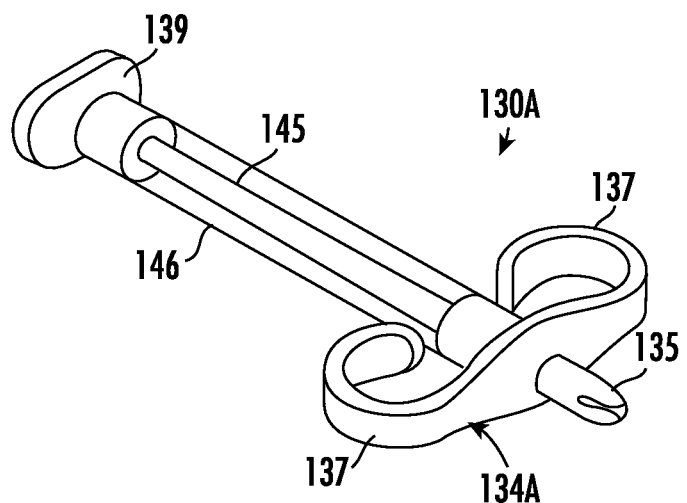
FIG. 27 illustrates a perspective view of another exemplary female catheter with an insertion aid with finger loops according to one embodiment of the invention.

As illustrated in FIGS. 26A-D, a female catheter 130A may include an insertion aid or handle 134A. The handle 134A may include an articulating joint 135 so that the handle can fold over against the catheter 130A for storage. Additionally, the catheter 130A may include a tip cover 136A to cover the catheter tip 136. As illustrated in FIG. 26C, the tip cover 136A may be a compression, wherein when the tip cover 136A is compress, the tip cover 136A spreads the labia of the user to assist with insertion. FIG. 26D illustrate other embodiments of the handle 134A, wherein the handle 134A is in the shape of a snub-nose handle (note—tip cover 136A is not shown in FIG. 26D). FIG. 27 illustrates another exemplary female catheter 130A with an insertion aid 134A with finger loops 137.

Figure 28:
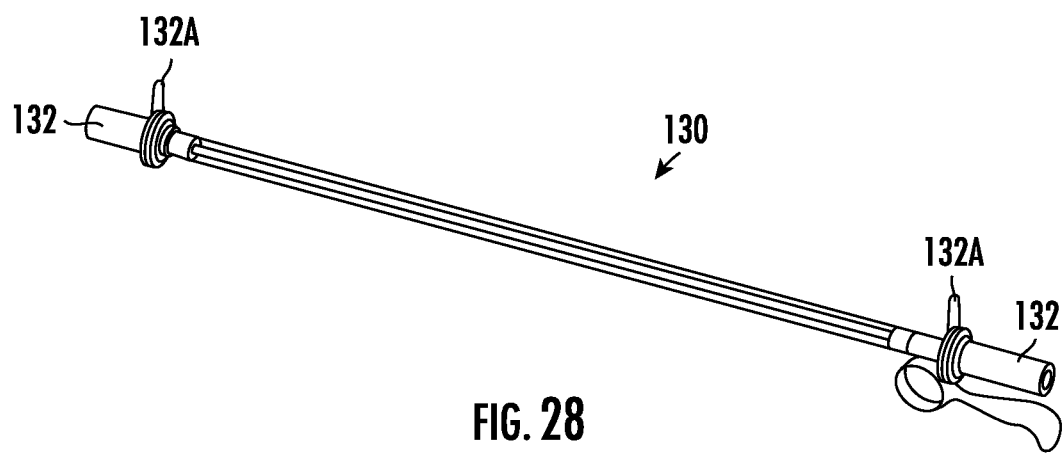
FIG. 28 illustrates a catheter with caps at either end of the catheter according to one embodiment of the invention.

FIG. 28 illustrates a catheter 130 with caps 132 at either end of the catheter 130 to prevent the leakage of fluids from the medical device or catheter 130 after the medical device or catheter 130 has been removed from the cleaning-disinfecting system 100. The caps 132 include a tether 132A that may tether the caps 132 to the medical device or catheter 130 to prevent accidental loss of the caps 132.

Figure 29A:
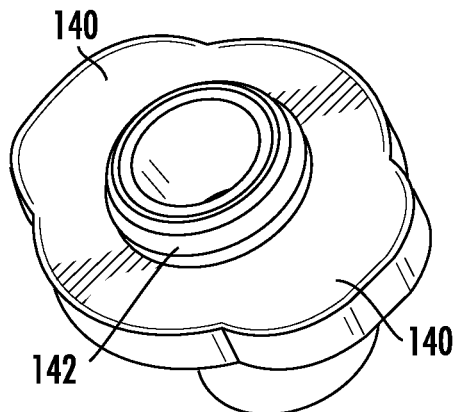
FIGS. 29A-29F illustrate various views of various configurations of RFID/NFC tags that may be incorporated onto the ends of a catheter according to one embodiment of the invention.
Figure 29B:
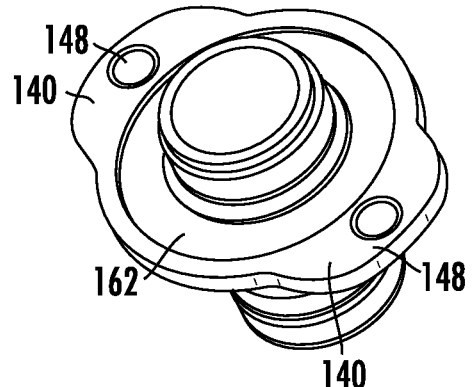
Figure 29C:
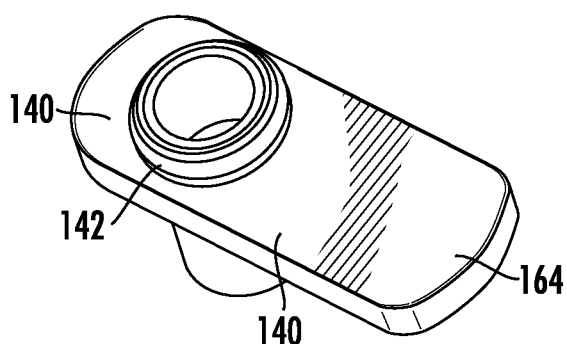
Figure 29D:
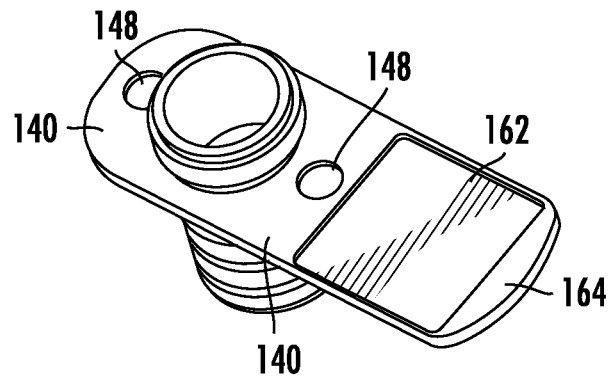
Figure 29E:
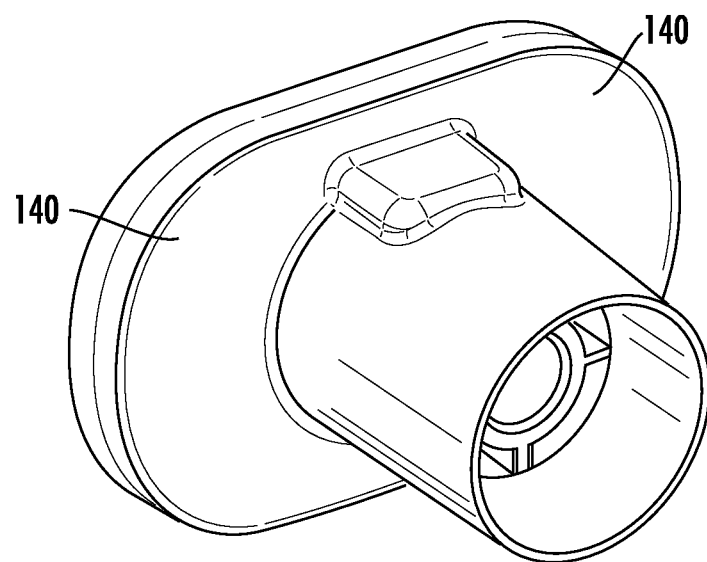
Figure 29F:
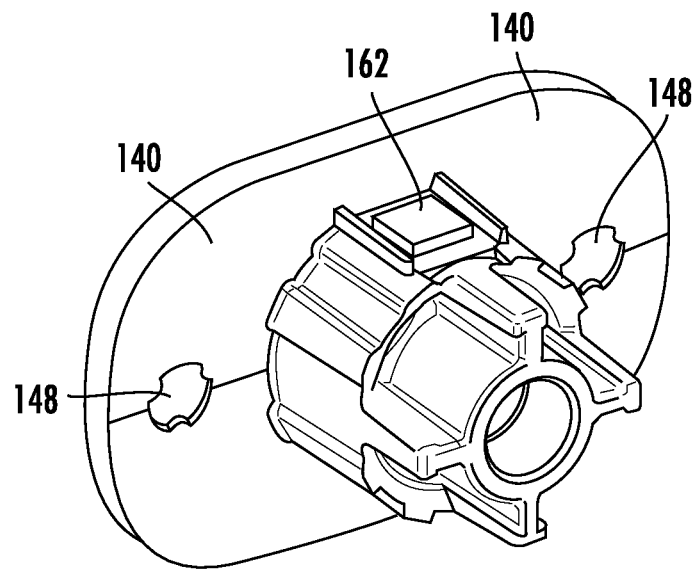

FIGS. 29A-F illustrate embodiments of RFID/NFC tags 162 that may be incorporated onto the ends of the catheter 130. As shown in FIGS. 29A and 29B, the RFID/NFC tags 162 may be located on a tab 164 that extends from the catheter 130 and catheter flange 140 and o-ring 142. As shown in FIGS. 29C and 29D, the RFID/NFC tag 162 may be located on the catheter flange 140 adjacent to the o-ring 142 and extend around the catheter 130. As shown in FIGS. 29E and 29F, the RFID/NFC tag 162 may be located and embedded in an internal portion of the catheter flange 140. The ends of the catheter 130 may also include magnets 148 to connect to the housing of the cleaning-disinfecting system 100 to form a closed-loop fluid pathway 122.

Figure 30:
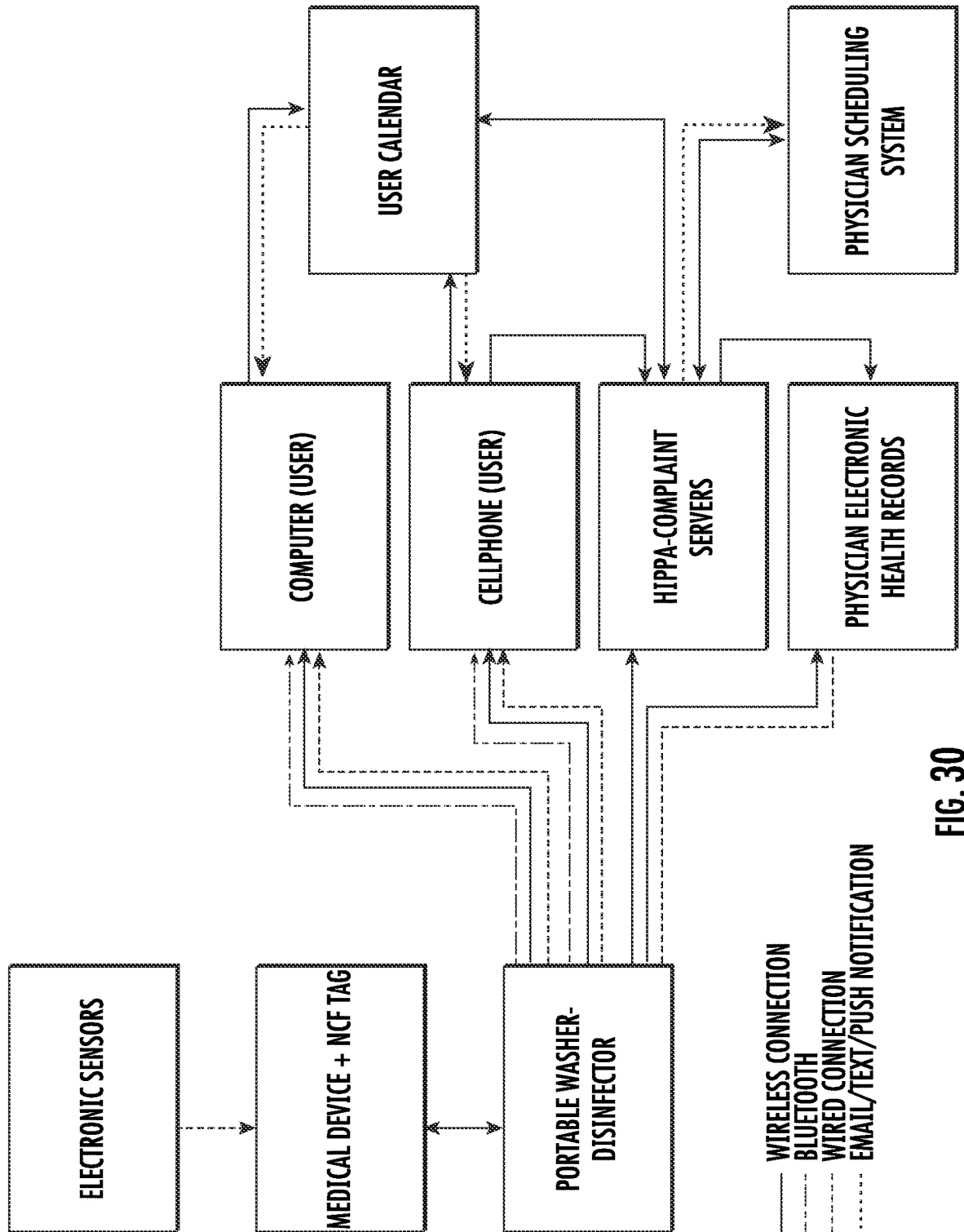
FIG. 30 illustrates a flow chart of an embodiment of a cleaning-disinfecting system representing the data flow through the cleaning-disinfecting system, medical devices, and other external sources according to one embodiment of the invention.

FIG. 30 illustrates another embodiment of the cleaning-disinfecting system 100 representing the data flow through the cleaning-disinfecting system 100, medical devices, and other external sources. Usage data relating but not limited to time of use and usage frequency of medical devices may be stored in the cleaning-disinfecting system's on-board memory for transmission via Bluetooth, Wi-Fi, or wired data connections to the user's computer, the user's cellphone, to private HIPAA-compliant company servers, or to the user's physician's electronic health records system. This data may also be utilized to streamline the reordering process of medical devices or supplies on a monthly, quarterly, or otherwise regular basis, minimizing the need for direct user interaction to place these orders. In yet another embodiment of the cleaning-disinfecting system 100, this usage data may also facilitate the analysis of the user's online calendar connected to the cleaning-disinfecting system 100 through user registration in order to book a medical visit through the user's registered physician's scheduling system for the renewal of prescriptions needed for the ordering of the medical device or supply in question. The cleaning-disinfecting system 100 may then issues an email, text, or push notification to the user's phone notifying them of the appointment. In yet another embodiment of the cleaning-disinfecting system 100, in lieu of directly making the appointment on the user's behalf, the cleaning-disinfecting system 100 may issue an email, text, or push notification to the user's phone that they need to schedule an appointment with their physician for the purposes of prescription renewal. In another embodiment of the cleaning-disinfecting system 100, the cleaning-disinfecting system 100 may issue a digital reminder to the physician to reorder or rewrite the user's prescription for the medical device that is reprocessed in the cleaning-disinfecting system 100. Preferably, the cleaning-disinfecting system 100 may provide the user with a survey or other data collection mechanism to ascertain whether or not any complications have arisen from the use of the medical device over the period for which the prescription is valid, and only sends the reminder to the physician if there have been minimal low-risk complications; otherwise the cleaning-disinfecting system 100 may schedule an appointment with the physician on the user's behalf or issues a push notification to the user in lieu of directly making an appointment.

In another embodiment, the RFID or NFC tag 162 on the medical device may contain data that is gathered during use of the medical device when it is inserted or otherwise interfaces with the user or recipient of the medical device. In this embodiment, the cleaning-disinfecting system 100 may be able to download the data onto its on-board system memory for transmission via Bluetooth, Wi-Fi, or wired data connection in a HIPAA-compliant fashion. In various embodiments, this data transmission may be affected to the user's computer, the user's cellphone, to private HIPAA-compliant company servers, or to the user's physician's electronic health records system. In yet other embodiments of the cleaning-disinfecting system 100, the data that is transferred to its on-board system via RFID or NFC scanning may be analyzed by the cleaning-disinfecting system's firmware or algorithms that analyze data stored on private HIPAA-compliant company servers for early warning signs of disease using machine learning algorithms. Following this analysis, the cleaning-disinfecting system 100 may alert the user through its human-computer interface, through push notifications to the user's phone, through text messages, through electronic mail, or through some other form of electronically-mediated communication. In other embodiments of the cleaning-disinfecting system 100, the cleaning-disinfecting system 100 may connect to the user's calendar and user's physician's scheduling system to automatically book an appointment for a check-up and detailed review of the data gathered by the medical device to facilitate early action and prevention of adverse medical outcomes.

Figure 31:
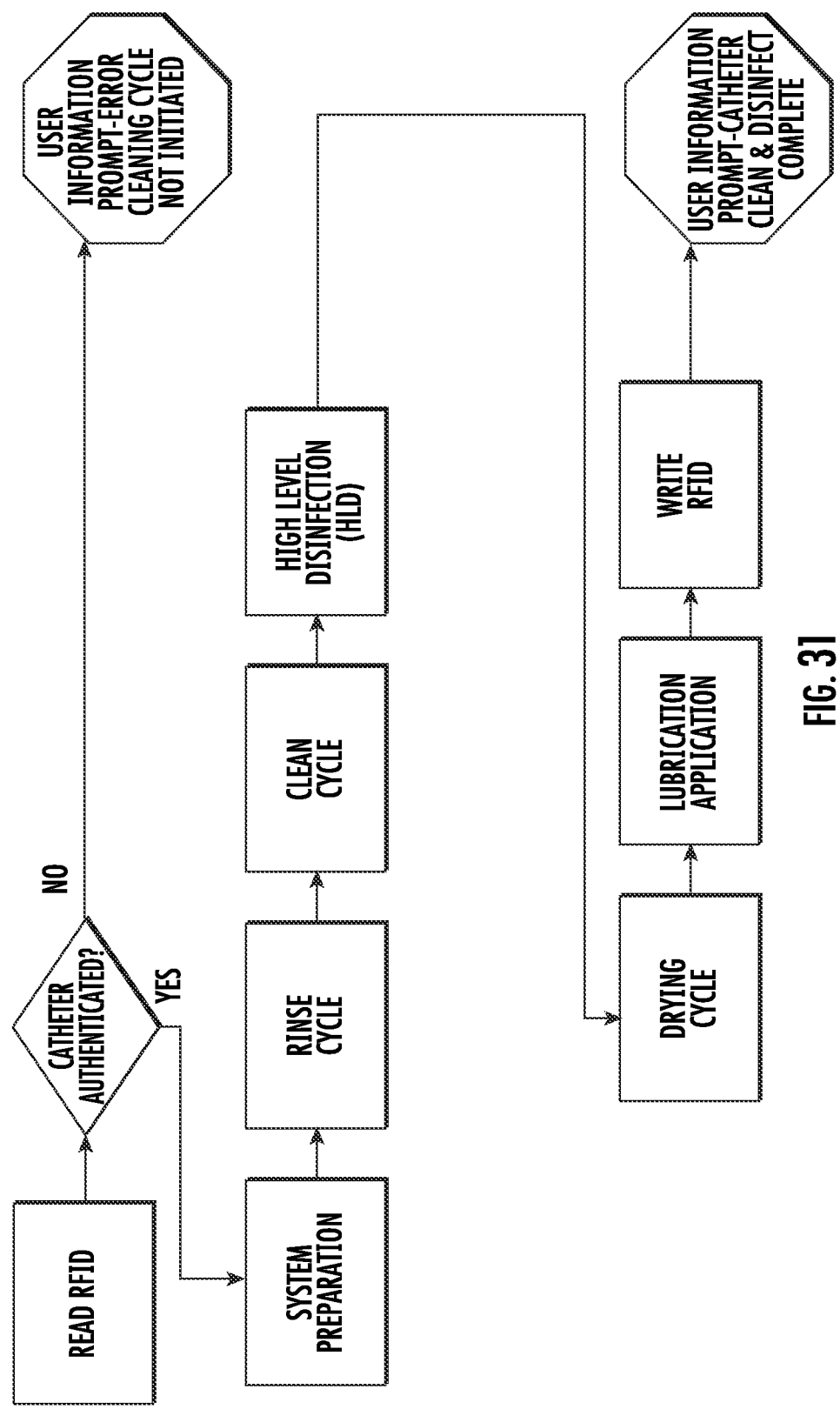
FIG. 31 illustrates a flow chart of an exemplary reprocessing cycle flow for the cleaning-disinfecting system according to one embodiment of the invention.

FIG. 31 illustrates a flow chart of an exemplary reprocessing cycle flow for the cleaning-disinfecting system 100. The devices, systems, and methods according to the cleaning-disinfecting system 100 preferably provide automated standardization for cleaning and disinfecting and/or sterilization in a manner that minimizes the need for operator input to reduce the risk of inadequate and/or inconsistent reprocessing. Another embodiment of the cleaning-disinfecting system 100 has the capability to actively monitor critical process parameters such as, but not limited to, concentration of reprocessing materials being circulated in and around the medical device, time elapsed, temperature of the system, and atmospheric pressure in order to dynamically change the length of the reprocessing process to ensure complete cleaning and disinfection of the medical device inserted into the cleaning-disinfecting system.

In another embodiment of the cleaning-disinfecting system 100, a valid RFID or NFC tag 162 must be scanned by a RFID/NFC scanner 160 and identified as a prerequisite to begin the reprocessing cycle. Otherwise the cleaning-disinfecting system 100 may display an error message to the user through a human-computer interface and does not begin the reprocessing cycle.

Preferred embodiments of the cleaning-disinfecting system 100 are portable. Preferably, the overall dimensions of the apparatus housing are: length of 5" to 18" (preferably 6" to 16"), height of 1.5" to 6" (preferably 1.5" to 5"), width of 1" to 6" (preferably 1.5" to 5").

The cleaning-disinfecting system 100 can be designed to be portable (both small and light) and easy to use. Preferably, the medical device is adapted for use by an individual (e.g., in the individual's home) and/or for common everyday use environments such as outdoors, while at work, or traveling. Preferably, the medical device is adapted for insertion into a patient (e.g., a catheter). Preferably, the medical device is adapted to be used by the patient. Preferably, the medical device is CLIA waived. Preferably, the medical device is adapted for home use. Preferably, the device does not require calibration or more than five steps to complete (e.g., open, insert medical product, close, sterilize and remove sterilized product).

According to other embodiments, the medical device is made from a material (e.g., plastic or glass). Preferably, the medical device comprises plastic or glass. More preferably, the medical device consists essentially of plastic or glass. Preferably, the medical device comprises a tube, more preferably a plastic tube. Preferably, the medical device is a tube having a length ranging between 4-18", preferably a length ranging between 5" to 16". Preferably, the medical device is flexible (e.g., capable of being bent).

According to other embodiments, the cleaning-disinfecting system 100 further comprises one or more operational status indicators, such as colored LEDs or a LED display, to indicate the operational state of the cleaning-disinfecting system 100.

According to other embodiments, the cleaning-disinfecting system 100 further comprises a transmitter and/or receiver for wireless communication protocols.

According to other embodiments, a battery for the cleaning-disinfecting system 100 may be charged wirelessly (e.g., wireless charging). According to preferred embodiments, the battery is charged with a regenerative charging method such triboelectric generation or solar photovoltaic charging (e.g., regenerative battery) or other methods known and used in the art.

According to other embodiments, a wireless transmitter from the cleaning-disinfecting system 100 transmits diagnostics in a HIPAA-compliant manner to relevant and authorized healthcare practitioners such as a primary care physician, urologist, occupational therapist, or registered nurse. Alternatively, the wireless transmitter transmits diagnostics to a telemedicine service (e.g., transmits diagnostics to urologist or telemedicine service). According to preferred embodiments, the wireless transmitter is able to transmit data to a central online repository to be viewed via a diagnostics dashboard. According to preferred embodiments, the wireless transmitter is able to transmit data to other local devices via near-field such as but not limited to RFID or wireless communication protocols such as but not limited to Bluetooth (e.g., transmit data to a diagnostics dashboard; communicates to other devices (Internet of Things—IoT)).

According to other embodiments, the cleaning-disinfecting system 100 is designed to be portable and easy to use by patients and/or caregivers. Specifically, the size, weight and overall design allows easy use. The cleaning-disinfecting system 100 may further comprise tabs and/or grips on the exterior of the cleaning-disinfecting system 100 to reduce slippage. The cleaning-disinfecting system 100 may further comprise a textured grip for the apparatus, even more preferably an ergonomic grip (e.g., configured to be gripped by a hand).

According to other embodiments, the cleaning-disinfecting system 100 may be configured to be carried, stored and used. The cleaning-disinfecting system 100 may further comprise an exterior bumper guard to protect the apparatus from falls and shocks.

According to other embodiments, the cleaning-disinfecting system 100 may include a remote control, such as a user's smartphone, used to monitor and control operation of the reprocessing cycles and the cleaning-disinfecting system 100 via wireless communication.

According to other embodiments, the cleaning-disinfecting system 100 may be adapted to be operated through a remote control. The remote control may be a cellular device (e.g., a smartphone). The remote control may be a personal computer. The cleaning-disinfecting system 100 may include personal identification information such as but not limited to name, address, phone number, preferably labeled on the exterior of the cleaning-disinfecting system 100.

According to one embodiment of the present invention, the power supply may be portable (e.g., a battery), may be internally housed, and, preferably, may be rechargeable. The power supply may provide energy to the cleaning-disinfecting system 100. In preferred embodiments, the cleaning-disinfecting system 100 may be adapted to be connected to an external power source via power cord (e.g., from a wall outlet) or docking station (e.g., a power cord).

According to one embodiment of the present invention, the cleaning-disinfecting system may be further adapted to have one or more components to be modular, allow maintenance and replacement by users or qualified technician.

Figure 32A:
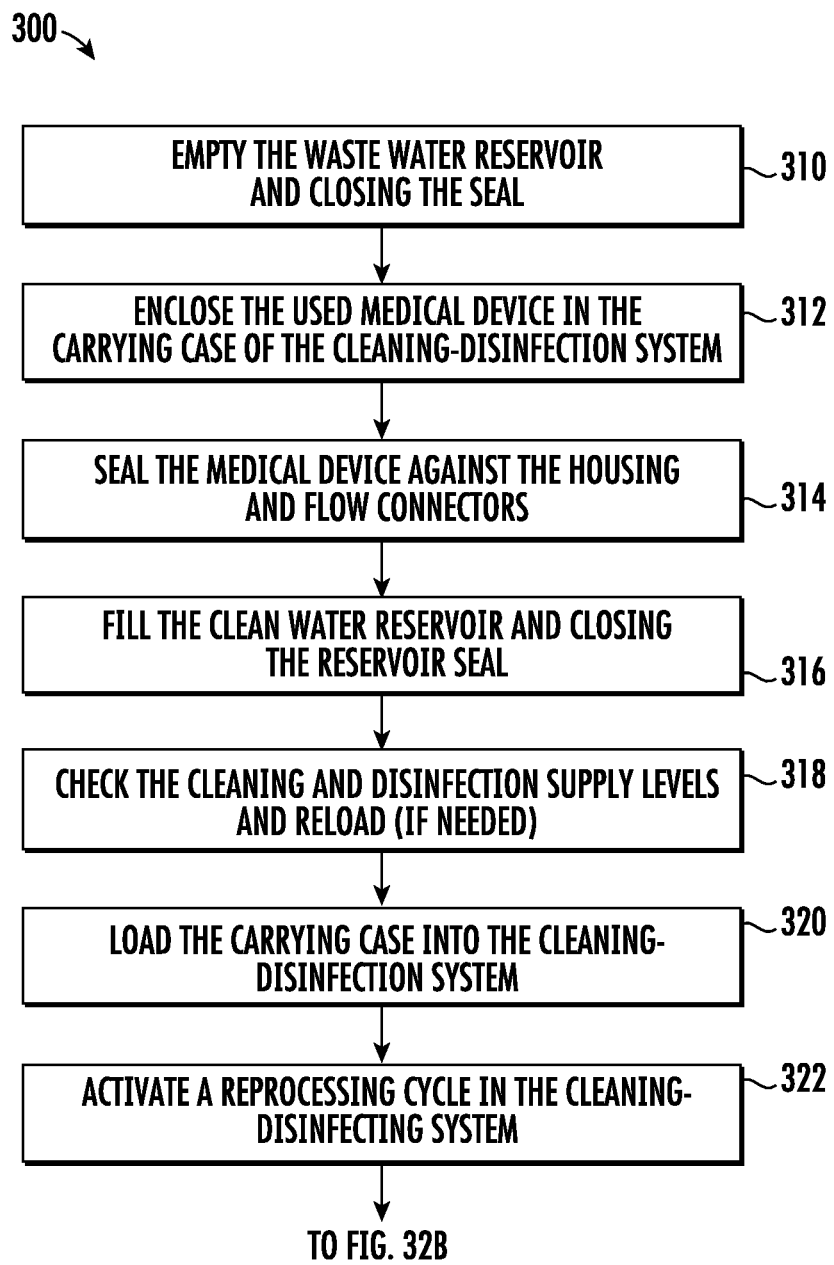
FIGS. 32A and 32B illustrate a method for reprocessing a medical device using a cleaning-disinfection system according to one embodiment of the invention.
Figure 32B:
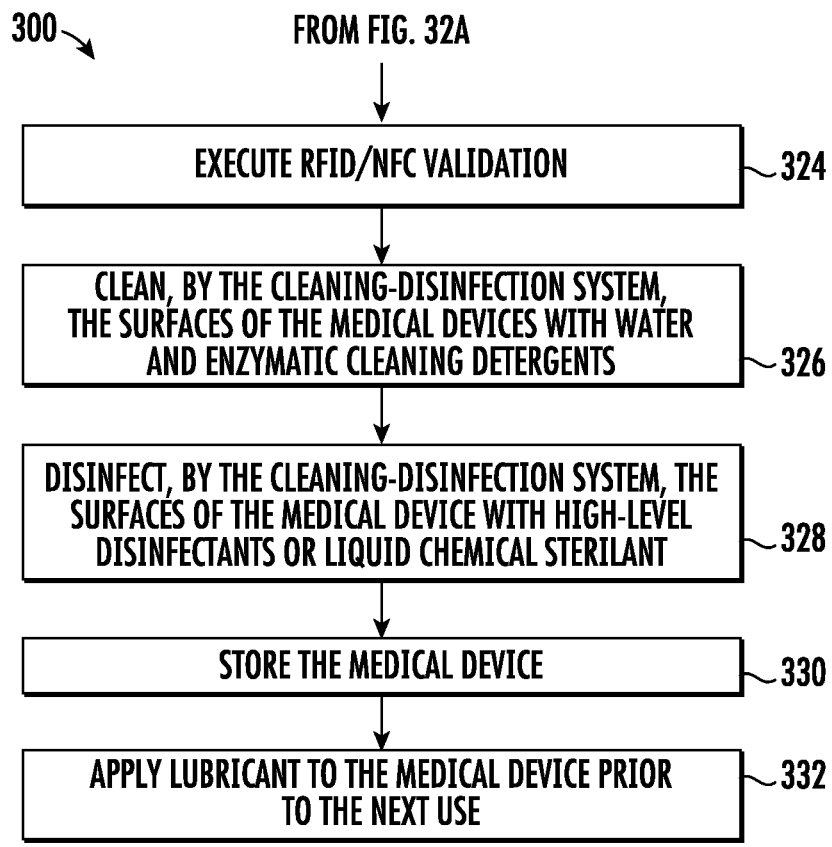

One embodiment of the invention, as illustrated in FIGS. 32A and 32B, relates to a method for reprocessing 300 a medical device using a cleaning-disinfection system 100 comprising: (a) emptying the waste water reservoir and closing the seal 310; (b) enclosing the used medical device in the carrying case of the cleaning-disinfection system 312; (c) sealing the medical device against the housings and flow connectors 314; (d) filling the clean water reservoir and closing the reservoir seal 316; (e) checking the cleaning and disinfectant supply levels and reloading (if needed) 318; (f) loading the carrying case into the cleaning-disinfection system 320; (g) activating a reprocessing cycle 322; (h) execute RFID/NVC validation 324; (i) cleaning, by the cleaning-disinfection system, the surfaces of the medical devices with water and enzymatic cleaning detergents 326; (j) disinfecting, by the cleaning-disinfection system, the surfaces of the medical device with high-level disinfectants or liquid chemical sterilant 328; (k) storing the medical device 330; and (l) applying lubricant to the medical device prior to the next use 332.

According to other embodiments, the method further comprises recharging the cleaning-disinfecting system 100 using a charging dock. According to preferred embodiments, the method further comprises downloading data from the cleaning-disinfecting system 100 to an external device.

According to preferred embodiments, the cleaning-disinfecting system 100 is configured to be used in a cleaning-disinfecting system 100 with at least one medical device, preferably an intermittent catheter. Preferably, the medical device is used in common everyday use environments such as outdoors, or in a home, or at work, or while traveling. Preferably, the medical device is adapted for insertion into a patient. Preferably, the medical device is adapted to be used by a patient. Preferably, the medical device is CLIA waived. Preferably, the medical device is adapted for home use. Preferably, the medical device is a plastic, more preferably consists essentially of plastic. Preferably, the medical device takes the form of a tube, preferably a flexible tube. In an embodiment, the medical device consists essentially of a flexible material, more preferably the medical device consists of a flexible material or is flexible.

In other embodiments, the method further comprises downloading data from the cleaning-disinfecting system 100 to an external device (e.g., a thumbdrive, a smartphone, laptop or other computer system). Preferably, the operational history is stored on local memory in the cleaning-disinfecting system 100 to be transmitted (via cable or wireless) to a computer or cellphone for a user or healthcare practitioner to monitor.

In accordance with other aspects of the present invention, the cleaning-disinfecting system 100 includes one or more RFID scanners 160 and modules that verify the authenticity of all medical devices placed within the cleaning-disinfecting system 100 for reprocessing through the scanning of RFID/NFC chips/tags 162 embedded in all of the aforementioned medical devices and writes information to the individual RFID/NFC chips/tags 162 in accordance with the number of times that the cleaning-disinfecting system 100 has been used to reprocess the medical devices. The RFID module may electronically interface with the microcontroller and/or logic board that controls the reprocessing cycle of the cleaning-disinfecting system 100 for reprocessing to prevent the reprocessing cycle if an individual has placed a RFID-embedded medical device that has been reprocessed more than a pre-specified number of times. The RFID module may also electronically interface with a suite of sensors through a microcontroller and/or logic board to ascertain whether or not a medical device lacking an RFID/NFC chip/tag 162 has been inserted into the cleaning-disinfecting system 100, and the microcontroller may prevent the reprocessing cycle until the medical device lacking an RFID/NFC chip/tag has been removed from the cleaning-disinfecting system 100.

In accordance with other aspects of the present invention, the cleaning-disinfecting system 100 may pair with an individual's mobile phone or personal computer or other such device to deliver usage statistics, detailed troubleshooting steps, status updates, as well as other data. This pairing may be further defined as enabling an individual to scan the RFID-embedded medical devices to verify their authenticity as well as observe the remaining number of reprocessing cycles possible for the scanned devices. This pairing may be further defined as enabling an individual to remotely control the cleaning-disinfecting system 100 through their mobile phone or personal computer or other such device.

In accordance with other aspects of the present invention, the cleaning-disinfecting system 100 may be configured to have a screen 150 on the cleaning-disinfecting system 100 in order to communicate to an individual using the cleaning-disinfecting system 100 the current status of a reprocessing cycle, or otherwise indicate the remaining longevity of the RFID-embedded medical devices that are being used in conjunction with and are being reprocessed by the cleaning-disinfecting system 100. The remaining longevity of the RFID-embedded medical devices may additionally be communicated to an individual via RGB LEDs corresponding to each individual medical device located on the cleaning-disinfecting system 100.

In accordance with other aspects of the present invention, the cleaning-disinfecting system 100 may be configured to be battery-powered and portable. The cleaning-disinfecting system 100 may pair with one or many cleaning-disinfecting systems to accurately track medical device usage and frequency.

Specifically, the medical device may include or be a catheter 130. According to aspects of this invention, the catheter 130 may be a urinary intermittent catheter, primarily fabricated from a UVC-transparent and flexible material with a stiff funnel fabricated from cyclic olefin copolymer or FEP, and intended to be inserted into the human body for 3-5 minutes at a time to facilitate the drainage of urine from the bladder into a receptacle. For males, the catheter 130B may likely be between 11.5 and 12 inches long (not including the funnel, which is itself 1 inch long); for females, the catheter 130A may likely be between 3 and 5 inches long (not including the funnel).

The catheter 130 may be tagged with an RFID/NFC chip/tag 162 that may be scanned upon placement into the cleaning-disinfecting system 100. The RFID/NFC chip/tag 162 may contain authentication information [e.g. serial number] as well as usage information [how many times that specific catheter 130 has been reprocessed]. This information may also include time and date of the last reprocessing. The catheter 130 may have the capability to perform real-time analysis of the bioburden present within the urine. Each of the electronic sensors used to perform this analysis would potentially store their readings in a separate RFID/NFC chip/tag 162 [e.g. an RFID array] or a single high-capacity RFID chip. The RFID/NFC chip/tag 162 present on the catheter 130 may also be scannable by mobile app and mobile phone RFID reader to validate the number of uses left in the catheter 130 and generally access the data remotely/in the absence of the cleaning-disinfecting system 100.

The cleaning-disinfecting system 100 may include a reprocessor control circuit. The reprocessor control circuit may provide a color-coded display for remaining uses. The cleaning-disinfecting system 100 may inform the user how many uses is left in each catheter 130. For example, the status indicator may shine green if the catheter 130 has been used less than 75 times each; yellow if the catheter 130 has been used between 75 and 95 times; and red if the catheter 130 has been used between 95 and 100 times. Other colors and usage times may be utilized without departing from this invention. The cleaning-disinfecting system 100 may include an LED pixel matrix that visually indicates to the user how much time is left in the reprocessing cycle.

The cleaning-disinfecting system 100 may include various software features. The cleaning-disinfecting system 100 may include an automated replenishment. For example, based on number of uses remaining in the catheter 130 used with the cleaning-disinfecting system 100, the cleaning-disinfecting system 100 can automatically initiate a catheter reorder with the user's medical device distributor. In another embodiment, the cleaning-disinfecting system 100 may include catheterization analysis. For example, the software may analyze the frequency of catheterization based on detection of catheter removal from the cleaning-disinfecting system 100 [RFID reader scans the cleaning-disinfecting system 100 every time the catheter 130 is removed] and frequency of reprocessing cycles. In another embodiment, the cleaning-disinfecting system 100 may include application pairing, where the cleaning-disinfecting system 100 may pair with a digital application on a mobile device to provide more detailed status updates and diagnostics of the cleaning-disinfecting system 100 to the user. The cleaning-disinfecting system 100 may use data gathered from the application [UTI incidence, urologist check-ups, etc.] to augment its analysis of the user's catheterization data. In another embodiment, the cleaning-disinfecting system 100 may include EHR integration to provide urologists with seamless, real-time updates on catheterization frequency and reprocessing analysis.

The cleaning-disinfecting system 100 may include a digital application for use with a mobile device. The digital application may be a companion application for the cleaning-disinfecting system 100 that features added functionality for the user. For example, the digital application may provide on-the-go validation and usage information, such that the application can scan each catheter 130 using the RFID/NFC technology in most mobile phones to validate authenticity and tell individuals how many uses they have left. In another embodiment, the digital application may include replenishment reminders and confirmation, such that the application can insert reminders in their calendar to re-order catheters from their distributor and update these reminders based on real-time usage of catheters. The application can additionally notify users of automated replenishment orders and ask for their consent before submitting the order for fulfillment. In another embodiment, the digital application may include location-based data gathering, such that using the application with location services enabled allows the application to ask individuals contextual questions. For example, if located near a hospital, the application may ask the user if they are experiencing UTI-like symptoms. Similar survey questions may be sent out periodically in the absence of location services to gather UTI-incidence data for analysis of catheterization habits and UTI incidence. The digital application may utilize anonymized data gathered across all users of the system and the application may suggest behavioral changes to limit UTI incidence.

Figure 33:
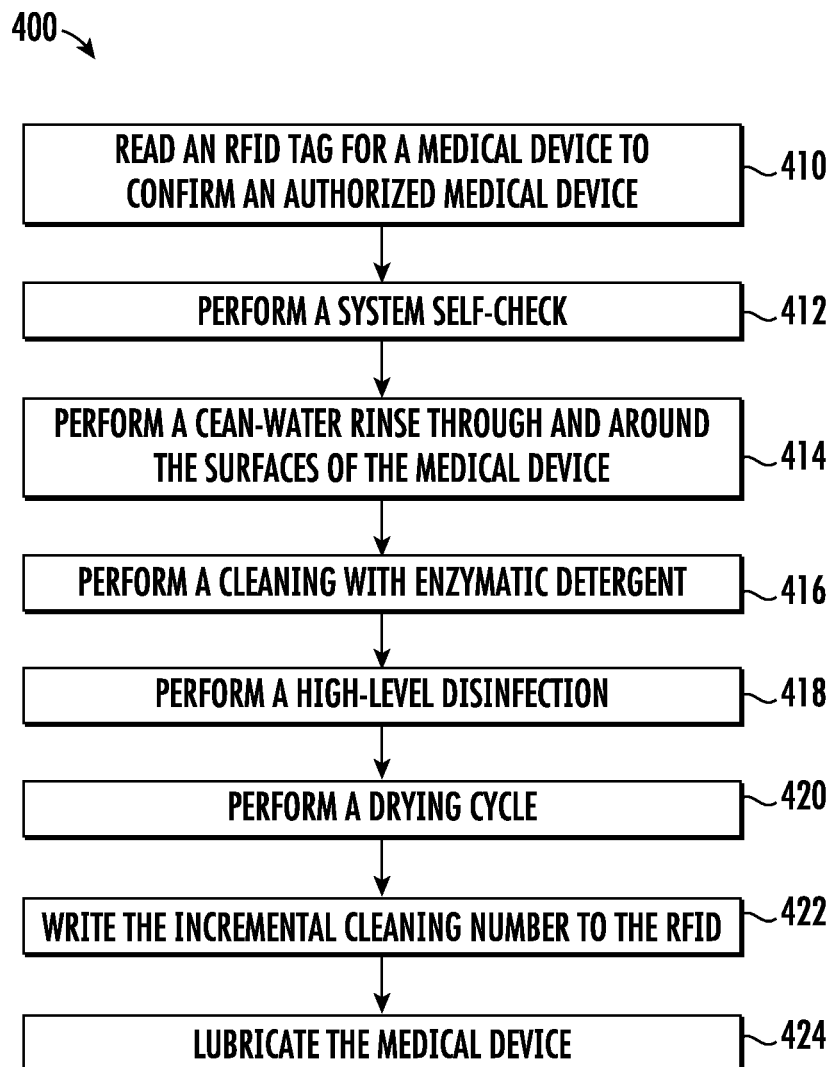
FIG. 33 illustrates another method for reprocessing a medical device using a cleaning-disinfection system according to one embodiment of the invention.

In another embodiment, as illustrated in FIG. 33, a method for reprocessing one or more medical devices 400 with RFID/NFC tags may include the steps of: (a) reading the medical device RFID/NFC tag to confirm authorized medical device 410; (b) performing a system self-check 412; (c) performing a clean-water rinse through and around the surfaces of the medical device 414; (d) performing a cleaning with enzymatic detergent 416; (e) performing a high-level disinfection 418; (f) performing a drying cycle 420; (g) writing the incremental cleaning number to the RFID 422; and (h) lubricating the medical device 424.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure, as well as for the purpose of restricting the claimed subject matter. It is also expressly noted that the dimensions and the shapes of the components shown in the figures are designed to help to understand how the present teachings are practiced, but not intended to limit the dimensions and the shapes shown in the examples.

Many illustrative embodiments are listed below in accordance with one or more aspects disclosed herein. Many of the embodiments listed below are described as depending from various embodiments and the dependencies are not limited and may be depending from any of the embodiments as is described and contemplated by this disclosure. Moreover, that any one or more of the listed embodiments may be incorporated into any of embodiments #1, #2, and #3 is contemplated by this disclosure.

Embodiment #1. A system for reprocessing one or more medical devices, the system comprising:
　a portable, medical device washer-disinfector to execute a reprocessing cycle with one or more medical devices, wherein the medical device washer-disinfector comprises:
　　a first housing with a first flow connector configured connect to a first end of the medical device, and
　　a second housing with a second flow connector configured to connect to a second end of the medical device, thereby creating a closed-loop fluid pathway for reprocessing fluids to flow through the one or more medical devices and the medical device washer-disinfector.

Embodiment #2. A medical device washer-disinfector to execute a reprocessing cycle with one or more medical devices, the medical device washer-disinfector comprising:
　a base unit and a detachable case configured to detach from the base unit, the detachable case includes a mounting tray configured to hold the one or more medical devices and a lid that provides access to the mounting tray;
　a first housing with a first flow connector configured connect to a first end of the medical device;
　a second housing with a second flow connector configured to connect to a second end of the medical device, thereby creating a closed-loop fluid pathway for reprocessing fluids to flow through the one or more medical devices and the medical device washer-disinfector; and
　an RFID/NFC system that includes an RFID/NFC scanner located within the medical device washer-disinfector that is configured to scan an RFID/NFC tag located within the one or more medical devices.

Embodiment #3. A method for reprocessing one or more medical devices, the method comprising:
　enclosing a medical device in a cleaning-disinfection system, wherein the cleaning-disinfection system includes a portable, medical device washer-disinfector to execute a reprocessing cycle with one or more medical devices, wherein the medical device washer-disinfector comprises:
　　a first housing with a first flow connector configured connect to a first end of the medical device, and
　　a second housing with a second flow connector configured to connect to a second end of the medical device, thereby creating a closed-loop fluid pathway for reprocessing fluids to flow through the one or more medical devices and the medical device washer-disinfector
　sealing the first end of the medical device against the first housing and first flow connector;
　sealing the second end of the medical device against the second housing and the second flow connector;
　filling with water a clean water reservoir connected to the closed-loop fluid pathway;
　activating a reprocessing cycle for the medical device washer-disinfector;
　cleaning, by the medical device washer-disinfector, surfaces of the medical device with water and enzymatic cleaning detergents; and
　disinfecting, by the medical device washer-disinfector, the surfaces of the medical device with high-level disinfectants or a liquid chemical sterilant.

Embodiment #4. The system for reprocessing one or more medical devices of any of the preceding Embodiments, wherein the medical device washer-disinfector further comprises a base unit and a detachable case configured to detach from the base unit, the detachable case includes a mounting tray configured to hold the one or more medical devices and a lid that provides access to the mounting tray.

Embodiment #5. The system for reprocessing one or more medical devices of any of the preceding Embodiments, wherein the medical device washer-disinfector includes a cleaning supply reservoir connected to the closed-loop fluid pathway.

Embodiment #6. The system for reprocessing one or more medical devices of any of the preceding Embodiments, wherein the cleaning supply reservoir holds one or more of: enzymatic cleaners, high-level disinfectants, or liquid chemical sterilant.

Embodiment #7. The system for reprocessing one or more medical devices of any of the preceding Embodiments, wherein the cleaning supply reservoir holds concentrated disinfectants or sterilants that are automatically diluted with water to a predetermined concentration for use in reprocessing the medical device through the use of a dosing pump.

Embodiment #8. The system for reprocessing one or more medical devices of any of the preceding Embodiments, wherein the medical device washer-disinfector includes a heating element to increase a temperature of the reprocessing fluids in the closed-loop fluid pathway in the cleaning-disinfecting system.

Embodiment #9. The system for reprocessing one or more medical devices of any of the preceding Embodiments, wherein the medical device washer-disinfector includes a water storage system connected to the closed-loop fluid pathway.

Embodiment #10. The system for reprocessing one or more medical devices of any of the preceding Embodiments, wherein the water storage system includes a clean water reservoir connected to the closed-loop fluid pathway, wherein the clean water reservoir holds one or more of: distilled water, deionized water, or purified water.

Embodiment #11. The system for reprocessing one or more medical devices of any of the preceding Embodiments, wherein the medical device washer-disinfector includes a water filter connected to the water storage system and the closed-loop fluid pathway, wherein tap water flows through the water filter and the water filter filters out water-borne pathogens.

Embodiment #12. The system for reprocessing one or more medical devices of any of the preceding Embodiments, wherein the water storage system includes a waste water reservoir connected to the closed-loop fluid pathway.

Embodiment #13. The system for reprocessing one or more medical devices of any of the preceding Embodiments, wherein the medical device washer-disinfector includes a lubrication system with a primary lubricant pump connected to the closed-loop fluid pathway to apply a lubricant to the medical device after the completion of the reprocessing cycle.

Embodiment #14. The system for reprocessing one or more medical devices of any of the preceding Embodiments, wherein the lubricant system includes a lubricant reservoir to store the lubricant.

Embodiment #15. The system for reprocessing one or more medical devices of any of the preceding Embodiments, wherein the medical device washer-disinfector includes a lubricant and a cleaning supply that are packaged into a single combined package.

Embodiment #16. The system for reprocessing one or more medical devices of any of the preceding Embodiments, wherein the medical device washer-disinfector applies a replenishment hydrophilic coating to the medical device.

Embodiment #17. The system for reprocessing one or more medical devices of any of the preceding Embodiments, further comprising:
an RFID/NFC system that includes an RFID/NFC scanner located within the medical device washer-disinfector that is configured to scan an RFID/NFC tag located within the one or more medical devices, wherein the RFID/NFC scanner scans the RFID/NFC tag when the one or more medical devices is loaded into the medical device washer-disinfector in the proper orientation, wherein the RFID/NFC system facilitates an identification of the medical device as suitable to be reprocessed within the medical device washer-disinfector and a prevention of reprocessing of the medical device that is not intended to be reprocessed within the medical device washer-disinfector.

Embodiment #18. The system for reprocessing one or more medical devices of any of the preceding Embodiments, wherein the RFID/NFC system tracks a number of times the medical device has been reprocessed with the medical device washer-disinfector by writing to RFID/NFC tag after every successful reprocessing.

Embodiment #19. The system for reprocessing one or more medical devices of any of the preceding Embodiments, wherein the RFID/NFC system includes a database that stores one or more of: various reprocessing cycles, material requirements for the medical devices, the medical devices, a history of reprocessing cycles, or a history of medical devices used with the medical device washer-disinfector.

Embodiment #20. The system for reprocessing one or more medical devices of any of the preceding Embodiments, further comprising:
an internal control circuit for controlling the reprocessing cycle with software, the internal control circuit includes a scanner to scan the one or more medical devices and a plurality of sensors that validate the lid is completely closed during the reprocessing cycle, prevent disinfection of non-system components by recognizing an absence of a valid scan on the non-system components and preventing activation of the reprocessing cycle, wherein the medical device washer-disinfector is registered to accept a placement of the one or more medical devices in a specific orientation to enable each medical device to be scanned by the scanner within the medical device washer-disinfector.

Embodiment #21. The system for reprocessing one or more medical devices of any of the preceding Embodiments, wherein the internal control circuit and the scanner validates an authenticity and a remaining longevity of each one of the one or more medical devices placed within the medical device washer-disinfector in order to begin the reprocessing cycle and writes data to a data-storage tag in each of the one or more medical devices following a successful completion of the reprocessing cycle.

Embodiment #22. The system for reprocessing one or more medical devices of any of the preceding Embodiments, wherein the medical device washer-disinfector is battery-powered.

Embodiment #23. The system for reprocessing one or more medical devices of any of the preceding Embodiments, further comprising:
a cleaning supply reservoir connected to the closed-loop fluid pathway, wherein the cleaning supply reservoir holds one or more of: enzymatic cleaners, high-level disinfectants, or liquid chemical sterilant.

Embodiment #24. The system for reprocessing one or more medical devices of any of the preceding Embodiments, further comprising:
a water storage system connected to the closed-loop fluid pathway,
wherein the water storage system includes a clean water reservoir connected to the closed-loop fluid pathway, and the clean water reservoir holds one or more of: distilled water, deionized water, or purified water, and
further wherein the water storage system includes a waste water reservoir connected to the closed-loop fluid pathway.

Embodiment #25. The system for reprocessing one or more medical devices of any of the preceding Embodiments, further comprising:

a lubrication system with a primary lubricant pump connected to the closed-loop fluid pathway to apply a lubricant to the medical device after the completion of the reprocessing cycle, wherein the lubricant system includes a lubricant reservoir to store the lubricant.

Embodiment #26. The system for reprocessing one or more medical devices of any of the preceding Embodiments, wherein the RFID/NFC scanner scans the RFID/NFC tag when the one or more medical devices is loaded into the medical device washer-disinfector in the proper orientation, wherein the RFID/NFC system facilitates an identification of the medical device as suitable to be reprocessed within the medical device washer-disinfector and a prevention of reprocessing of the medical device that is not intended to be reprocessed within the medical device washer-disinfector.

Embodiment #27. The system for reprocessing one or more medical devices of any of the preceding Embodiments, further comprising:
storing the medical device within the medical device washer-disinfector; and
applying a lubricant to the medical device prior to the next use.

Embodiment #28. The system for reprocessing one or more medical devices of any of the preceding Embodiments, further comprising:
scanning and reading, by an RFID/NFC scanner located within the medical device washer-disinfector, an RFID/NFC tag on the medical device to confirm an authorized medical device for the medical device washer-disinfector; and
after the reprocessing cycle is complete, writing an incremental cleaning number to the RFID/NFC tag on the medical device.

Embodiment #29. The system for reprocessing one or more medical devices of any of the preceding Embodiments, further comprising:
filling a waste water reservoir connected to the closed-loop fluid pathway during the execution of the reprocessing cycle.

Embodiment #30. The system for reprocessing one or more medical devices of any of the preceding Embodiments, wherein the lubrication system includes a secondary pump to apply the lubricant to one or more regions of the reprocessed medical device that are inaccessible using the primary lubricant pump.

Embodiment #31. The system for reprocessing one or more medical devices of any of the preceding Embodiments, wherein the lubricant is sterilized or disinfected using an UV diode with germicidal capabilities.

Embodiment #32. The system for reprocessing one or more medical devices of any of the preceding Embodiments, wherein the lubrication system is configurable for an amount of the lubricant applied to the medical device.

Embodiment #33. The system for reprocessing one or more medical devices of any of the preceding Embodiments, wherein the lubrication system is configurable to mix additives into the lubricant.

Embodiment #34. The system for reprocessing one or more medical devices of any of the preceding Embodiments, wherein the lubrication system circulates a polymer substrate that coats the medical device throughout the closed-loop fluid pathway prior to exposing the medical device to a polymerization agent that polymerizes the polymer substrate to a surface of the medical device.

Embodiment #35. The system for reprocessing one or more medical devices of any of the preceding Embodiments, wherein the lubrication system circulates a polymer substrate that has lubricious or antimicrobial properties.

Embodiment #36. The system for reprocessing one or more medical devices of any of the preceding Embodiments, wherein the medical device washer-disinfector includes a bioburden sensor that detects bioburden present on the medical device that is being reprocessed in real-time.

Embodiment #37. The system for reprocessing one or more medical devices of any of the preceding Embodiments, wherein the medical device washer-disinfector executes a direct analysis of a surface of the medical device for bioburden.

Embodiment #38. The system for reprocessing one or more medical devices of any of the preceding Embodiments, wherein the medical device washer-disinfector executes an analysis of extracted materials using rinse water and UV spectrophotometry.

Embodiment #39. The system for reprocessing one or more medical devices of any of the preceding Embodiments, wherein the medical device washer-disinfector includes an on-board memory and database that stores use and usage frequency data for the one or more medical devices.

Embodiment #40. The system for reprocessing one or more medical devices of any of the preceding Embodiments, wherein the medical device washer-disinfector transmits the use and usage frequency data via one of: Bluetooth, wi-fi, or wired connections.

Embodiment #41. The system for reprocessing one or more medical devices of any of the preceding Embodiments, wherein the medical device washer-disinfector transmits the use and usage frequency data to and from one or more of: a user's computer, a user's phone, one or more private HIPAA-compliant servers, or a user's physician's electronic health records system.

Embodiment #42. The system for reprocessing one or more medical devices of any of the preceding Embodiments, wherein the use and usage frequency data is used for a reordering process of medical devices and/or supplies on a monthly, quarterly, or regular basis.

Embodiment #43. The system for reprocessing one or more medical devices of any of the preceding Embodiments, wherein the use and usage frequency data is used to facilitate analysis of a user's online calendar connected to the medical device washer-disinfector to automatically schedule an appointment for a medical visit through a user's registered physician's scheduling system for a renewal of prescriptions needed.

Embodiment #44. The system for reprocessing one or more medical devices of any of the preceding Embodiments, wherein the medical device washer-disinfector sends an email, text, or push notification to the user's phone notifying the user of the appointment for the medical visit.

Embodiment #45. The system for reprocessing one or more medical devices of any of the preceding Embodiments, wherein the use and usage frequency data triggers the medical device washer-disinfector to send a notification (email, text, or push notification) a need to schedule an appointment for a medical visit for the renewal of prescriptions needed.

Embodiment #46. The system for reprocessing one or more medical devices of any of the preceding Embodiments, wherein RFID/NFC tag on the medical device contains medical use data gathered during the use of the medical device.

Embodiment #47. The system for reprocessing one or more medical devices of any of the preceding Embodiments, wherein the medical device washer-disinfector downloads the medical use data onto an on-board system memory and/or database for transmission via one of: Bluetooth, Wi-Fi, or wired connection in a HIPAA-compliant fashion.

Embodiment #48. The system for reprocessing one or more medical devices of any of the preceding Embodiments, wherein the medical device washer-disinfector transmits the medical use data to and from one or more of: a user's computer, a user's phone, one or more private HIPAA-compliant servers, or a user's physician's electronic health records system.

Embodiment #49. The system for reprocessing one or more medical devices of any of the preceding Embodiments, wherein the medical device washer-disinfector analyzes the medical use data for early warning signs of disease using machine learning algorithms.

Embodiment #50. The system for reprocessing one or more medical devices of any of the preceding Embodiments, wherein the medical device washer-disinfector alerts the user through one or more of: a human-computer interface, push notifications, text messages, or email.

Embodiment #51. The system for reprocessing one or more medical devices of any of the preceding Embodiments, wherein the medical device washer-disinfector uses the medical use data to facilitate analysis of a user's online calendar connected to the medical device washer-disinfector to automatically schedule a medical visit through a user's registered physician's scheduling system for an appointment for a check-up and detailed review of the medical use data—facilitating early action and prevention of adverse medical outcomes.

Embodiment #52. The system for reprocessing one or more medical devices of any of the preceding Embodiments, wherein the medical device washer-disinfector disinfects multiple medical devices simultaneously.

Embodiment #53. The system for reprocessing one or more medical devices of any of the preceding Embodiments, wherein the medical device washer-disinfector automatically reprocesses medical devices placed within the medical device washer-disinfector with a valid RFID/NFC scan and based on the type of medical device that is inserted into the medical device washer-disinfector.

Embodiment #54. The system for reprocessing one or more medical devices of any of the preceding Embodiments, wherein the medical device washer-disinfector stores the medical device after reprocessing without exposing the medical device to potential contamination from the environment.

Embodiment #55. The system for reprocessing one or more medical devices of any of the preceding Embodiments, wherein the medical device washer-disinfector monitors one or more critical process parameters to dynamically change a length of the reprocessing cycle to ensure complete cleaning and disinfection of the medical device.

Embodiment #56. The system for reprocessing one or more medical devices of any of the preceding Embodiments, wherein the one or more critical process parameters includes one or more of the following: a concentration of reprocessing materials being circulated in and around the medical device, reprocessing time elapsed, temperature of the closed-loop fluid pathway, or atmospheric pressure.

Embodiment #57. The system for reprocessing one or more medical devices of any of the preceding Embodiments, wherein the medical device washer-disinfector determines an optimal reprocessing endpoint for the medical device and dynamically updates the one or more process parameters to reach the optimal reprocessing endpoint.

Embodiment #58. The system for reprocessing one or more medical devices of any of the preceding Embodiments, wherein the medical device washer-disinfector further includes an ultrasonic wave transducer that transmits ultrasonic waves to create cavitation bubbles that collapse with high energy and remove soils from the surfaces of the medical device or supplies.

Embodiment #59. The system for reprocessing one or more medical devices of any of the preceding Embodiments, wherein the ultrasonic wave transducer transmits the ultrasonic waves at 20-40 kHz.

Embodiment #60. The system for reprocessing one or more medical devices of any of the preceding Embodiments, wherein the medical device washer-disinfector further includes concentrated enzymatic cleaners that are diluted with water and circulated through and around the medical device for a period of time sufficient to remove soils from the surfaces of the medical device.

Embodiment #61. The system for reprocessing one or more medical devices of any of the preceding Embodiments, wherein the medical device washer-disinfector further utilizes UV light with germicidal wavelengths of light to disinfect or sterilize medical devices.

Embodiment #62. The system for reprocessing one or more medical devices of any of the preceding Embodiments, wherein when the medical device is inserted into the medical device washer-disinfector, the medical device interfaces with the medical device washer-disinfector forming a water-tight seal and/or an air-tight seal.

Embodiment #63. The system for reprocessing one or more medical devices of any of the preceding Embodiments, wherein the water-tight seal and/or the air-tight seal creates a closed-loop fluid pathway with the reprocessing fluids.

Embodiment #64. The system for reprocessing one or more medical devices of any of the preceding Embodiments, wherein the medical device washer-disinfector further includes a pump that circulates the reprocessing fluids, wherein the pump is one of a diaphragm pump or a peristaltic pump.

Embodiment #65. The system for reprocessing one or more medical devices of any of the preceding Embodiments, wherein the medical device is loaded into the medical device washer-disinfector in an orientation of the medical device to facilitate the flow of the reprocessing fluid through the medical device to minimize an amount of air trapped in the closed-loop fluid pathway.

Embodiment #66. The system for reprocessing one or more medical devices of any of the preceding Embodiments, wherein orientation of the medical device is one or more of the following: a straight orientation, an u-shaped orientation, a looped orientation, or a coiled orientation.

Embodiment #67. The system for reprocessing one or more medical devices of any of the preceding Embodiments, wherein the medical device and/or the first and second housings include one or more magnets to seat the medical device into the medical device washer-disinfector.

Embodiment #68. The system for reprocessing one or more medical devices of any of the preceding Embodiments, wherein the one or more magnets are an asymmetric array of magnets to prevent twisting or otherwise disadvantageous positioning of the medical device in the medical device washer-disinfector.

Embodiment #69. The system for reprocessing one or more medical devices of any of the preceding Embodiments, wherein the one or more magnets are an asymmetric array of magnets to prevent damage the medical device.

Embodiment #70. The system for reprocessing one or more medical devices of any of the preceding Embodiments, wherein the one or more magnets are an asymmetric array of magnets to prevent the incomplete cleaning and/or disinfection of the medical device within the medical device washer-disinfector.

Embodiment #71. The system for reprocessing one or more medical devices of any of the preceding Embodiments, wherein the medical device includes one or more magnets and/or ferrous metal to interface with a magnetically-augmented loading mechanism in the first housing and the second housing into the medical device washer-disinfector.

Embodiment #72. The system for reprocessing one or more medical devices of any of the preceding Embodiments, wherein the medical device washer-disinfector further includes a spring-loaded, dynamic, and/or static locking structure to compress the medical device within the medical device washer-disinfector to create the water-tight and/or air-tight seal.

Embodiment #73. The system for reprocessing one or more medical devices of any of the preceding Embodiments, wherein the medical device washer-disinfector further includes an electronic interface that charges an on-board battery for the medical device.

Embodiment #74. The system for reprocessing one or more medical devices of any of the preceding Embodiments, wherein the electronic interface is a wireless charging interface that charges the on-board battery for the medical device.

Embodiment #75. The system for reprocessing one or more medical devices of any of the preceding Embodiments, wherein a proximal end of the medical device which enters the user's body when being used, faces against a flow of the reprocessing fluid in the closed-loop fluid pathway of the medical device washer-disinfector.

Embodiment #76. The system for reprocessing one or more medical devices of any of the preceding Embodiments, wherein a proximal end of the medical device faces inline with the flow of the reprocessing fluid in the closed-loop fluid pathway of the medical device washer-disinfector.

Embodiment #77. The system for reprocessing one or more medical devices of any of the preceding Embodiments, wherein the medical device is a reusable urinary intermittent catheter.

Embodiment #78. The system for reprocessing one or more medical devices of any of the preceding Embodiments, wherein the reusable urinary intermittent catheter includes a catheter tube configured to be inserted into a male or female urethral tract to facilitate drainage of urine from a bladder into a receptacle.

Embodiment #79. The system for reprocessing one or more medical devices of any of the preceding Embodiments, wherein the catheter tube includes a catheter channel to allow reprocessing fluids to flow into an annular space between an insertion sleeve and the catheter tube and the reprocessing fluids flow out through an introducer tip/insertion aid without dead ends or pressure build-ups.

Embodiment #80. The system for reprocessing one or more medical devices of any of the preceding Embodiments, wherein the catheter tube includes fluid channels in both a proximal end and a distal end of the medical device, wherein the reprocessing fluids circulate throughout the medical device.

Embodiment #81. The system for reprocessing one or more medical devices of any of the preceding Embodiments, wherein the fluid channels allow the flow of the reprocessing fluids to ensure sufficient contact with patient-contacting surfaces to ensure the adequate cleaning and disinfection of the medical device.

Embodiment #82. The system for reprocessing one or more medical devices of any of the preceding Embodiments, wherein the medical device includes integrated o-rings to form the water-tight and air-tight seal with the closed-loop fluid pathway of the medical device washer-disinfector.

Embodiment #83. The system for reprocessing one or more medical devices of any of the preceding Embodiments, wherein the catheter tube is coated with an antimicrobial coating, wherein the coating prevents deposition or growth of pathogens on the surface of the medical device.

Embodiment #84. The system for reprocessing one or more medical devices of any of the preceding Embodiments, wherein the antimicrobial coating is attached to the medical device to preserve a user's ability to reuse the medical device.

Embodiment #85. The system for reprocessing one or more medical devices of any of the preceding Embodiments, wherein the reusable urinary intermittent catheter includes a funnel connected to the catheter tube.

Embodiment #86. The system for reprocessing one or more medical devices of any of the preceding Embodiments, wherein the reusable urinary intermittent catheter includes one or more near-field communication (NFC) (or RFID) tags embedded in the catheter that contain authentication information and validate the authentication information and usage information, wherein the usage information includes number of sterilizations and a time and date of each sterilization and the one or more NFC tags store a remaining longevity of the catheter based on the usage information.

Embodiment #87. The system for reprocessing one or more medical devices of any of the preceding Embodiments, wherein the reusable urinary intermittent catheter includes flexible sensors that gather diagnostic data during the use of the medical device.

Embodiment #88. The system for reprocessing one or more medical devices of any of the preceding Embodiments, wherein the one or more RFID/NFC tags save the diagnostic data onto the RFID/NFC tag on the medical device for later transfer to the medical device washer-disinfector.

Embodiment #89. The system for reprocessing one or more medical devices of any of the preceding Embodiments, wherein the flexible sensors are powered by an on-board battery.

Embodiment #90. The system for reprocessing one or more medical devices of any of the preceding Embodiments, wherein the medical device is an urinary intermittent catheter.

Embodiment #91. The system for reprocessing one or more medical devices of any of the preceding Embodiments, wherein the urinary intermittent catheter includes a catheter insertion aid configured to mate with the urinary intermittent catheter with a catheter tube to be inserted into a female urethra to facilitate drainage of urine from a bladder into a receptacle Embodiment #92. The system for reprocessing one or more medical devices of any of the preceding Embodiments, wherein the catheter insertion aid comprises an insertion tip located at a proximal end of the catheter insertion aid.

Embodiment #93. The system for reprocessing one or more medical devices of any of the preceding Embodiments, wherein the catheter insertion aid comprises a physical interface for a user to hold and support the insertion aid against the body using one or more fingers when inserting the catheter tube into the female urethra.

Embodiment #94. The system for reprocessing one or more medical devices of any of the preceding Embodiments, wherein the catheter insertion aid comprises a detachable mirror on a funnel end to enhance line of sight to urethral opening.

Embodiment #95. The system for reprocessing one or more medical devices of any of the preceding Embodiments, wherein the detachable mirror includes an LED light to illuminate the urethral opening.

Embodiment #96. The system for reprocessing one or more medical devices of any of the preceding Embodiments, wherein the detachable mirror includes a magnifying and/or convex mirror.

Embodiment #97. The system for reprocessing one or more medical devices of any of the preceding Embodiments, wherein the catheter insertion aid comprises a spreader with a clamshell structure intended for insertion between the labia for touchless labial spreading.

Embodiment #98. The system for reprocessing one or more medical devices of any of the preceding Embodiments, wherein the spreader includes a spring-loaded mechanism or manual actuation.

Embodiment #99. The system for reprocessing one or more medical devices of any of the preceding Embodiments, wherein the spreader includes opening action that advances the catheter introducer tip forward via an internal tooth and lip mechanism.

Embodiment #100. The system for reprocessing one or more medical devices of any of the preceding Embodiments, wherein the catheter insertion aid comprises an adjustable handle that facilitates accurate catheter insertion via physical leverage against the pubic bone.

Embodiment #101. The system for reprocessing one or more medical devices of any of the preceding Embodiments, wherein the catheter insertion aid comprises caps located at either end of the medical device to prevent the leakage of the reprocessing fluids from the medical device after the medical device is removed from the medical device washer-disinfector.

Embodiment #102. The system for reprocessing one or more medical devices of any of the preceding Embodiments, wherein the caps include one-way valves to allow for the flow of reprocessing fluids through the caps during the reprocessing cycle.

Embodiment #103. The system for reprocessing one or more medical devices of any of the preceding Embodiments, wherein the caps are connected to the medical devices via one or more attachment mechanism, such as magnets, hinges (living, mechanical, etc), or other attachment mechanisms.

The scope of the present devices, systems and methods, etc., includes both means plus function and step plus function concepts. However, the claims are not to be interpreted as indicating a "means plus function" relationship unless the word "means" is specifically recited in a claim, and are to be interpreted as indicating a "means plus function" relationship where the word "means" is specifically recited in a claim. Similarly, the claims are not to be interpreted as indicating a "step plus function" relationship unless the word "step" is specifically recited in a claim, and are to be interpreted as indicating a "step plus function" relationship where the word "step" is specifically recited in a claim.

It is understood that the embodiments described herein are for the purpose of elucidation and should not be considered limiting the subject matter of the disclosure. Various modifications, uses, substitutions, combinations, improvements, methods of productions without departing from the scope or spirit of the present invention would be evident to a person skilled in the art.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. Additionally, the terms "first," "second," "third," and "fourth" as used herein are intended for illustrative purposes only and do not limit the embodiments in any way. Further, the term "plurality" as used herein indicates any number greater than one, either disjunctively or conjunctively, as necessary, up to an infinite number.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the spirit of the invention and the scope of protection is only limited by the scope of the accompanying Claims.

We claim:

1. A system for reprocessing one or more medical devices, the system comprising:
   a portable, medical device washer-disinfector to execute a reprocessing cycle with one or more medical devices, wherein the medical device washer-disinfector is personal, hand-held, and used by a user while being carried, the medical device washer-disinfector comprises:
   a base unit that houses a set of fluid components, a set of electronics, and a power supply to enable operation of the portable, medical device washer-disinfector,
   a detachable case configured to detach from the base unit, wherein the detachable case includes a mounting tray configured to hold the one or more medical devices and a lid that provides access to the mounting tray, wherein the detachable case provides the user access to the medical device, an ability to refill input water and drain waste water from a previous cycle, and can reattach to the base unit with a water- and air-tight seal,
   a first housing located within the detachable case, with a first flow connector configured connect to a first end of the medical device, and
   a second housing located within the detachable case, with a second flow connector configured to connect to a second end of the medical device, thereby creating a closed-loop fluid pathway for reprocessing fluids to flow through the one or more medical devices and the medical device washer-disinfector, wherein the reprocessing fluids are fully contained within the first flow connector, the second flow connector, and the medical device,
   wherein an interface between the first flow connector and the second flow connector and the first end and the second end of the medical device provides a water-tight and air-tight seal forming the closed-loop fluid pathway.

2. The system of claim 1, wherein the medical device washer-disinfector includes a cleaning supply reservoir connected to the closed-loop fluid pathway.

3. The system of claim 2, wherein the cleaning supply reservoir holds one or more of: enzymatic cleaners, high-level disinfectants, or liquid chemical sterilant.

4. The system of claim 2, wherein the cleaning supply reservoir holds concentrated disinfectants or sterilants that are automatically diluted with water to a predetermined concentration for use in reprocessing the medical device through the use of a dosing pump.

5. The system of claim 1, wherein the medical device washer-disinfector includes a heating element to increase a temperature of the reprocessing fluids in the closed-loop fluid pathway in the medical device washer-disinfector.

6. The system of claim 1, wherein the medical device washer-disinfector includes a water storage system connected to the closed-loop fluid pathway.

7. The system of claim 6, wherein the water storage system includes a clean water reservoir connected to the closed-loop fluid pathway, wherein the clean water reservoir holds one or more of: distilled water, deionized water, or purified water.

8. The system of claim 6, wherein the medical device washer-disinfector includes a water filter connected to the water storage system and the closed-loop fluid pathway, wherein tap water flows through the water filter and the water filter filters out water-borne pathogens.

9. The system of claim 6, wherein the water storage system includes a waste water reservoir connected to the closed-loop fluid pathway.

10. The system of claim 1, wherein the medical device washer-disinfector includes a lubrication system with a primary lubricant pump connected to the closed-loop fluid pathway to apply a lubricant to the medical device after a completion of the reprocessing cycle, and further including a lubricant reservoir to store the lubricant.

11. The system of claim 1, wherein the medical device washer-disinfector includes a lubricant and a cleaning supply that are packaged into a single combined package.

12. The system of claim 1 further comprising:
an RFID/NFC system that includes an RFID/NFC scanner located within the medical device washer-disinfector that is configured to scan an RFID/NFC tag located within the one or more medical devices, wherein the RFID/NFC scanner scans the RFID/NFC tag when the one or more medical devices is loaded into the medical device washer-disinfector in a proper orientation, wherein the RFID/NFC system facilitates an identification of the medical device as suitable to be reprocessed within the medical device washer-disinfector and a prevention of reprocessing of the medical device that is not intended to be reprocessed within the medical device washer-disinfector.

13. The system of claim 12, wherein the RFID/NFC system tracks a number of times the medical device has been reprocessed with the medical device washer-disinfector by writing to RFID/NFC tag after every successful reprocessing.

14. The system of claim 12, wherein the RFID/NFC system includes a database that stores one or more of: various reprocessing cycles, material requirements for the medical devices, the medical devices, a history of reprocessing cycles, or a history of medical devices used with the medical device washer-disinfector.

15. The system of claim 1 further comprising:
an internal control circuit for controlling the reprocessing cycle with software, the internal control circuit includes a scanner to scan the one or more medical devices and a plurality of sensors that validate the lid is completely closed during the reprocessing cycle, prevent disinfection of non-system components by recognizing an absence of a valid scan on the non-system components and preventing activation of the reprocessing cycle, wherein the medical device washer-disinfector is registered to accept a placement of the one or more medical devices in a specific orientation to enable each medical device to be scanned by the scanner within the medical device washer-disinfector.

16. The system of claim 15, wherein the internal control circuit and the scanner validates an authenticity and a remaining longevity of each one of the one or more medical devices placed within the medical device washer-disinfector in order to begin the reprocessing cycle and writes data to a data-storage tag in each of the one or more medical devices following a successful completion of the reprocessing cycle.

17. The system of claim 1, wherein the medical device washer-disinfector is battery-powered that includes a rechargeable battery that is internally housed in the base unit.

18. The system of claim 1, wherein the interface between the first flow connector and the second flow connector and the first end and the second end of the medical device includes flanges and magnets on the first end and the second end of the medical device connecting to the first flow connector and the second flow connector.

19. The system of claim 1, wherein the medical device washer-disinfector is basin-less and the reprocessing fluids do not submerge the medical device in a basin or collection area.

20. A portable, medical device washer-disinfector to execute a reprocessing cycle with one or more medical devices, the medical device washer-disinfector comprising:
a base unit and a detachable case configured to detach from the base unit, wherein the base unit houses a set of fluid components, a set of electronics, and a power supply to enable operation of the portable, medical device washer-disinfector, the detachable case includes a mounting tray configured to hold the one or more medical devices, wherein the detachable case provides a user access to the medical device and an ability to refill input water and drain waste water from a previous cycle, and a lid that provides access to the mounting tray, wherein the base unit and the detachable case are personal, hand-held, and used by a user while being carried;
a first housing with a first flow connector configured connect to a first end of the medical device;
a second housing with a second flow connector configured to connect to a second end of the medical device, thereby creating a closed-loop fluid pathway for reprocessing fluids to flow through the one or more medical devices and the medical device washer-disinfector, wherein the reprocessing fluids are fully contained within the first flow connector, the second flow connector, and the medical device, wherein an interface between the first flow connector and the second flow connector and the first end and the second end of the medical device provides a water-tight and air-tight seal forming the closed-loop fluid pathway; and
an RFID/NFC system that includes an RFID/NFC scanner located within the medical device washer-disinfector that is configured to scan an RFID/NFC tag located within the one or more medical devices.

21. The medical device washer-disinfector of claim 20 further comprising:
a cleaning supply reservoir connected to the closed-loop fluid pathway, wherein the cleaning supply reservoir holds one or more of: enzymatic cleaners, high-level disinfectants, or liquid chemical sterilant.

22. The medical device washer-disinfector of claim 20 further comprising:
a water storage system connected to the closed-loop fluid pathway,
wherein the water storage system includes a clean water reservoir connected to the closed-loop fluid pathway, and the clean water reservoir holds one or more of: distilled water, deionized water, or purified water, and
further wherein the water storage system includes a waste water reservoir connected to the closed-loop fluid pathway.

23. The medical device washer-disinfector of claim 20 further comprising:
a lubrication system with a primary lubricant pump connected to the closed-loop fluid pathway to apply a lubricant to the medical device after a completion of the reprocessing cycle, wherein the lubricant system includes a lubricant reservoir to store the lubricant.

24. The medical device washer-disinfector of claim 20, wherein the RFID/NFC scanner scans the RFID/NFC tag when the one or more medical devices is loaded into the medical device washer-disinfector in a proper orientation, wherein the RFID/NFC system facilitates an identification of the medical device as suitable to be reprocessed within the medical device washer-disinfector and a prevention of reprocessing of the medical device that is not intended to be reprocessed within the medical device washer-disinfector.

25. The medical device washer-disinfector of claim 20 further comprising:
an internal control circuit for controlling a reprocessing cycle with software, the internal control circuit includes a scanner to scan the one or more medical devices and a plurality of sensors that validate the lid is completely closed during the reprocessing cycle, prevent disinfection of non-system components by recognizing an absence of a valid scan on the non-system components and preventing activation of the reprocessing cycle, wherein the medical device washer-disinfector is registered to accept a placement of the one or more medical devices in a specific orientation to enable each medical device to be scanned by the scanner within the medical device washer-disinfector.

26. A method for reprocessing one or more medical devices, the method comprising:
enclosing a medical device in a cleaning-disinfection system, wherein the cleaning-disinfection system includes a portable, medical device washer-disinfector to execute a reprocessing cycle with one or more medical devices, wherein the medical device washer-disinfector is personal, hand-held, and used by a user while being carried, the medical device washer-disinfector comprises:
a first housing with a first flow connector configured connect to a first end of the medical device, and
a second housing with a second flow connector configured to connect to a second end of the medical device, thereby creating a closed-loop fluid pathway for reprocessing fluids to flow through the one or more medical devices and the medical device washer-disinfector, wherein the reprocessing fluids are fully contained within the first flow connector, the second flow connector, and the medical device;
sealing the first end of the medical device against the first housing and first flow connector, wherein an interface between the first flow connector and the first end of the medical device provides a water-tight and air-tight seal forming the closed-loop fluid pathway;
sealing the second end of the medical device against the second housing and the second flow connector, wherein an interface between the second flow connector and the second end of the medical device provides a water-tight and air-tight seal forming the closed-loop fluid pathway;
filling with water a clean water reservoir connected to the closed-loop fluid pathway;
activating a reprocessing cycle for the medical device washer-disinfector;
cleaning, by the medical device washer-disinfector, surfaces of the medical device with water and enzymatic cleaning detergents; and
disinfecting, by the medical device washer-disinfector, the surfaces of the medical device with high-level disinfectants or a liquid chemical sterilant.

27. The method of claim 26 further comprising:
storing the medical device within the medical device washer-disinfector; and
applying a lubricant to the medical device prior to the next use.

28. The method of claim 26 further comprising:
scanning and reading, by an RFID/NFC scanner located within the medical device washer-disinfector, an RFID/NFC tag on the medical device to confirm an authorized medical device for the medical device washer-disinfector; and
after the reprocessing cycle is complete, writing an incremental cleaning number to the RFID/NFC tag on the medical device.

29. The method of claim 26 further comprising:
filling a waste water reservoir connected to the closed-loop fluid pathway during the execution of the reprocessing cycle.

30. The method of claim 26 further comprising:
applying a replenishment hydrophilic coating to the medical device.

* * * * *